(12) United States Patent
McCallum et al.

(10) Patent No.: US 12,159,708 B2
(45) Date of Patent: Dec. 3, 2024

(54) HEALTHCARE OCCUPATIONAL OUTCOMES NAVIGATION ENGINE

(71) Applicant: Integer Health Technologies, LLC, Arlington, TX (US)

(72) Inventors: Jack McCallum, Benbrook, TX (US); Scott Roloff, Arlington, TX (US); William McCallum, Fort Worth, TX (US); Ken Grifno, The Colony, TX (US)

(73) Assignee: Integer Health Technologies, LLC, Fort Worth, TX (US)

( * ) Notice: Subject to any disclaimer, the term of this patent is extended or adjusted under 35 U.S.C. 154(b) by 273 days.

(21) Appl. No.: 17/864,631

(22) Filed: Jul. 14, 2022

(65) Prior Publication Data
US 2022/0359067 A1 Nov. 10, 2022

Related U.S. Application Data

(63) Continuation-in-part of application No. 15/225,503, filed on Aug. 1, 2016, now abandoned.
(Continued)

(51) Int. Cl.
G16H 40/20 (2018.01)
G06Q 30/0201 (2023.01)
G16H 50/70 (2018.01)

(52) U.S. Cl.
CPC ......... *G16H 40/20* (2018.01); *G06Q 30/0206* (2013.01); *G16H 50/70* (2018.01)

(58) Field of Classification Search
CPC ..... G16H 40/20; G16H 50/70; G06Q 30/0206
See application file for complete search history.

(56) References Cited

U.S. PATENT DOCUMENTS

| 5,550,734 A | 8/1996 | Tarter et al. |
| 5,704,044 A | 12/1997 | Tarter et al. |

(Continued)

FOREIGN PATENT DOCUMENTS

| AU | 2014249356 A1 | 10/2015 |
| CA | 2905769 A1 | 10/2014 |

(Continued)

OTHER PUBLICATIONS

Radnofsky, "Employers vs. Health Costs", The Wall Street Journal, Feb. 5, 2016, pp. 1, B2.

*Primary Examiner* — Robert A Sorey
*Assistant Examiner* — Kristine K Rapillo
(74) *Attorney, Agent, or Firm* — Vincent J. Allen; James H. Ortega; Carstens, Allen & Gourley, LLP

(57) ABSTRACT

A machine learning system and method utilizing artificial intelligence that improves the provisioning of healthcare and reduces the total cost of healthcare and lost productivity. The approach creates a quantifiable assessment of quality and a ranking number measuring a provider's quality of healthcare services. The machine learning system makes a determination of quality based on a clinical evaluation database, an employee related time and attendance database, and a costing database. The system analyzes how quickly a provider returns an employee to work at or near pre-absence productivity and at what cost. The system creates a ranking number that provides employees with a comparison of providers. Employees may then be incentivized to seek high value providers.

26 Claims, 69 Drawing Sheets

Related U.S. Application Data

(60) Provisional application No. 62/387,534, filed on Dec. 28, 2015.

(56) References Cited

U.S. PATENT DOCUMENTS

| | | | |
|---|---|---|---|
| 7,711,577 B2 | 5/2010 | Dust et al. | |
| 7,840,418 B2 | 11/2010 | Schoenberg | |
| 7,912,734 B2 | 3/2011 | Kil | |
| 7,925,519 B2 | 4/2011 | Greene | |
| 8,015,022 B2 * | 9/2011 | Gore | G06Q 10/1057 |
| | | | 705/14.1 |
| 8,036,916 B2 | 10/2011 | Dust et al. | |
| 8,100,829 B2 | 1/2012 | Rothman et al. | |
| 8,200,506 B2 | 6/2012 | Kil | |
| 8,224,665 B2 | 7/2012 | Morris | |
| 8,489,420 B2 | 7/2013 | Dust et al. | |
| 8,583,450 B2 | 11/2013 | Baker et al. | |
| 8,666,779 B2 | 3/2014 | McGuigan et al. | |
| 8,700,427 B1 | 4/2014 | Parks et al. | |
| 8,930,225 B2 | 1/2015 | Morris | |
| 9,424,532 B1 * | 8/2016 | Abedini | G06N 20/00 |
| 11,120,403 B2 | 9/2021 | Pande et al. | |
| 11,636,497 B1 * | 4/2023 | Talvola | G06N 20/20 |
| | | | 705/7.29 |
| 2001/0051913 A1 | 12/2001 | Vashistha et al. | |
| 2004/0039603 A1 | 2/2004 | Hanrahan | |
| 2004/0111291 A1 | 6/2004 | Dust et al. | |
| 2005/0228692 A1 | 10/2005 | Hodgdon | |
| 2005/0234742 A1 | 10/2005 | Hodgdon | |
| 2006/0019222 A1 | 1/2006 | Lelito et al. | |
| 2006/0078868 A1 | 4/2006 | Douglas et al. | |
| 2007/0072160 A1 | 3/2007 | Jolly et al. | |
| 2007/0118413 A1 | 5/2007 | Javors | |
| 2008/0077445 A1 | 3/2008 | Mecklenburg | |
| 2008/0086325 A1 | 4/2008 | James | |
| 2008/0147438 A1 | 6/2008 | Kil | |
| 2008/0147440 A1 | 6/2008 | Kil | |
| 2008/0147441 A1 | 6/2008 | Kil | |
| 2008/0306762 A1 | 12/2008 | James | |
| 2009/0099862 A1 | 4/2009 | Fireman et al. | |
| 2009/0150252 A1 | 6/2009 | Schoenberg | |
| 2009/0319296 A1 | 12/2009 | Schoenberg | |
| 2010/0004947 A1 | 1/2010 | Nadeau et al. | |
| 2010/0217625 A1 | 8/2010 | Dust et al. | |
| 2010/0223075 A1 | 9/2010 | Sparks et al. | |
| 2011/0120470 A1 | 5/2011 | Bowerbank | |
| 2011/0161094 A1 | 6/2011 | Haughton et al. | |
| 2012/0010898 A1 | 1/2012 | Dust et al. | |
| 2012/0185416 A1 | 7/2012 | Baras et al. | |
| 2012/0245953 A1 | 9/2012 | Morris | |
| 2013/0117033 A1 | 5/2013 | Mohlenbrock | |
| 2013/0332194 A1 | 12/2013 | D'Auria et al. | |
| 2014/0200907 A1 | 7/2014 | Dust et al. | |
| 2014/0244276 A1 | 8/2014 | Dyke et al. | |
| 2014/0249842 A1 | 9/2014 | Dust et al. | |
| 2014/0249843 A1 | 9/2014 | Dust et al. | |
| 2015/0149461 A1 | 5/2015 | Lemarroy et al. | |
| 2015/0199488 A1 | 7/2015 | Falchuk et al. | |
| 2015/0286792 A1 | 10/2015 | Gardner et al. | |
| 2015/0356486 A1 | 12/2015 | Alhimiri | |
| 2016/0042132 A1 | 2/2016 | Greene | |
| 2016/0092658 A1 | 3/2016 | Leenaerts | |
| 2016/0196398 A1 | 7/2016 | Vivero et al. | |
| 2016/0239613 A1 | 8/2016 | Siva | |
| 2016/0239614 A1 | 8/2016 | Siva | |
| 2016/0275432 A1 | 9/2016 | Guinness et al. | |
| 2018/0306762 A1 * | 10/2018 | Dong | G01N 33/0075 |

FOREIGN PATENT DOCUMENTS

| | | |
|---|---|---|
| EP | 1290605 A1 | 3/2003 |
| EP | 1936525 A1 | 6/2008 |
| EP | 2973350 A1 | 1/2016 |
| WO | 2001095223 A2 | 12/2001 |
| WO | 2010002947 A2 | 1/2010 |
| WO | 2015136555 A3 | 1/2016 |
| WO | 2016112230 A1 | 7/2016 |

* cited by examiner

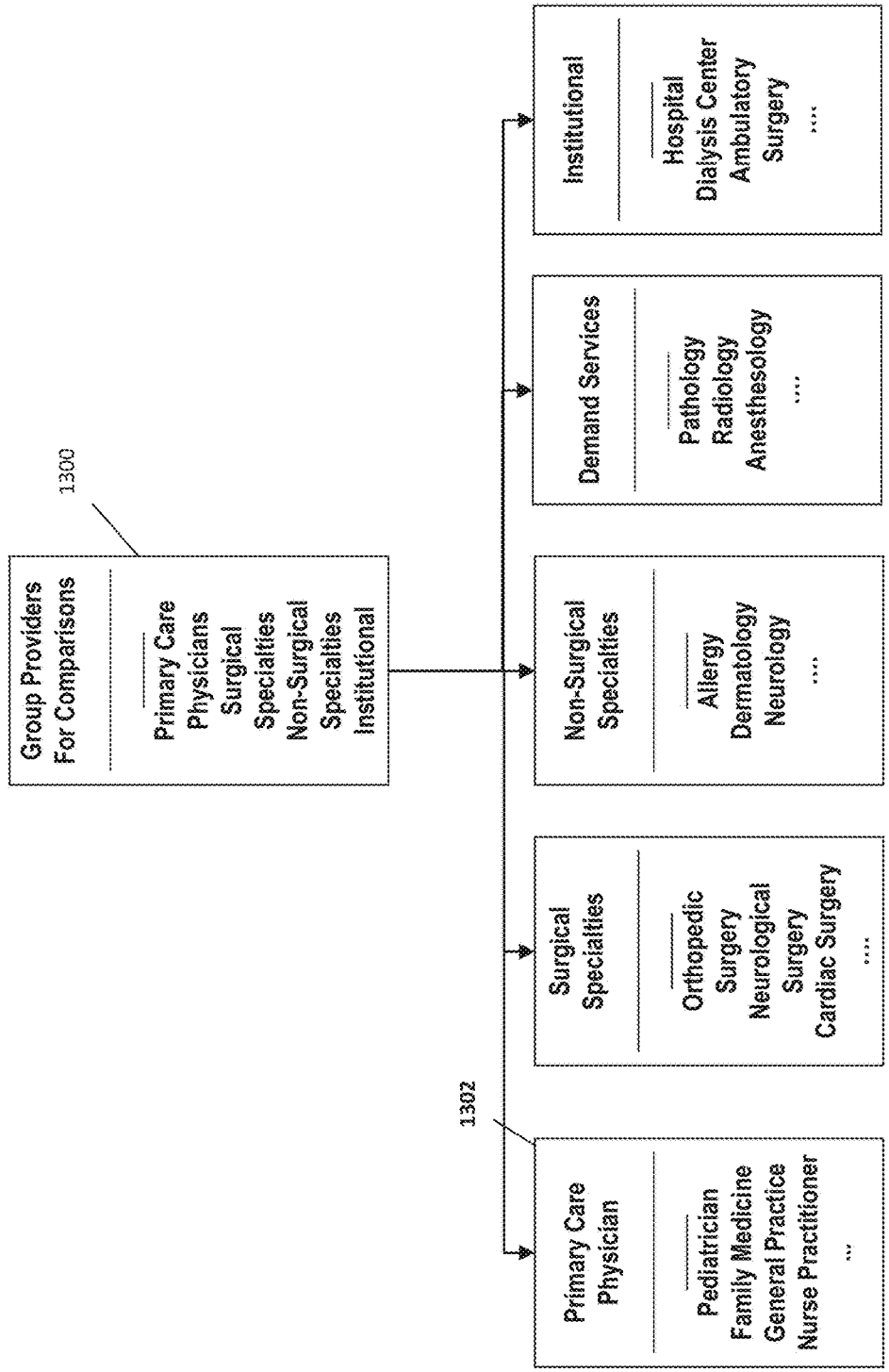

| Type of Database | Database Naming | Database Description |
|---|---|---|
| Industry Reference Databases | Alchemy | Collection of industry tables used in processing client data |
| | NEPPES | CMS National Identifier Database import to Microsoft SQL Server |
| | CMS HCC | Database containing tables to calculate Medicare Risk Factor |
| | USC-COPS | Database containing table to calculate USC's COPS Risk Factor |
| Logic Rules | LogicRules | Database containing Algorithmic logic rules |
| Stage Database | Stage_Client_XXX | Databases containing raw data or data extracted to claimed invention. This data mirrors the client's system |
| Production Database | PTO_Saver_XXX | Database with client data imported into Database |
| Combined Data | Master_Saver_XXX | Database containing data from multiple clients combined for analysis |

Fig. 17

| Database Name | Schema's | Description |
|---|---|---|
| Alchemy | CMS | Table origin is from Center of Medicare and Medicaid |
| | CDC | Table origin is from Center for Disease Control |
| | Database Object(default) | System default Schema |
| | Defaults | Table is used to set the default values in the production database |
| | FDA | Table origin is from Federal Drug Administration |
| | MGMA | Table origin is from Medical Group Managers Association |
| | MISC | Table origin is from various sources where the source is listed in the source table |
| | US Postal | Table origin is from US Post Office |
| NEPPES | Database C | System default Schema |
| CMS HCC | Database< | System default Schema |
| USC- COPS | Database< | System default Schema |
| LogicRules | LogicRules | Table is priority Algorithmic Logic |
| Stage Client xxx | Database Object (default) | System Default Schema |

Fig. 18

| PTO_Saver_ | Absence | Table data regarding employee absence, demographics and compensation |
|---|---|---|
| | Claims | Table contains data regarding medical claims |
| | Credential | Provider credentials information |
| | Database Object (default) | |
| | Dictionary | Relational tbl group data elements: medical claims/in absences & logic rules |
| | Evaluation | Data gathered during an employee health risk assessment |
| | Foundation | Relational table containing key data elements |
| | Optionlist | Relational tbl w/ descriptions and group data elements for OLAP cubes and reports |
| | Person | Relational table with key data elements regarding to the employee or dependent |
| | Schedule | Relational Database used in scheduling patient interactions |
| | WorkersComp | Relational table with data elements specific to a worker compensation population |

Fig. 20

| | Stored Procedure | Function |
|---|---|---|
| 3100 | Stored Procedure | Function |
| 3102 | Step 00 - Run Process | Used to automate other steps |
| 3104 | Step 01 - CreateTables | Creates all table need in PTO Saver Database |
| 3106 | Step 02 - PopulateData | Translates data in Stage Databases into IH PTO Saver Database |
| 3108 | Step 03 - CreateDictionaries | Populated Dictionaries+ OptionList data in tables from Stage, Alchemy, NEPPES and databases |
| 3110 | Step 04 - CreateFact | Populated OLAP database from PTO Saver Database |
| 3112 | Step 05 - HCCScore | Calculates HCC Risk Score and backfills PTO Saver database |
| 3114 | Step06- CDPSScore | Calculates COPS Risk Score and backfills PTO Saver database |
| 3116 | Step07 - LogicRules ChronicConditions | Determine patient w/chronic conditions: group patients by condition+ total medical expense |
| 3118 | Step07 - LogicRules EpisodicConditions | Determines patient w/episodic conditions: groups patients: condition +total medical expense |
| 3120 | Step07- LogicRules Workers Comp. | Determines patient w/worker's compensation claims, med. conditions+ totalmedical expense |
| 3122 | Step08- Qscore | Calculates each provider's Qscore |

Fig. 21

Functional Descriptions Step 00 - Step 03

Step 00 - Run Process
Used to automate other steps.

Step 01 - Create Tables
Creates all tables needed in the PTO_Saver Database (DB)

Step 02 - Populate Data
Stored procedure to populate production tables from raw data tables
This step is specific to the company supplying the data.
There are separate sections of code for each table being populated.
This step populates tables with a schema type of "Foundation", "Absence", "Person" and "Claims"

Step 03 - Create Dictionaries
This step populates- production tables with data from "Populate Data" and "Alchemy" to create lookup tables with standardized definitions.
The tables populated in this step have schema types of "OptionList" and "Dictionary"
The first record of these tables should contain a generic record that can be used to indicate what information from the source database was not available.

Fig. 22A

Functional Descriptions Step 04 - Step 06

Step 04 - Create Fact
Data is formatted into OLAP cubes for use in multi-dimensional reporting

Step 05 - HCC score
Medicare HCC risk adjustment SAS code is translated into TSQL code and executed in order to calculate a HCC risk score for each patient. This uses tables stored in the "HCC_2016" database.

Step 06 - CDPS Score
The uses calculations created by University of Southern California at San Diego for Chronic Illness and Disability Payment System (CDPS). The risk score is calculated for each patient using this system. This step uses tables stored in the "CPDS Ver6" database.

Fig. 22B

Functional Description for Episodic, Chronic, and Workers Compensation

Step 07 - LogicRules (Episodic, Chronic, and Workers Compensation)

1. Each medical claim is independently analyzed to determine if diagnosis, procedure, DRG, Revenue code or prescription rules are satisfied.

2. Each medical claim is independently analyzed to determine if the specific claim should be excluded base on diagnosis, procedure, DRG, Revenue code or prescription rules.

3. Patients are classified as "Chronic", "Episodic" or "Workers Compensation" Chronic Patients are analyzed using all expenses over time.

1. All the patient's expenses are tied to the primary treating physician.

2. Additional analysis is based on the type of provider seeing the patient.

Fig. 22C

Code Demonstrating Logical and Operational Functioning of Condition and Duration Constraint Episodic Patient are analyzed base on procedures tied to the specific condition and duration 1. Conditions that cannot be impacted are excluded.

```
SELECT TOP (100) PERCENT Claims.Charges.Person_Id, Claims.Charges.DateofService,
    Dictionary.Diagnosis.DiagnosisCode, Dictionary.Diagnosis.DiagnosisDescription,
    Claims.Charges.LogicGroup_Diag,
    Dictionary.ProcedureCode.ProcedureCode, Dictionary.ProcedureCode.ProcedureDescription,
    Claims.Charges.ProcedureGroup, Claims.Charges.LogicRule, Claims.Charges.LogicGroup,
    (ChronicConditionl,Foundation.Provider.ProviderName,
    Foundation.Provider.Specialty,[Optionlist I.(Specialtyl.[ChronicCondition_Groupl,
    Claims.Charges.AllowedAmount into
temp_PatientDetail
FROM Claims.Charges INNER JOIN
    Foundation.Provider ON Claims.Charges.Provider_Id = Foundation.Provider.Provider_Id LEFT OUTER JOIN
    Dictionary.ProcedureCode ON Claims.Charges.ProcedureCode_Id = Dictionary.ProcedureCode.ProcedureCode_Id
    LEFT
OUTER JOIN
    Dictionary.Diagnosis ON Claims.Charges.Diagnosis_Id = Dictionary.Diagnosis.Diagnosis_Id
    left outer join [Optionlisti.[Specialtyl
on Foundation.Provider.Specialty = [Optionlisti.[Specialtyi.Specialty
inner join [LogicRulesi.[Rulesi.[LogicGrouplon Claims.Charges.LogicGroup = [LogicRulesi.ifRulesi.[LogicGroupl.logicgroup
Where ([EpisodicConditionl = 'Exclude')
GROUP BY Claims.Charges. LogicGroup_Diag, Claims.Charges.
ProcedureGroup,Claims.Charges.LogicGroup,[ChronicConditionl
,Claims.Charges.LogicRule,Claims.Charges.Person_id, Claims.Charges.DateofService,
    Dictionary.Diagnosis.DiagnosisDescription, Dictionary.ProcedureCode.ProcedureDescription,
    Dictionary.ProcedureCode.ProcedureCode,Foundation.Provider.ProviderName,Claims.Charges.AllowedAmount,
    Dictionary.Diagnosis. DiagnosisCode,Foundation.Provider.Specialty ,[Optionlisti.(Specialtyi.[ChronicCondition_Groupl
ORDER BY Claims.Charges.Person_Id, Claims.Charges.DateofService
```

Fig. 23A

Code Logic Rule Functioning Condition & Duration Rule Not Satisfied

Step 07 — Episodic

1. Episodic Patients are analyzed base on procedures tied to the specific condition and duration. The first code set is for 'Same Date' and the second code set is for '30-1Days.'

2. Claims where a rule was not satisfied are analyzed in context with other claims to determine if they contributed to the overall cost of the episode.

```
update Claims.Charges
set LogicGroup = dbo.temp_LogicGroup_Diag_classified.logicGroup, LogicRule
= 'Same Date'
FROM   Claims.Charges INNER JOIN
       dbo.temp_logicGroup_Diag_classified
ON Claims.Charges.Person_Id = dbo.temp_logicGroup_Diag_classified.Person_Id
AND Claims.Charges. DateofService = dbo.temp_LogicGroup_Diag_classified.DateofService
where Claims.Charges.logicGroup ='No Rule Triggered' update Claims.Charges
set logicGroup = dbo.temp_logicGroup_Diag_classified.logicGroup, LogicRule =
'-30 to -1Days'
FROM Claims.Charges INNER JOIN
       dbo.temp_logicGroup_Diag_classified
ON Claims.Charges.Person_Id = dbo.temp_logicGroup_Diag_classified.Person_Id
AND Claims.Charges. DateofService between dateadd(d,-30,dbo.temp_logicGroup_Diag_classified.DateofService)
and dbo.temp_logicGroup_Diag_classified.DateofService where
(Claims.Charges.logicGroup ='No Rule Triggered')
```

Fig. 23B

LogicRules Workers Compensation Rules Not Satisfied

Workers Compensation are defined by a triggering event and when the patient is released to return to work at full duty.

1. May conditions omitted from episodic condition will be included in Worker Compensation 2. Analysis is based on the type of provider seeing the patient Select top 100 percent claims [identifies all the claims] Claims.Charges.
    Person_Id, Claims.Charges.DateofService, [correspondingly identifies a patient (person/employee) by medical claims a data extract of a TPA medical claims second database],
    Charges [costing of the medical claims], and
    DateofService [correspondingly, an employer's human resources first database].

3. Claims where a rule was not satisfied are analyzed in context with other claims to determine if they contributed to the overall cost of the episode.

Fig. 23C

Step 08 - QScore

For each condition type (Chronic, Episodic, Workers Compensation) and provider type (primary care physician, non-surgical specialist, surgical specialist, institution and demand services) the corresponding patient population is identified.

Each patient has an individual calculation for their risk score, total medical expense and absence expense Each provider is then ranked based on total risk adjusted absence expense Provider outside 2 standard deviations are individually review for possible extenuating circumstances.

Providers are assigned a Quality score based on their ranking

Fig. 23D

| Key | Charges |
|---|---|
| PK | Charge_Id |
| FK1 | ThirdPartyAdministrator_Id |
| | TPANativeKey |
| | CompanyNativeKey |
| | CompanyName |
| | Company_Id |
| | Company_Location |
| | Corporation |
| | WorkSite_Id |
| | WorkSiteName |
| | EmployeeNativeKey |
| | RevCode |
| FK3 | PersonNativeKey |
| | Person_Id |
| FK4 | ProviderNativeKey |
| | Provider_Id |
| | BillingProviderNativeKey |
| | BillingProvider_Id |
| | ReferringProviderNativeKey |
| | ReferringProvider_Id |
| | ServicingProviderNativeKey |
| | ServicingProvider_Id |
| | Ordering_ProviderNativeKey |
| | OrderingProvider_Id |
| | Midlevel_Provider_Id |
| | SupervisingProviderNativeKey |
| | SupervisingProvider_Id |
| | ClaimNumber |
| | EncounterNumber |
| | DateofService |
| | MonthofService |
| | AdmitDate |
| | DischargeDate |
| | LengthofStay |
| | TypeofService |
| | TypeofService_Id |
| | BillType |

| | |
|---|---|
| | CPT |
| | Mod1 |
| | Mod2 |
| | ChargeAmount |
| | NDC |
| | DiagnosisType |
| | Diagnosis1 |
| | Diagnosis2 |
| | Diagnosis3 |
| | Diagnosis4 |
| | Diagnosis5 |
| | Diagnosis6 |
| | Diagnosis7 |
| | Diagnosis8 |
| | Diagnosis9 |
| | Diagnosis10 |
| | Diagnosis11 |
| | RevenueCode |
| | HCPCS |
| | RVU |
| | Specialty |
| | Facility_Id |
| | Location_Id |
| | Location |
| | LocationNativeKey |
| | Department_Id |
| | Department |
| | PlaceofService |
| | PlaceofService_Id |
| | Units |
| | ClaimEnteredBy |
| | ClaimEnteredDate |
| | AllowedAmount |
| | InsurancePortion |
| | PatientPortion |
| | Fee |
| | CoPayAmount |

| | | |
|---|---|---|
| | OtherInsurancePayment | |
| | WorkRVU | |
| | PatientNumber | |
| | AccountNumber | ClaimType |
| | TotalPaid | |
| | TotalAdjustments | |
| | TotalBalance | |
| | Betos_Id | |
| | PrimaryInsurance_Id | |
| | CurrentInsuranceNativeKey | Provider |
| | PrimaryInsurance | |
| | PrimaryInsuranceNativeKey | |
| | FinanceClass_Id | |
| | FinancialClass | Person |
| | ResponsibleProviderNativeKey | |
| | ProcedureCode_Id | |
| | DiagnosisGroup_Id | |
| | Diagnosis_Id | ThirdParty |
| | ProcedureType_Id | Administrator |
| | DiagnosisGroup | |
| | ProcedureGroup | |
| | DrugType_Id | |
| | LogicRule | |
| | LogicGroup_Id | |
| | LogicGroup | |
| | LogicGroup_Diag | |
| | LogicGroup_CPT | |
| | LogicGroup_DRG | |
| | LogicGroup_RevCode | |
| | LogicGroup_NDC | |
| | Diagnosis_Group_WorkerComp | |
| | LogicGroup_ConditionType | |
| | Claim_Id | |
| | Injury_Id | |
| | LogicGroup_AssignedProvider_Id | |
| | corvel_doi | |
| FK2 | ClaimType_Id | |

Fig. 25A

| | PossibleInteractions | |
|---|---|---|
| PK | PossibleInteractions_Id | |
| FK1 | Person_Id<br>Sepsis<br>Opportunistic Infections<br>Cancer<br>Diabetes<br>Bone/Joint/Muscle Infections/Necrosis<br>Immune Disorders<br>Schizophrenia<br>Multiple Sclerosis<br>Seizure Disorders and Convulsions<br>Cardiorespiratory Failure<br>Congestive Heart Failure<br>Chronic Obstructive Pulmonary Disease<br>Aspiration and Specified Bacterial Pneumonias<br>Renal Disease<br>Pressure Ulcer<br>Chronic Ulcer of Skin, except Pressure<br>Artificial Openings for Feeding or Elimination<br>int1<br>int2<br>int3<br>int4<br>int5<br>int6<br>InteractionRiskScore | |

| Symbol | Meaning |
|---|---|
|  | One — Mandatory |
|  | Many — Mandatory |
| 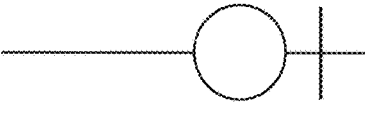 | One — Optional |
| 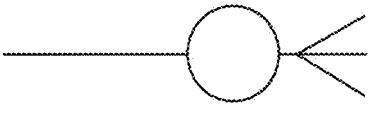 | Many — Optional |
Fig. 25Y

Fig. 26

HEALTHCARE OCCUPATIONAL OUTCOMES NAVIGATION ENGINE

CROSS REFERENCE TO RELATED APPLICATIONS

This application is a Continuation-in-Part application of U.S. patent application Ser. No. 15/225,503, filed Aug. 1, 2016, which claims the benefit of U.S. Patent App. No. 62/387,534, filed Dec. 28, 2015, and the foregoing applications are incorporated by reference herein in their entireties. Additionally, this application is related to U.S. patent application Ser. No. 15/950,681, filed Apr. 11, 2018, U.S. patent application Ser. No. 16/031,559, filed Jul. 10, 2018, and U.S. patent application Ser. No. 17/855,694, filed Jun. 30, 2022, all of which are incorporated by reference herein in their entireties.

TECHNICAL FIELD

The present disclosure relates to a machine learning system utilizing artificial intelligence that creates an assessment metric based on outcomes through analysis of unique data sets from specialized databases. A quality-based scoring system improves patient outcomes and reduces employer costs. A particular area of usefulness is in decreasing an employer's costs by identifying high value providers, defined as those providers who enable a self-insured employer's employees to return to work the most efficiently (i.e., at the lowest cost and in the least amount of time) and at or near pre-absence productivity levels.

BACKGROUND

Artificial intelligence and algorithmic development in machine learning systems has been explored since the 1970s, with the problem of encoding logical relationships. Researchers at Stanford University were trying to build a system that advised physicians on courses of antibiotics for treating bacterial infections of the blood and meningitis. They found that the medical knowledge consists mainly of logical relationships that can be expressed as if-then rules.

In healthcare, quality is currently measured using process metrics and customer satisfaction. The process is often centered around the provider network, whether it be hospitals or physician networks. In some cases, the provider network comprises the insurance company or Third Party Administrator (TPA), and in other cases a combination of, for example, a provider (and provider network) and the patient. Some processes are coupled with the employer's population of employees, of which the patient is a member. However, in all cases, the measurement of quality utilizing process metrics and customer satisfaction is flawed. The process fails to include the appropriate information available from a select group of employers. Further, basing quality on a process of customer satisfaction is very subjective. The quality process then looks to health indices that are garnered either demographically or geographically within a specific population group. Such indices are used to create a standard of quality that is generalized and not tied to the particulars that can reduce costs and improve quality and quality outcomes. Today, an estimated 30% of healthcare costs are unnecessary and result from poor or ineffective care.

There are many industry measures, such as Healthcare Effectiveness Data and Information Set (HEDIS) and Physician Quality Reporting System (PQRS), but these measure whether or not a healthcare provider followed a predefined process, not the actual patient's recovery.

Current quality methods are subjective. For example, a method may ask whether a particular patient received aspirin. Generally, claims information regarding, for instance, x-rays, imaging, lab tests, and prescription drugs are often generic in nature, and there is insufficient information on the individual claim to determine if it is part of a course of treatment. Analysis of all claims over a period of time is necessary to gain sufficient context to assign a cost to a patient's current condition.

In U.S. Pat. No. 8,036,916, entitled "Method of Optimizing Healthcare Services Consumption", the process for optimizing healthcare services consumption is accomplished by identifying a first group of patients from an employer based on prior patient claims and identifying a first group of providers based on specific practice patterns. The process prompts patients who have not met the healthcare requirements to seek services from the providers identified. By seeking solely to send a patient to a provider based on the provider's service patterns, the method presented in the foregoing patent fails to identify and address the true cost of healthcare which outweighs the claims costs.

Quality measurement in the current healthcare landscape and worker's compensation arenas are heavily focused on structure and process measures. The three most common outcome quality measures utilized are length of stay, re-admission rates, and mortality rates which are specific to the inpatient setting. Many times, provider attribution gets misassigned and is only focused on a specific inpatient stay. Cost in the current healthcare landscape also is focused on a specific visit or inpatient stay and is specific to only the medical and pharmacy claims cost measured by charge or fee schedule allowable amounts. These items remain independent due to individual providers and institutions having disparate billing, contracts, and documentation systems.

Medical and pharmacy costs for an illness or injury (workplace or otherwise) are only a portion of the true cost to manage a patient's or employee's condition. There exists a need to reduce the cost to employers while raising the positive outcome to patients or employees. A patient should be incentivized to see a "high value provider" based on a specific set of positive outcomes, which include returning an employee-patient back to work quickly at or near pre-absence productivity levels, thereby lowering the cost of care. Medical and pharmacy claims—the input into the healthcare equation—are measured in dollars and cents. Until now the output—what is received in exchange for those healthcare dollars—has been measured in qualitative terms, such as what a provider did or didn't do (compliance with HEDIS and clinical guideline checklists) and whether the patient "liked" the doctor or healthcare experience (scored by CAHPS and Press Ganey).

There remains a considerable need for a machine learning system utilizing coding, rules engines, and algorithms that identifies and measures risk based outcomes and utilizes positive outcomes as a basis for a risk based coding system. What is needed is a way to quantify the output—the patient's outcome—in dollars and cents so that the inputs and outputs are in the same terms, enabling the ranking of Healthcare Items based on the outcomes that they achieved and the calculating of ROIs (Returns on Investment).

SUMMARY

The invention is an engine, referred to herein as a search or navigation engine, that quantifies healthcare outcomes in dollars and cents based on the total risk-adjusted costs over the continuum of care—claims and medically-related absence costs—to get sick or injured employees back to work and/or keep them there. The medically-related absence costs are both a cost to employers, and measure the quality of care received by the employees. The quicker the employee returned to work, the more effective the care was. Quantifying healthcare outcomes permits ranking healthcare-based items by the outcomes that they achieved, such as physicians, facilities, case managers, workers' compensation adjusters, treatment patterns and/or practices, plans, programs, and networks, etc. (collectively, "Healthcare Items"), and calculating returns on investment.

Exemplary embodiments disclosed herein include a machine learning system utilizing artificial intelligence to identify constraints and define and redefine a risk-based scoring system through a series of comparative rules engines powered by algorithms. The machine learning system pulls data from databases of providers, employees, clinical evaluators and employers. As used herein, the term "healthcare provider" is not limited to simply physicians or only certain medical professionals, but includes, though is not limited to, other medical practitioners, facilities, case managers, workers' compensation adjusters, treatment patterns and/or practices, plans, programs and networks. This data is analyzed by an artificial intelligence machine learning system and reflects changing parameter values. These values reflect changing outcomes for the employee with respect to improved provisioning of healthcare, and for the employer as lowering of healthcare costs. A clinical evaluator (or a provider) visits the employee initially to perform a physical and then periodically thereafter, providing continuing input to the machine learning system, which allows the system to learn so that it can adjust quality factors based on changing conditions and further provide feedback to the provider. With the system, the provider can assess the success of a particular course of treatment.

The overall system creates a feedback loop that is used to improve the healthcare treatment for individual employees for particularized treatments for specific conditions in real time. The system creates a quality score that is used in ranking high value health care providers and is used to compare providers providing care under specific treatment protocols and specialties. This ranking system creates a method of guiding an employee/patient to a particular high value provider through an incentive program which provides payment to an HSA of an employee for choosing the high value provider. This scoring system is constantly adjusted and updated with computer generated data and human input (from clinical evaluators).

Disclosed further is a method of incentivizing employees to seek out high value providers. An employer, through an employee's Health Savings Account (HSA), provides a financial incentive in the form of additional money deposited into the HSA to encourage the employee to go to the high value providers in the employer's physician network or individual high value providers. Providers receive remuneration for handling the clinical evaluations conducted by evaluators or providers, who may be nurses, nurse practitioners, physician assistants. Other means of getting employees and others to high-value providers include narrowing the provider network, stratifying the health plan, and steering through case managers, workers' compensation adjusters, and referring physicians (note that although the analytics are derived from employee data, the results can be used to guide anyone to better care), and by giving patients a "Find a Provider" tool to look up the best providers themselves.

BRIEF DESCRIPTION OF THE DRAWINGS

A complete understanding of the present disclosure may be obtained by reference to the accompanying drawings in conjunction with the subsequent, detailed description, in which:

FIG. 7B depicts various provider groupings by specialty for comparison.

FIG. 17 is a table of types of databases utilized, the database name in the examples disclosed herein, and a description of functionality.

FIG. 18 is a table of databases utilized for risk adjustments, assessments, and standards, such as National Plan and Provider Enumeration System (NEPPES), Centers for Medicare and Medicaid Services Hierarchical Condition Categories (CMS HCC) University of California San Diego Chronic Illness and Disability Payment System (USC-CDPS), and Centers for Disease Control and Prevention (CDC).

FIG. 20 is a table with a description of the PTO_Saver_XXX database, which is the standard form from the Master_Saver database and contains the same schema as described in FIG. 19 above; however, this database also allows for the use of particularized data of employers and providers, including employee data.

FIG. 21 is a table identifying the list of stored procedures which are used to contain and identify a series of automatic tasks that the system can perform upon data input. These include identification, analysis, creation of non-transitory algorithms, and input and output of data over secured pathways over the cloud or a network, and are identified in the following manner, Step00—Run Process, Step 01—CreateTables, Step 02—PopulateData, Step 03—CreateDictionaries, Step 04—CreateFact, Step 05—HCCScore, Step 06—CDPSScore, Step 07—LogicRules (e.g., LogicRules ChronicConditions, LogicRules EpisodicConditions, LogicRules WorkersCompensation), and Step 08—Qscore.

FIG. 22A depicts Stored Procedure: Step 00—Run Process, Step 01—Create Tables, Step 02—Populate Data, and Step 03—Create Dictionaries, respectively, with their functions.

FIG. 22B highlights aspects of Step 04—Create Fact, Step 05—HCC (i.e., Hierarchical Condition Category) Score, and Step 06—CDPS (i.e., Chronic Illness Payment and Disability System) Score. Chronic Illness and Disability Payment System (CDPS) is a diagnostic classification system that Medicaid programs can use to make health-based capitated payments for TANF (e.g., Temporary Assistance for Needy Families) and disabled Medicaid beneficiaries.

FIG. 22C highlights the general rules that apply to presentation of data to the system prior to structuring in a database or through schema in a database, in accordance with diagnosis, procedure, DRG (i.e., diagnosis related group), Revenue Code (e.g., UB Revenue Code on a Claim), or prescription rules, as appropriate.

FIG. 23A describes an episodic employee (patient) and data analysis tied to specific conditions and duration. Conditions that cannot be impacted may be excluded.

FIG. 23B describes an episodic patient (employee) and data analysis tied to a specific condition and duration.

FIG. 23C depicts the system application code functioning with additional conditions not found in an episodic patient (employee). Here, Workers Compensation is defined by a triggering event and when the patient (employee) is released to return to work at full duty.

FIG. 23D describes Step 08—QScore, in which providers are assigned a quality score (or QScore).

FIG. 25A depicts the PTO-Saver Charges table, describing the various objects under consideration for the system.

FIG. 25L depicts the PTO_Saver PossibleInteractions table.

FIG. 25Y depicts a legend for symbols used in FIGS. 25A-25X.

FIG. 26 depicts an example of the cost calculation by Provider Depicting the QScore (e.g., QScore Card).

DETAILED DESCRIPTION

Figure 1A:
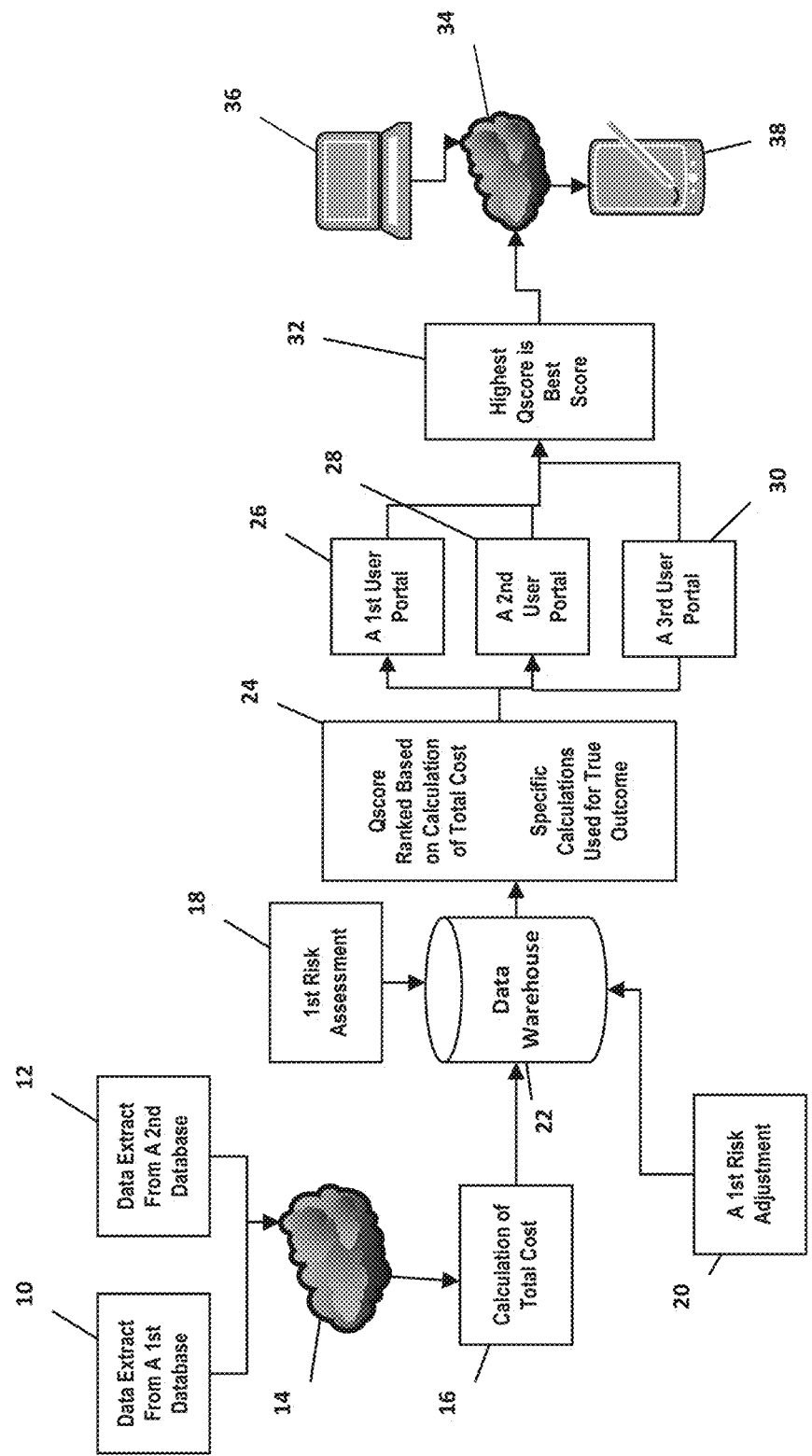
FIG. 1A depicts a process flow in which data extracts from at least two databases are communicated to a data calculation system and provided to a data warehouse. The data extracts are risk assessed and used to calculate a risk score juxtaposed against other data constraints. The results are output to one of a plurality of portals and communicated over the web.

Various objects, features, aspects, and advantages will become more apparent from the following detailed description along with the accompanying drawings. The principles are described with specificity; however, the description and drawings are not intended to limit the scope of the principles disclosed herein. Rather, the principles might also be embodied in other ways and to include different steps or combinations of steps similar to the ones described herein.

This invention is a navigation engine that quantifies healthcare outcomes in dollars and cents based on the total risk-adjusted costs—claims and medically-related absence costs—to get sick or injured employees back to work and/or keep them there. The disclosed technology improves the computer's functionality by transforming the literal display of data into a visual one on a single computer screen; thereby improving computer and network performance by decreasing the resources used to open and close screens while searching for the right one, while increasing the effectiveness and speed of the user's search process.

Also disclosed is an artificial intelligence machine learning application that utilizes a data extract (DE) from a first database and a data extract from a second database. The data is extracted and communicated to a data repository for a first data calculation of a total cost. A first risk assessment and a first risk adjustment provide a risk adjusted output which is communicated with the data extract of the first database and the data extract from a second database to a relational data warehouse.

In some applications, the volume of data to be processed and analyzed requires a system of a complex nature. Preferably, multi-processor high speed machines are used to provide a complete processing of the databases and extraction of the datasets. In some applications, the number of calculations requires a machine with sophisticated computing power and artificial intelligence that utilize complex algorithms comparing and analyzing data utilizing stored procedures.

In some embodiments, the centralized relational database communicates with a machine learning rules engine that ranks Healthcare Items on an algorithmic driven basis to determine a total cost for an outcome. The rules engine ranks outcomes based on total cost. Data from the rules driven engine is pushed or pulled to a series of portals for input and output including a first user portal, a second user portal, and a third user portal. There may be any number of additional portals. These portals transfer data to results directed from a first user portal, a second user portal, and a third user portal, which when compared, yield directed results, meaning that an action is directed based on the user that results in a best possible outcome. The score generated is a risk adjusted score and is transmitted over an encrypted secure worldwide web or VPN (virtual private/public network).

In some embodiments, analysis of data extracts from at least three databases defines specific data sets within each database through an artificial intelligence tool utilizing algorithm layers that compare predicted results to outcomes utilizing predictive analytics. Output is utilized from the at least three databases, including a data extract from a first database, a data extract from a second database, and a data extract for a third database, as well as data provided by the data warehouse. The data warehouse interfaces with a series of stored procedures and adjustment tables calculating a first Healthcare Item/patient risk score, a second Healthcare Item/patient risk score, and a third Healthcare Item/patient risk score. A stored procedure interfaces with the data warehouse (in some cases a centralized relational database) to calculate a total cost. The total cost is stored in the data warehouse, where a first grouping algorithm, a first ranking algorithm, and a first identifying algorithm compare data from the data warehouse. The data is processed through the artificial intelligence and compared with the rules for refinement as a compliance tool, then transmitted back to the data warehouse through the at least three algorithms (a first grouping algorithm, a first ranking algorithm and a first identifying algorithm) to data marts.

Algorithm layers define a sequence of potential events. In a first algorithm layer, individual claim lines are grouped by either diagnosis or episode of care. A grouping algorithm allocates claims cost for drugs, encounters, and diagnostic and therapeutic procedures, etc. to specific diagnostic groups, such as, diabetes, chronic lung disease, repetitive stress injury, and others. In a second algorithm layer, providers are sorted to clinically related groups such as primary care provider, non-surgical specialist, surgical specialist, and institution. In a third algorithm layer, an allocation to specific enterprise cost (in one instance, productivity) to episodes of care or diagnosis (or both) is based on employee compensation rates, paid time off policies, worker's compensation policies, benefit structures and stop loss coverage. In a fourth algorithm layer, population is risk adjusted. In a fifth algorithm layer, providers are assigned specific quality scores based on total cost of care and outcome, which are defined in terms of return to full job related function. The system ranks providers based on that score. Such quality scores are adjusted to individual patient needs based on factors, and providers may have more than one quality score.

In some embodiments, the risk based scoring system is used to measure providers in a provider network, where such providers provide care to employees of a self-insured employer or other claims holder (e.g., workers' compensation plans, workers' compensation insurers and TPAs can also use the methods described herein by substituting the indemnity payments to injured workers for the employer absence costs). Analysis is performed for at least the two preceding years and in some cases more to gain a historical perspective on a self-insured employer's or claims holder's group of employees or patients. The data is added to a centralized database for comparative purposes. Utilizing an analytics platform, high value providers in the self-insured employer's healthcare network are identified. Accordingly, a self-insured employer's healthcare costs are decreased and the employee's healthcare is improved by identifying high value providers in the self-insured employer's healthcare network. The term "high value providers" refers to those providers who attain the best outcomes (i.e., get employees back to work the fastest, at the lowest out of pocket costs, and where the employee can resume their duties at or near their pre-illness or pre-accident level of productivity).

A high value provider's score may adjust up or down based on outcomes achieved for each employee such that a high value provider may lose that designation as quality scores are adjusted based on input to the machine learning system.

The machine learning system establishes a baseline by analyzing historical data of the employer on each employee's healthcare costs, conditions, treatment protocols and as many as or as few parameters as appropriate, sometimes as few as one. The data from this analysis is interpreted by users and/or providers, and that data is saved and recorded in the system. It may be used for determining how much an employer would have saved had they been utilizing this system. Further the data can be used for comparative analysis with present data. After the analysis of historical data (or before or concurrently with such analysis), each employee may receive a physical from a provider and that data is entered into the system.

Utilizing a machine learning system, the risk based scoring system is updated and applied to providers in a provider network, where such providers provide care to employees of a self-insured employer or other claims holder (e.g., workers' compensation plans). Applying the system to such providers improves outcomes of risk based coding systems. Disclosed is a method of accessing data and associating data for the at least three databases with corresponding datasets that identify at least three specialized databases. In some cases, as few as one database may be utilized to determine a rate critical step in the method disclosed, namely the analysis of time and attendance data from an employer's database. The combination of information from at least three databases returns data tables having clinical claims costing data, employer time and attendance data (e.g., absence data), and pharmacy benefit management costing records relating to a particular employee's absence costs. Hereinafter, an employee's time away from work, whether through accident or illness, will be referred to as absence from work or paid time off (PTO) depending on the parameters used by the artificial intelligence system to make appropriate assessments and adjustments.

A computer-based system creates a quantifiable assessment of quality and a ranking number that measures the quality of provisioning of healthcare. The quality score is assigned to each provider. Each provider may have more than one quality score depending on the specialties that the provider provides to an employee. These quality scores can change depending on the success of each treatment protocol for each employee. These quality scores may go up or down depending on the success of the treatment protocol for an employee. Additionally, a provider may have more than one quality score, once again depending on the specialties or services provided by a provider. The determination of quality provided by a provider may be determined, for instance, on a data extract from a first database containing a first dataset from an employer's human resources database, and in particular the time and attendance data found in the human resources database, and a second database containing a second dataset from medical claims of a third party administrator (TPA), and a third database containing a third dataset of pharmacy data from a pharmacy benefits manager.

The system, through stored procedures, extracts data in an extraction process from at least three databases, including an employer human resources database, a third party administrator (TPA) medical claims database, and a pharmacy benefits manager database. As described in the drawings, an electronic medical record is captured on a mobile device and processed through a data translation tool used to translate data appropriately without normalizing the data for loading into a centralized relational database within a data warehouse. An artificial intelligence tool compares predicted results to actual outcomes utilizing predictive analytics. The predictive analytics applies rules through a matching, refinement, and redefining process based on changing conditions, provider specialties, and type of provider.

The datasets of at least three databases are transferred to a data translation tool for importing data to a data container, where the data is transformed to appropriate formatting (e.g., height of cell, size of cell in a data structure) by stored procedures and comparator tools based on algorithms of the artificial intelligence system. The data is formatted for the appropriate data base schema. The transfer of data is through an encrypted protocol through which mobile devices may access and initiate actions. The data is extracted, imported, transferred, translated and loaded into a centralized relational database. Other processes within the machine learning application may draw data from the centralized relational database for comparison and analysis. The centralized database is partitioned into individual stores of data. A rules engine accesses data from the relational database utilizing algorithms as well as artificial intelligence based on the rules engine refining the rules, which creates a ranking number of inherent quality (QScore) with combinations thereof performed on one or more specific and specialized computers (a server machine with processing and storage capabilities for analyzing millions of records per client, per client employee, per each database, and each dataset per each database) including several distinct interfaces (portals), one for each participant (e.g., employer, employee, provider, clinical evaluator, and miscellaneous) in the system. Additionally, there is an employer or client interface (a dashboard like website where each employee or patient data resides) and a provider portal (physicians, clinical evaluators or medical practitioners), a processor (a quad core high speed multi-processor system or better for high speed analysis in a server machine), a type of non-transitory memory (a series of memory cores), a display (preferably LED or OLED), and a network interface to provide VPN access over the cloud (HIPAA VPN encrypted). The machine learning system utilizes a process, which can be embodied in hardware, software or both, of receiving on the computer a first dataset associated with a first database and a first query attribute (a query generated by a data input associated with a particular record of a particular user) via the user interface across the cloud and into the processor. This model or embodiment also has a process of accessing on a processor a second dataset associated with a second query attribute of a second database contained in the memory and a third dataset associated with a third query attribute of a third database contained in the memory relating to a particular record identifying a particular user attribute of a dataset (e.g., a subset of data within a database) of a computer system. Further, this computer-based method has a process of accessing on a processor a stored dataset in the memory storage location containing the predetermined datasets. A plurality of attribute combinations of a first, a second and a third database are created by merging previously submitted and assessed attribute profiles of the first dataset of a first record from the attributes of a first database, and attribute profiles of a second dataset of a second record from the attributes of the second database, and attribute profiles of a third dataset of the third record from the attributes of the third database. The method creates attribute profiles consisting of treatment patterns, conditions, costs and other parameters of a record identifying an employee of a self-insured employer and the associated provider network, such as physicians, clinical evaluators, and medical practitioners. The attribute profiles are used in analyzing and comparing data, and the attribute profiles utilize algorithms in a comparator mode. Additionally, prior attribute profiles are created through an analysis of historical data.

Further disclosed herein is a process of identifying attribute combinations from the stored dataset of predetermined attribute combinations associated with the dataset that occur in the attribute profile of the record being analyzed by comparing the attribute combinations occurring in both the attribute profiles of the record. Once the attribute profiles are identified, then quantifiable assessment criteria are generated and ranked for the record based on the identified attribute combinations appearing in both a predetermined dataset and in the attribute profile of the record or historical data. Historical data is utilized to provide a basis for future cost comparisons. Further disclosed is a method whereby a self-insured employer or claims holder can understand the potential savings in the provisioning of quality care that could have occurred as a result of knowing what-if scenarios, such as for example, what if the self-insured employer had been utilizing the service in the past. By viewing the historical perspective of the provider costing information and the corresponding time and attendance data of an employee over the same time period, the employer can create a quality ranking number rating the quality of care already provided, which can be compared against future quality scoring ranking numbers of the same or different providers. This disclosure qualifies data that is not a part of an attribute profile of a dataset through an analysis of outlier claims. Algorithms are used to link dissimilar claims to a specific treatment pattern. Claims information regarding x-rays, imaging, lab test, and prescriptions is particularized in nature, not generic as is often used. The algorithm determines whether there is sufficient information on the patient's claim to determine if it is part of a course of treatment or an outlier claim. Analysis of most or all claims over a period time is necessary to gain sufficient context to assign the cost to the correct condition and provide for a true blending of healthcare costs and quality for an outcome that is non-subjective, definable, and measurable.

At least one stored procedure of the centralized relational database automates at least a first population risk adjustment table. A stored procedure calculates at least one individual risk score. A first risk assessment is operationally combined with the first risk adjustment and data extraction from at least three databases in order to calculate a cost of total absence.

The embodiments described are only used with claim holders (e.g., self-insured employers and workers' compensation plans). In the healthcare embodiment described below, an employer self-insures. The employer, not the insurance company, owns the medical and pharmacy claims, and the third party administrator acts to manage the claims payment of the employer. The specialized provider and the clinical evaluator provide factors used in continuing risk adjustments for system function. This embodiment creates a quality based scoring system utilizing positive outcomes as a basis for a risk based coding system for providers in a self-insured employer's healthcare network. Cost of an employee being absent from work due to accident or illness can be several times the claims cost. The process generally comprises: (1) the collection of data from self-insured employers out of the PBM (Pharmacy Benefit Management Plan) and TPA (Third Party Administrator) datasets (tables, records and reports) of specialized databases; (2) algorithms of the machine learning system group the claims by diagnosis (e.g., back, shoulder, knees, etc.); (3) all of the related claims on a patient-by-patient basis are linked together; (4) human resource records such as time and attendance are juxtaposed; (5) determining from the claims how long an employee (patient) was off (absence or paid time off (PTO)) and calculating the cost of the PTO and/or absence based upon the employee's compensation (or a normalized rate for all employees); (6) combining claims and PTO and/or other absence costs, then risk adjusting the total cost; (7) calculating each provider's average risk adjusted cost by diagnosis and determining whether a provider is worse than average for a particular diagnosis group (thereby costing the employer too much) or better than average for a particular diagnosis group (thereby saving the self-insured employer money). Young employees may have lower costs than older ones with medical problems, so an algorithm is applied to account for this.

Data may be pooled or combined so that all employers in a given geography benefit from each other's experience.

This is particularly useful when calculating the costs of smaller employers with smaller localized employee numbers. This approach is particularly effective for those employers who do not have a sufficient employee pool to provide enough information in order to rank a provider as a high value provider. The data of a large employer in a given geographic area can supplement the provider pool ranking of another employer. To protect data privacy, each employer only sees its own data on the web-based employer portal. Medical professionals, practitioners and clinical evaluators work with each employer to interpret and provide actionable insights.

A regression analysis may be performed on providers and the treatment protocols provided to employees to determine a reason for why a particular employee responded well to a treatment protocol while another employee with a similar condition or injury failed to respond as well. This regression analysis improves the quality of individualized treatment for each employee as it provides a method for a provider to learn what works best in any given treatment scenario.

In some embodiments, the system utilizes sets of other stored procedures and algorithms: a grouping algorithm, a condition identification algorithm, and a ranking algorithm. In one example, the ranking algorithm is further subdivided to correlate providers based on total cost of provided care to an employee and based on total absence expense. The combined data is processed and transferred to user data marts and then through the web to desktops and mobile devices for output to users.

In some embodiments, the lost productivity measure of a self-insured employer is aligned with claims holders' cost associated with the employee's absence (time away). Such costs are identified by employer rules for absences from work due to an employee's chronic or episodic conditions or injury. The lost productivity measure and claims holders' costs are matched with a provider or providers who can reduce the employee's absence from work (time away and or paid time off) with the best possible outcome. As used here, "outcome" is a measure of the cost to return an employee (patient) back to work at or near the employee's pre-absence productivity. The outcome measurement produced is a quality score (QScore) that can be used to compare providers. Providers are, for example, primary care physicians (PCP), surgical specialties, non-surgical specialties, demand services, pharmacies and institutional healthcare entities. Data algorithms are used to merge and define terms and create risk scoring numbers for ranking of healthcare based on outcomes. The data algorithms operate on data stored in the medical claims database of the TPA, pharmacy data sets, and human resource datasets (including, in particular, the time and attendance data in a human resource database) for complete cost and lost productivity capture. To measure the person's true outcome, the time associated with the patient's condition and how long it took the patient to get back to work are measured. Disclosed herein is a processing system having a method to gather data from selective datasets and a process of analyzing selective datasets according to logical constraints (i.e., a rules engine based on algorithms). The processing system and methods define criteria and necessary actions to determine outcomes based on quality assessments. Comparator logic compares a ranking number based on outcomes to a risk scoring system that creates a quantifiable assessment of quality.

Provider rankings are encapsulated in a QScore. The system further assigns a ranking score based on a grouping of factors for each provider achieving a positive outcome(s) as defined herein. The principles disclosed herein may be used to analyze large and varied sets of data and determine through algorithmic methods (acting as a rules engine) an outcome. A machine learning system is presented that utilizes artificial intelligence to create, identify, adjust and measure risk based outcomes through an analysis and assessment of data sets within specialized databases. The system can be used to incentivize providers of the self-insured employer's healthcare network, providing for more efficient improvement of employees. In addition, the rankings derived from the employee data can be used to move non-employees to the better providers and treatment patterns too.

Also disclosed is a regression analysis engine, which analyzes the collected data and identifies best practices for conditions, specialties, geographic and demographic analysis. This engine's algorithm determines the reason for one provider performing better than another provider. The engine's algorithm also determines if the best practices for one provider can be utilized by another provider, with the ultimate goal of improving the provisioning of healthcare. In the regression analysis engine, a first HVP code and a second HVP code are brought together to determine a cash or no cash situation. The regression engine is used for further analysis of blinded or non-blinded data for determining best practices in a particular specialty, by provider, geographically and/or demographically. This data provides sufficient information in a particular area (specialty, condition, geographically, or demographically) to provide a base of data not requiring individualized company-by-company analysis. Specifically, all providers in a given area would be included, with standardized best practices established so that a company may only need to use a subscription based model to get appropriate information for its employees. The regression engine also supports the filtering of data for later use in a subscription based model. This may be particularly useful where other employers in a given area do not need the analysis conducted on their data. For example, such other employers' providers may have already been analyzed and assigned QScores. Additionally, if other employers can utilize the data, even non self-insured employers could utilize the data for their employees. In some embodiments, a self-insured employer may not have a specific HSA program. In such cases, a gatekeeper program may be used in which an employer can require that its employees be referred to the HVP in all cases, or the employer can utilize the system's best provider database to provide its employees with a listing of the best providers. For specialists that are HVPs, a referral system can be employed as well.

Referring now to the drawings, disclosed are various embodiments of a system and method of enabling self-insured employers and claims holders of medical insurance claims to decrease cost and improve the employee's healthcare by identifying the high value providers. High value providers are those providers who can more quickly and effectively return an employee back to work at or near the employee's pre-absence productivity. The figures are not necessarily drawn to scale, and in some instances the drawings have been simplified for illustrative purposes only.

FIG. 1A depicts an overall view of the general process flow within a machine learning system. Shown are a data extract from a first database 10 and a data extract from a second database 12. The data is extracted and communicated over a communication interface over an encrypted secure cloud 14 and is interfaced with a data repository for a first data calculation of a total cost 16. A first risk assessment 18 and a first risk adjustment 20 provide a risk adjusted output which is communicated over an interface with the data extract of the first database 10 and the data extract from a second database 12 to a relational data warehouse 22. In rules driven engine 24, the relational data warehouse 22 communicates with a machine learning rules engine that ranks, for instance, users on an algorithmic driven basis according to a total cost for an outcome determination. Data from the rules driven engine 24 is pushed or pulled and communicated through a communication interface to a series of portals for input and output including a first user portal 26, a second user portal 28, and a third user portal 30. There may be any number of additional portals. These portals transfer data to results directed from a first user portal 26, and a second user portal 28, and a third user portal 30, which is compared, yielding directed results. Additionally, there are Provider Portals through which a Provider may see their own Doctor's Score Card (e.g., QScore or QScore Card). This means that an action is directed based on the user that results in a best possible outcome (combination of data extracts from the first data extract 10 and a second data extract 12, compared through a rules-based engine algorithm 32, for instance). The score generated by algorithm 32 is a risk adjusted score and is transmitted over an encrypted secure communications network 34, preferably via virtual private network (VPN), and transmitted by pull or push to a desktop 36 and a mobile device 38.

Figure 1B:
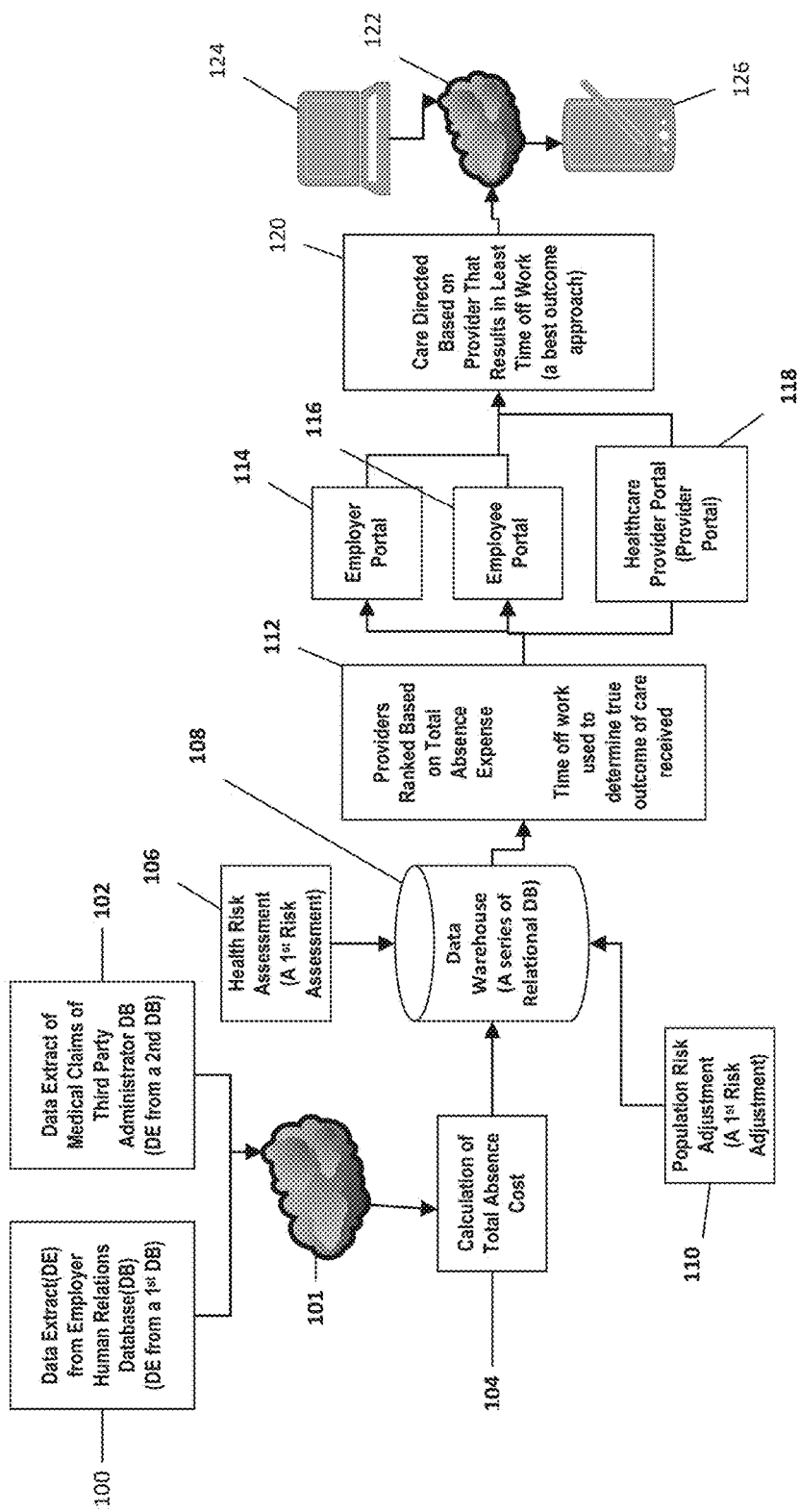
FIG. 1B depicts a process flow for an exemplary embodiment in which a combination of data extracts is used to determine the interrelationship of participants (such as employer, employee, and provider) in a healthcare arrangement based on a risk coding (a first risk adjustment, a second risk adjustment, and a third risk adjustment) created by the present machine learning system and method.

FIG. 1B depicts an overall view of the general process flow with data extract from a first database of a self-insured employer human resources database 100 and a data extract from a second database of medical claims from a third party administrator (TPA) 102. Data extracts from the self-insured employer human resources databases (e.g., time and attendance databases) 100 and the database of medical claims from a third party administrator (TPA) 102 are transmitted over an encrypted communication network 101 to a repository for a first data calculation of a total absence cost 104. The result is combined with a first health risk assessment (which can occur in a number of iterations) 106, and a first risk adjustment output 110, based on a population risk adjustment. There can also be a first, a second, and a third health risk assessment just like there can be a first, a second, and third risk adjustment. The risk adjustment output 110, in combination with data calculation of a total absence cost 104 and the first health risk assessment 106, is communicated over a communication interface to a relational data warehouse 108, which is interfaced with one or more storage mediums and one or more processors. The relational data warehouse 108 ranks providers based on an algorithmic driven calculation of a total absence expense for an outcome determination (rules engine ranks outcomes based on total absence expense) 112. Data is communicated from the total absence expense for an outcome determination 112, and in some cases is pulled from total absence expense for an outcome determination 112, to a series of portals for input and output including an employer portal 114, an employee portal 116, and a provider (e.g., healthcare provider in this embodiment) portal 118. These portals yield directed results (meaning that care is directed based on the provider that results in least time off work for an employee (patient)). Directed results are a combination of data extracts from the first database 100 and a second database 102, compared through a rules engine-algorithm based 120, and transferred over a communication network 122 to desktop 124 and mobile device 126.

A first risk assessment 106 describes rating an employee's changing health with respect to a quality score of a provider, such that, as the health of the employee (i.e., patient) improves over time, that result is consistent with a HVP (High Value Provider) high quality score. The risk assessment is one of several aspects that demonstrate the artificial intelligence of the system. Where the risk assessment lowers a HVP, the system responds by providing that information as well. For instance, when a Third Party Administrator (TPA) interrogates the system looking for quality scores of providers for a particular employee who may have a condition, and that risk assessment decreases relative to time and the provisioning of care by a HVP, then the system provides that information to medical practitioners with access in a non-sequitur manner. That is, the system responds to questions that are not asked but are important to provisioning of patient care.

Figure 2A:
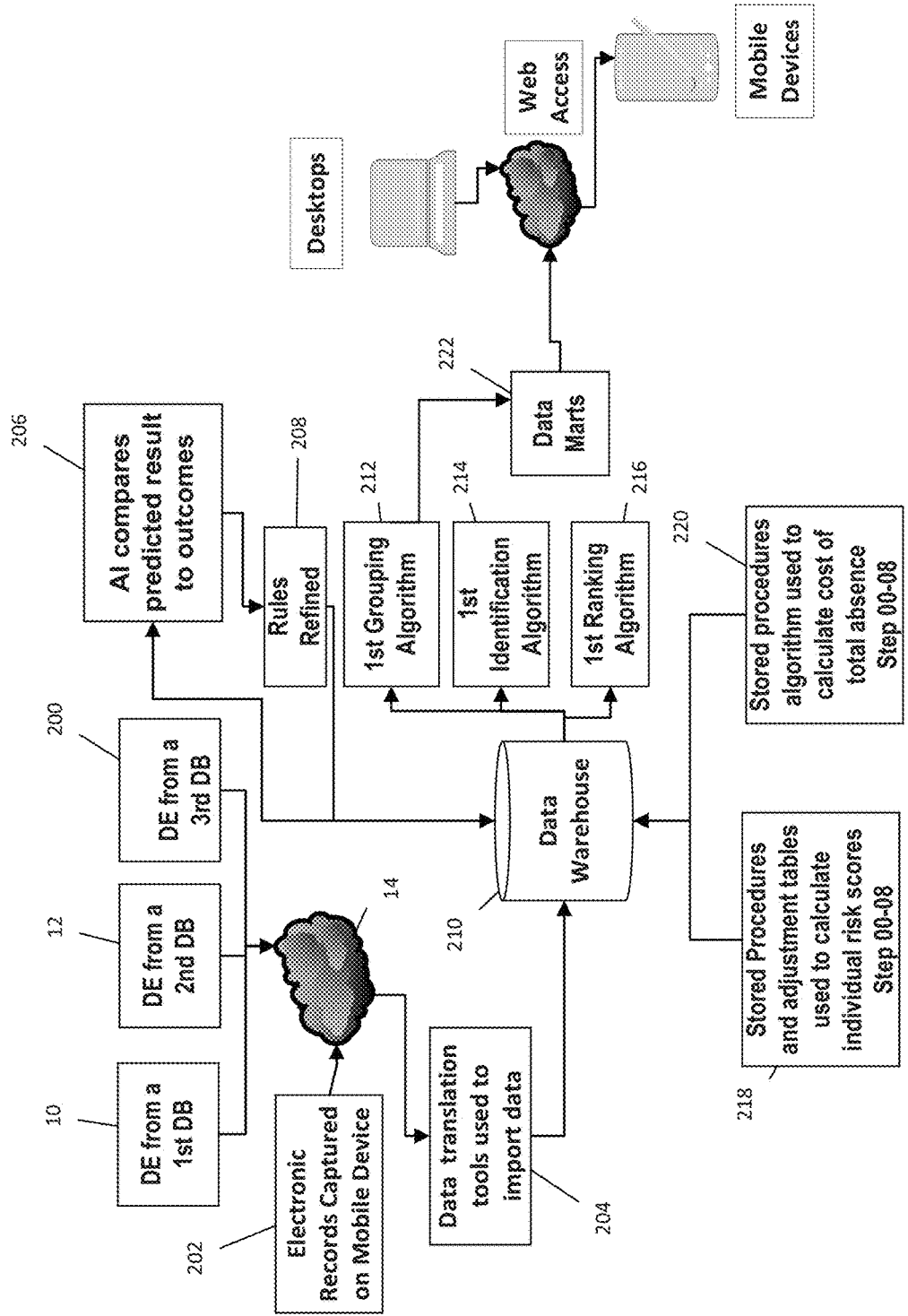
FIG. 2A shows a general process flow of an artificial intelligence (AI) system with details of data extracts for at least three specialized databases (DBs), transmission over the cloud, data translation importing to a central relational database, and a series of algorithms grouping, ranking, identifying then utilizing stored procedures for accomplishing specified tasks.

FIG. 2A continues the method described in a machine learning system from FIG. 1A and shows a general process flow of an artificial intelligence (AI) system with details of the data extract from the first database 10 (shown in FIG. 1A), a data extract from the second database 12 (shown in FIG. 1A), and a data extract for a third database 200. Along with data from the three databases (DBs), electronic records captured on an input or storage device are transmitted over secure communications network 14, to a data translation tool used to provide data in an appropriate format 204. From there, the formatted data is provided to a data warehouse 108. An artificial intelligence tool compares predicted results to outcomes utilizing predictive analytics 206, utilizing output from at least three specified databases including the data extract from a first database 10, the data extract from a second database 12, the data extract for a third database 200, and information provided by the data warehouse 210. The data warehouse 210, interfacing with a series of stored procedures (described with reference to FIG. 21 through FIG. 23D) and adjustment tables, calculate a third risk score 218. The stored procedures, interfacing with the data warehouse and the system, calculate a total cost 220. The total cost 220 is stored in the data warehouse 210. From there, a first grouping algorithm 212, a first ranking algorithm 214, and a first identifying algorithm 216 operate on data from the data warehouse 210 and provide the results to data marts 222.

Figure 2B:
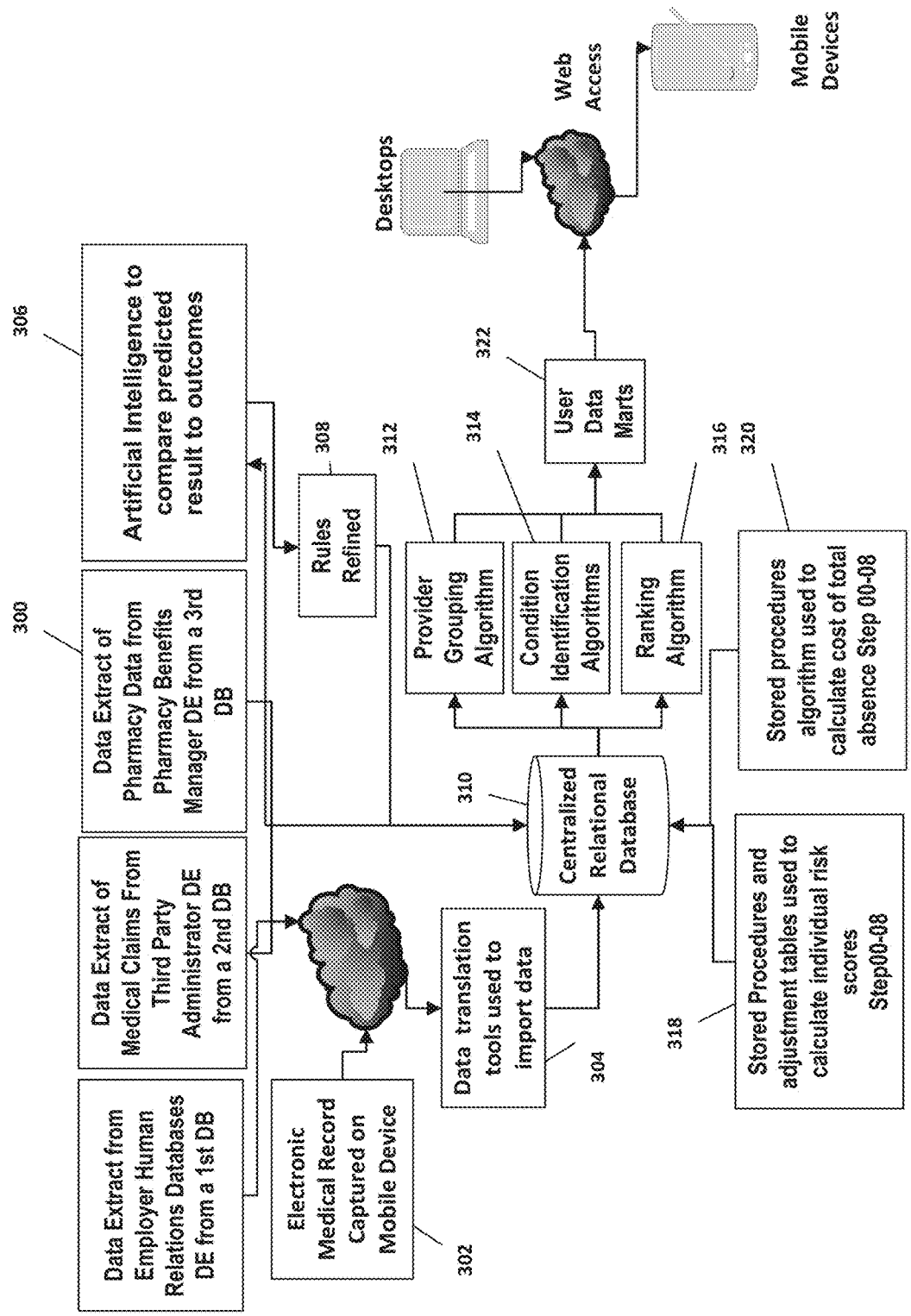
FIG. 2B shows a view of a general process flow demonstrating the interrelationship of a centralized database, stored procedures, rule refinement, ranking and provider participants with data extracts from at least three specified databases (DB), with the action of the artificial intelligence to compare algorithms-predicted results to outcomes in this healthcare embodiment.

FIG. 2B is a general process flowchart illustrating one embodiment of a healthcare artificial intelligence system in detail. Shown are a data extract from an employer's human resources database (i.e., a DE from a first DB) 100, a data extract from a third party administrator (TPA) medical claims database as a data extract from a second database (i.e., a DE from a second DB) 102, and a data extract of pharmacy data from a pharmacy benefits manager or management system as a third database (i.e., a DE from a third DB) 300. The foregoing data extracts, along with an electronic medical record captured on a mobile device 302 are communicated over secure communication network 14 to a data translation tool used to import data into the correct format 304. From there, data is transferred to a centralized relational database 310 within a data warehouse 108 (described with reference to FIG. 1B). An artificial intelligence (AI) tool 306 compares predicted results to outcomes utilizing predictive analytics. The predictive analytics applies rules through a matching, refinement and redefining of rules based on the artificial intelligence 308, with output from the at least three databases including the data extract from the employer human relations database 100, the data extract from a third party administrator (TPA) medical claims database 102, a data extract of pharmacy data from a pharmacy benefits manager or management system as a third database 300, and data provided by the centralized relational database 310. The centralized relational database 310 then applies the stored procedures (described with reference to FIGS. 21 through 23D) and adjustment tables used to calculate individual risk scores 318, with a stored procedure 320, that the artificial intelligence 306, of the centralized relational database 310, utilizes in calculating a cost of total absence 320. The calculations are stored in the centralized relational database 310, which passes data to a provider grouping algorithm 312, a condition identification algorithm 314, and a ranking algorithm 316, which then communicate the data to user data marts 322.

Figure 3A:
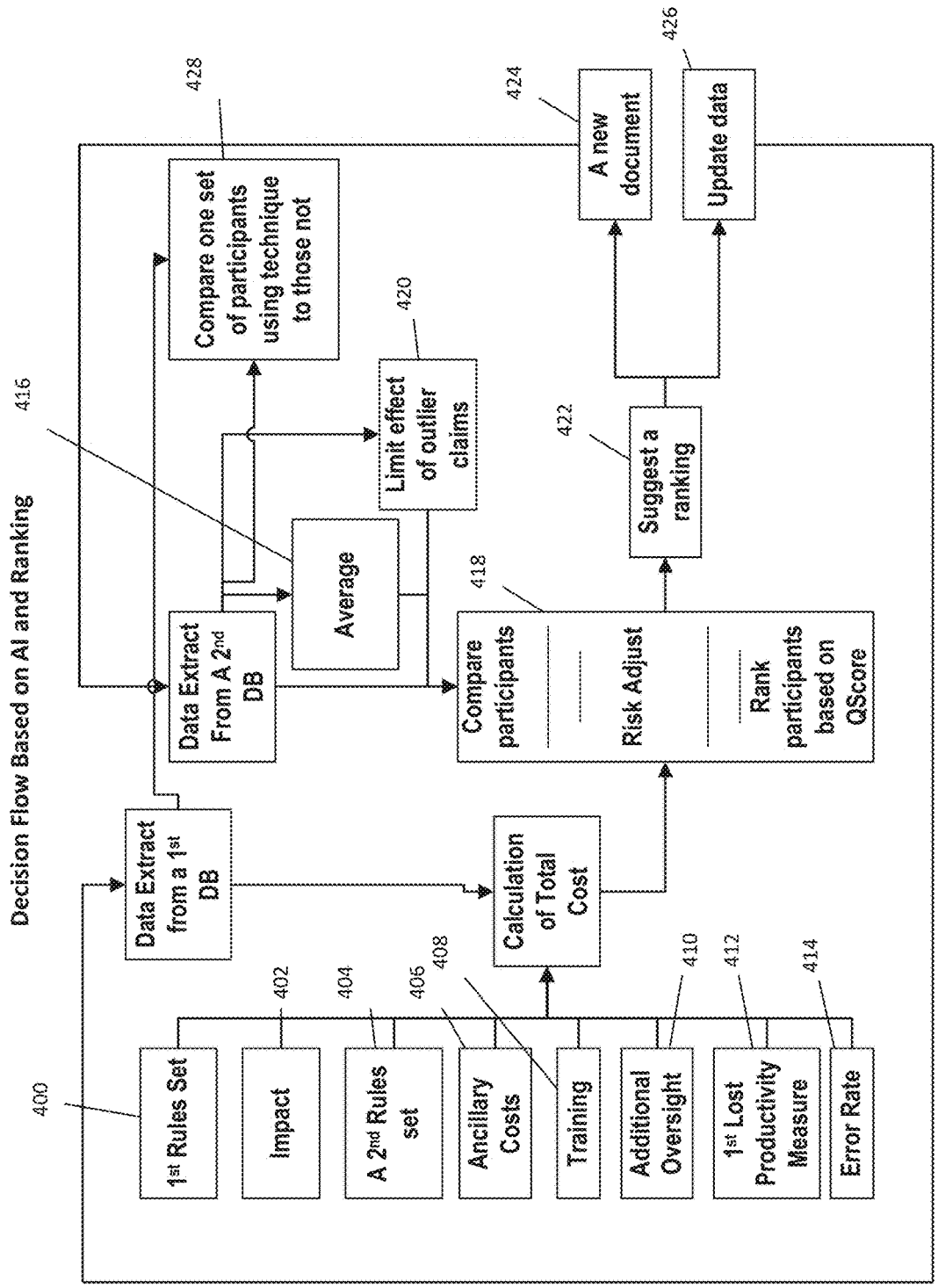
FIG. 3A depicts a decision flowchart based on artificial intelligence (AI) and ranking.

FIG. 3A is a decision flowchart based on artificial intelligence (AI) and ranking. As shown in FIG. 3A, a first rules set 400, impact data 402, a second rules set 404, ancillary costs 406, training 408, additional oversight 410, first lost productivity measure 412, and error rate 414 are utilized in a calculation of total cost engine 16 (described with reference to FIG. 1A) and then transmitted into a comparator engine of participants (providers) (e.g., the source of the data). The data is risk adjusted so that the participants (providers) are ranked based on a scoring (e.g., quality scoring) 418. Data from a first DB 10 (described with reference to FIG. 1A) is utilized in the calculation of total cost 16 (described with reference to FIG. 1A), all of which are combined to achieve the quality score 418. The data extract from a second DB 12 (described with reference to FIG. 1A) transfers data directly into the quality score 418, and data from the data extract from the third party administrator (TPA) medical claims database as a data extract from a second database 102 provides data for a comparator engine 428. Comparator engine 428 compares one set of participants (e.g., providers) who use the technique to those who do not. Data is then transferred to the data extract from a second DB 12 (described with reference to FIG. 1A), through an averaging device 416, and then back to the quality scoring 418. In the alternative, the data extract from a second DB may send information from comparator engine 428 directly back into 418, bypassing 416 altogether. Then data fed into to the comparator engine 428 from data extract of a second DB 12 (described with reference to FIG. 1A) also feeds data to a limiting engine 420 which limits the effect of outlier claims. Data coming out of 418 is fed into a ranking engine 422 where rankings are suggested based on the available data, which can be used to create a new document 424, update data 426, or both together.

Figure 3B:
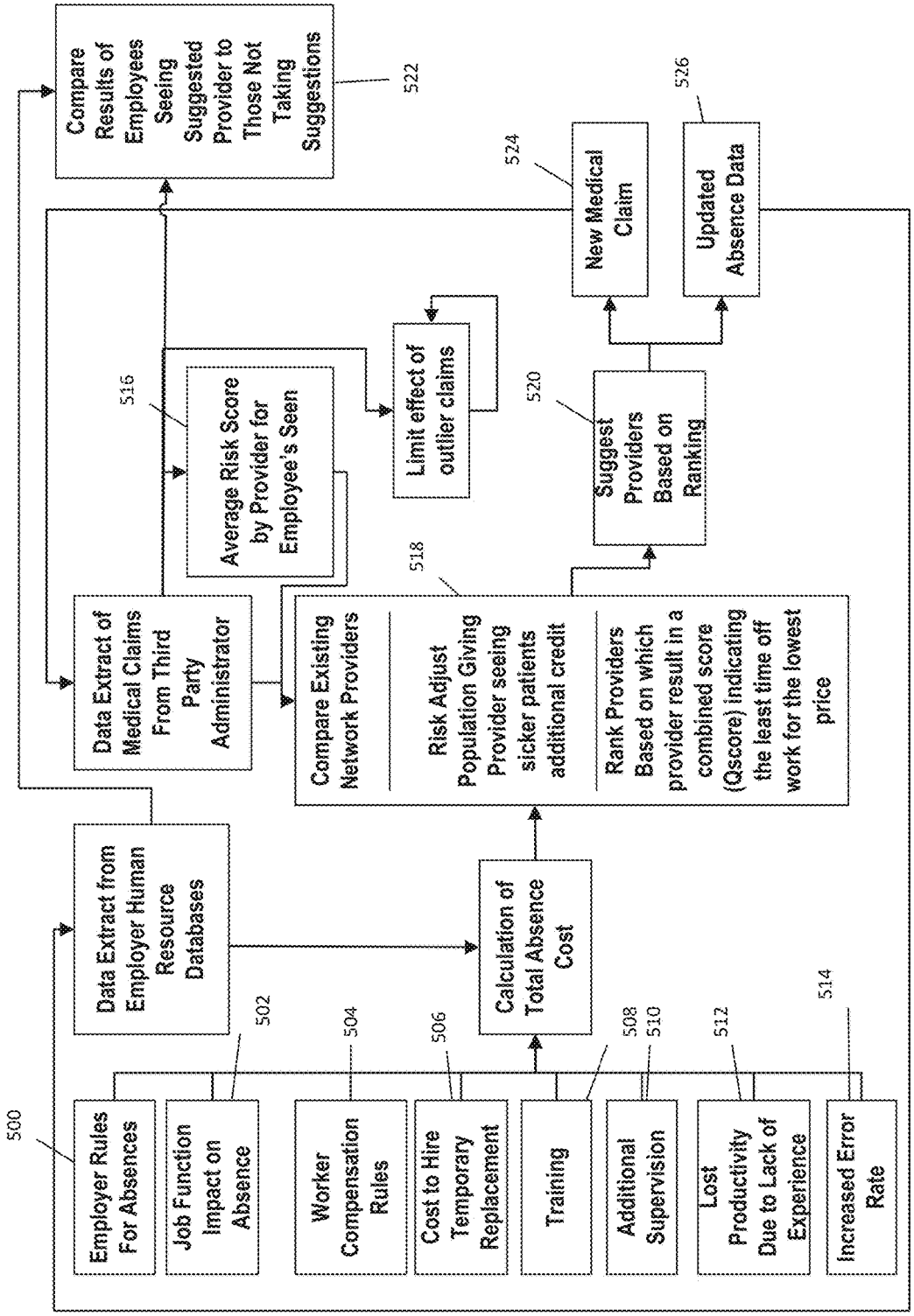
FIG. 3B depicts a decision flow based on a healthcare embodiment.

FIG. 3B is a decision flowchart based on an embodiment in a healthcare scenario. A series of rules inputs comprise employer rules for absence of an employee from work whether by absence or paid time off (PTO) 500, the job function impact on absence 502 (i.e., what impact the employee's job function has on the business when the employee is away from work either through illness of accident), worker compensation rules 504, the cost to hire a temporary replacement 506, the need for training of any replacement 508 (including what standards and level of work are required and the associated costs), what additional supervision costs may be required 510, expectation for the lost productivity due to a lack of experience of the temporary replacement 512, and any increased error rates 514 due to a new hire. All of these costs are fed into a calculation of total cost 108 (discussed with reference to FIG. 1B), plus data extracts from one of at least two databases (e.g., the data extract from the employer human resource database 100 and the data extract from the TPA database 102). The calculation of total absence cost from 104 (discussed with reference to FIG. 1B) interfaces directly into an engine that compares existing network providers then applies the algorithm to risk adjust a population, thereby giving a provider seeing sicker patients additional credit in the calculation. Providers are ranked based on QScore 518 (indicating which providers prepare employees to go back to work the fastest with the least cost at their highest productivity). Data extract of medical claims from third party administration (TPA) is averaged 516, with constrained outliers for comparison. A comparator engine compares results of employees seeing a suggested provider to those not taking the suggestion 522. Provider rankings based on QScore are provided to an engine that suggests providers based on ranking 520, which generates new medical claims 524 as an output or updates absence data 526, or both.

Figure 4A:
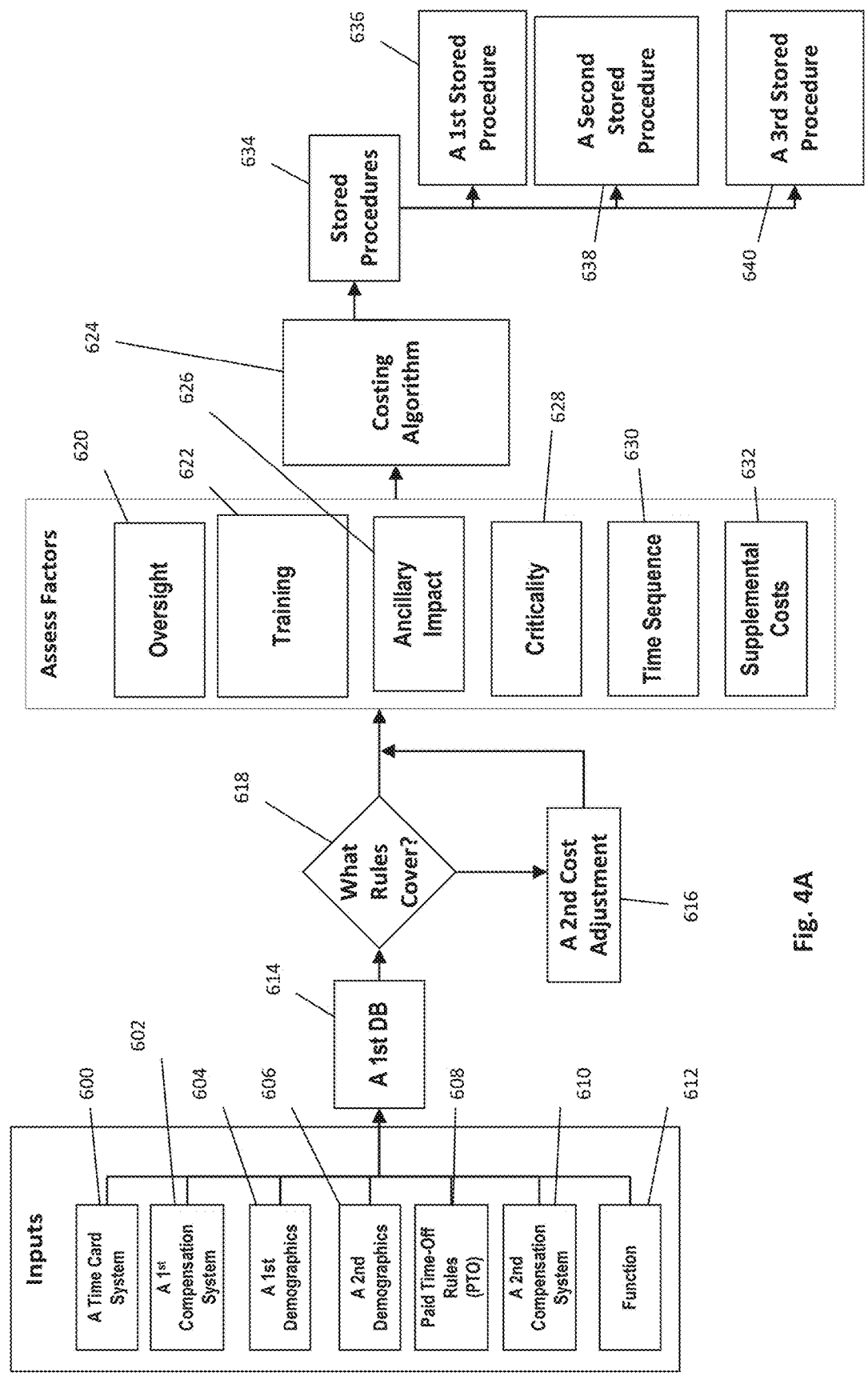
FIG. 4A depicts a data collection process used to calculate a first basis cost.

FIG. 4A describes data collection used to calculate a first basis cost. A first database (DB) 614 receives inputs from a time card system creating a time sequence of events 600; a first compensation system 602 which presents costs to the system, since expenses and costs are important to quality; a first demographics input 604; and a second demographics input 606; PTO rules 608, which along with the time card system in 600 provide a basis for calculating costs over time; a second compensation system 610, which along with first compensation system 602 provide a basis for the costing algorithms based on a participant's pay; and the function 612, in which the participant determines the level of compensation (a first compensation system 602 and a second compensation system 610), affected by the time sequence. In first database (DB) 614, decision pathways determine the rules 618 and a cost calculation is adjusted 616. Factors used to assess the calculation are applied and they can be any number of different inputs. Disclosed herein are oversight 620, training 622, ancillary impact 626, and criticality 628, in which the data created by the system from the inputs is assessed. The time sequencing of events 630 occurs based on the parameters and constraints in the system that provide a commencement of an event and the ending of an event, and other costs are considered as supplemental costs 632. All of the assessment factors applied to the inputs are input into a costing algorithm 624. That information, based on a stored procedure call of all the stored procedures 634 (e.g., step 00 run process, step 01 creates tables, step 02 populates data in the database, step 03 creates dictionaries, step 04 creates a fact table for use in OLAP cubes generation for use in advanced multi-threaded, multidimensional reporting, step 05 HCCScore contains information on the HCC Score system and is used to backfill the PTO_Saver Database (PTO), step 06 CDPS Score, step 07 a series of at least three logic rules, and step 08 QScore), feeds into a stored procedure Step 03 636, another series of stored procedure steps (02, 04, 07) 638, and an additional stored procedure step (02, 03) 640.

Figure 4B:
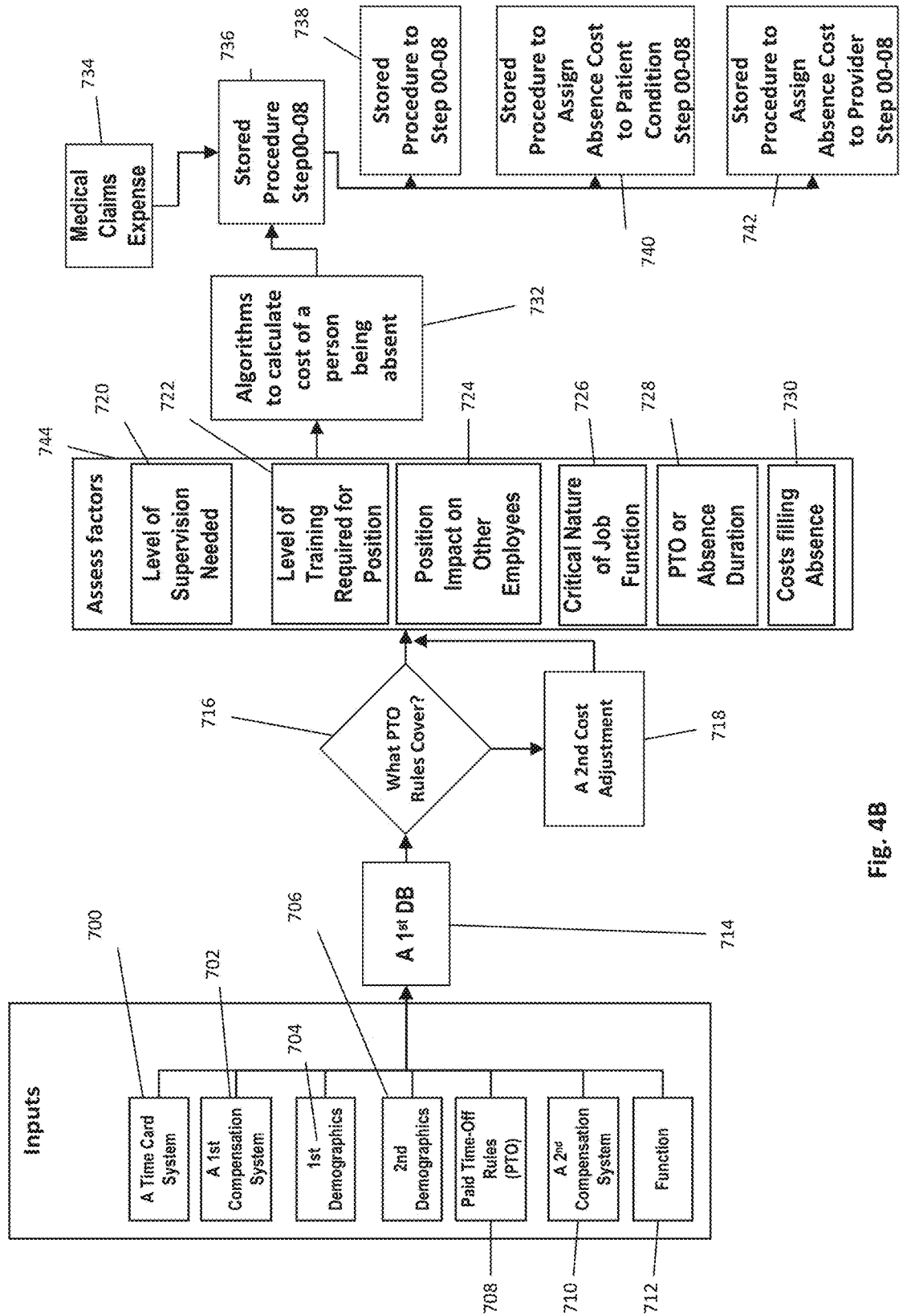
FIG. 4B depicts a data collection process used to calculate an absence expense.

FIG. 4B is an overview of a data collection and extraction system and calculation of absence expense with risk adjustment for an employer utilizing stored procedures in a healthcare scenario. Inputs comprise an employer's time card system 700, an employer's workers' compensation system 702, employee demographics 704, dependent demographics 706, paid time off rules (PTO) 708, employee compensation 710, and employee job function 712 (which are inputs that provide the proper framework for analyzing a total cost of an employee absent from work attributable either to injury or illness). These inputs are processed through an employer human resource database that has been replicated into the system through a stored procedure utilizing a particular schema 714. A decision pathway 716 is called that asks if the absence is covered by paid time off. If the answer is yes, then that answer is transferred to assess factors. If the answer is no, then there is a cost adjustment 718. The answer is then transferred into an assess factors container 744. Assess factors container 744 looks to addressing factors that affect the costing issue such as level of supervision 720, level of training required for the position 722 (which is often used to determine how much training new hire must receive), what is the impact of an absent employee in that position on other employees 724, what is the critical nature of a particular job function to total absence cost and expense 726, what is length of absence 728, and any other costs to fill the absence position with a temporary hire 730. Data from assess factors 744 is processed through algorithms to calculate a cost of a person being absent utilizing the inputs and assess factors 744. This data is processed through the stored procedures 736, based on the nature of previous answers to questions provided by the artificial intelligence learning system adapting to these changes during the course of analyzing data, so any of a number of stored procedures 736, from Step 00-Step 08, can be utilized. Additional procedures almost always come into play. As shown in FIG. 4B, these are stored procedures 00-08 and in particular step 03 738. Next is stored procedure to assign absence cost to a patient (employee) condition as may be found in steps 02, 04, and 07 740. Additionally, a series of stored procedures is utilized to assign absence cost to a provider as through steps 02 and 03 742.

Figure 5A:
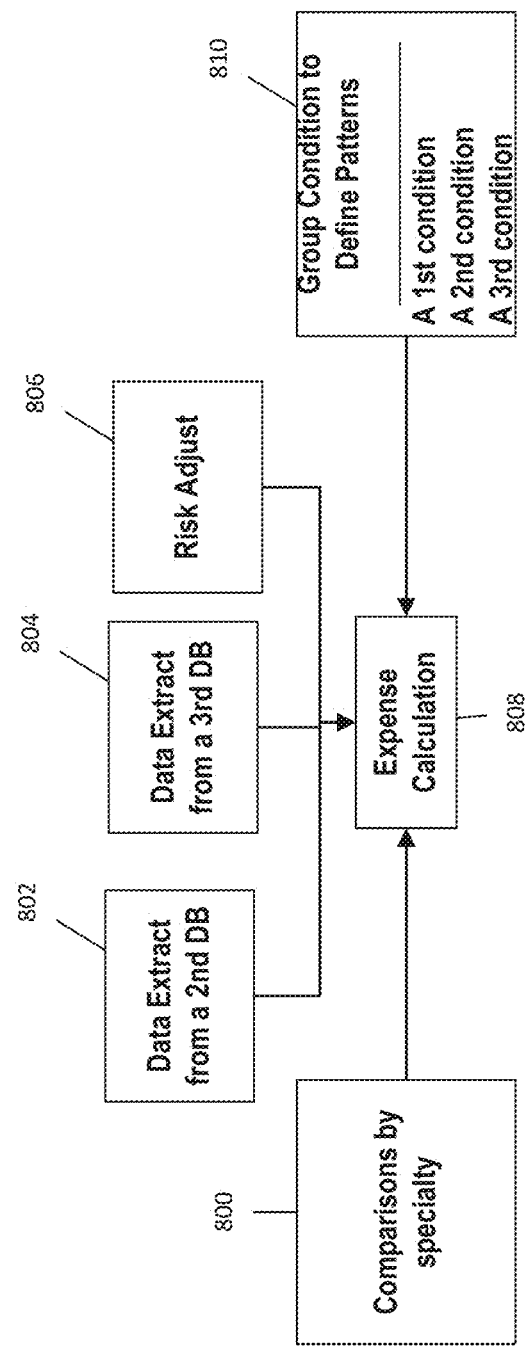
FIG. 5A depicts how an expense calculation is derived from algorithm defining rules and the totals being risk adjusted by conditions impacting the risk adjusted data.

FIG. 5A describes how an expense (cost) calculation 808 is derived from an algorithm defining rules and the totals being risk adjusted by conditions impacting the risk adjusted data. Algorithm rules and risk adjustment comparisons by specialty 800 feed data to an expense calculation engine 808. And extracts from at least two databases (i.e., a data extract from a second database (DB) 802 and data extract from a third database DB 804) and a risk adjustment 806 are fed to the expense calculation engine 808. Conditions are grouped to define patterns 810, including a first condition, a second condition, and a third condition to feed into the expense (cost) calculation 808.

Figure 5B:
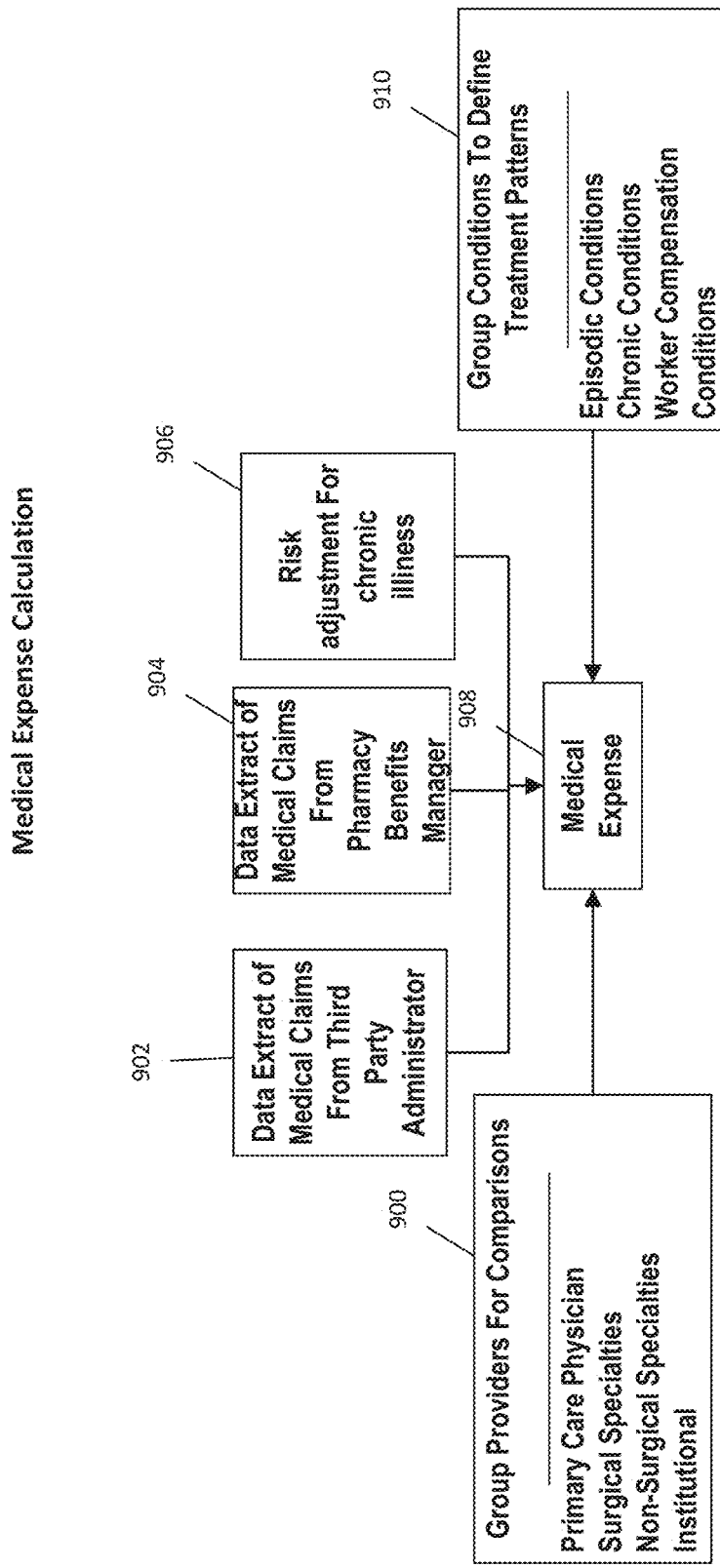
FIG. 5B is an overview of a medical expense calculation combined with a risk adjustment for chronic, episodic and worker's compensation.

FIG. 5B is an overview of a medical expense calculation utilizing data from at least two databases, wherein a data extract of medical claims from a third party administrator 902, a data extract of medical claims from a pharmacy benefits manager 904, and a risk adjustment for chronic illness 906 are fed into a medical expense calculator 908. Grouping providers for comparison into three of five potential groups of providers (e.g., primary care physicians (PCPs), surgical specialties, non-surgical specialties and institutional) 900 and a grouping of conditions to define treatment patterns (such as episodic conditions, chronic conditions, and worker's compensation conditions) 910 are fed into medical expense calculation engine 908.

Figure 6A:
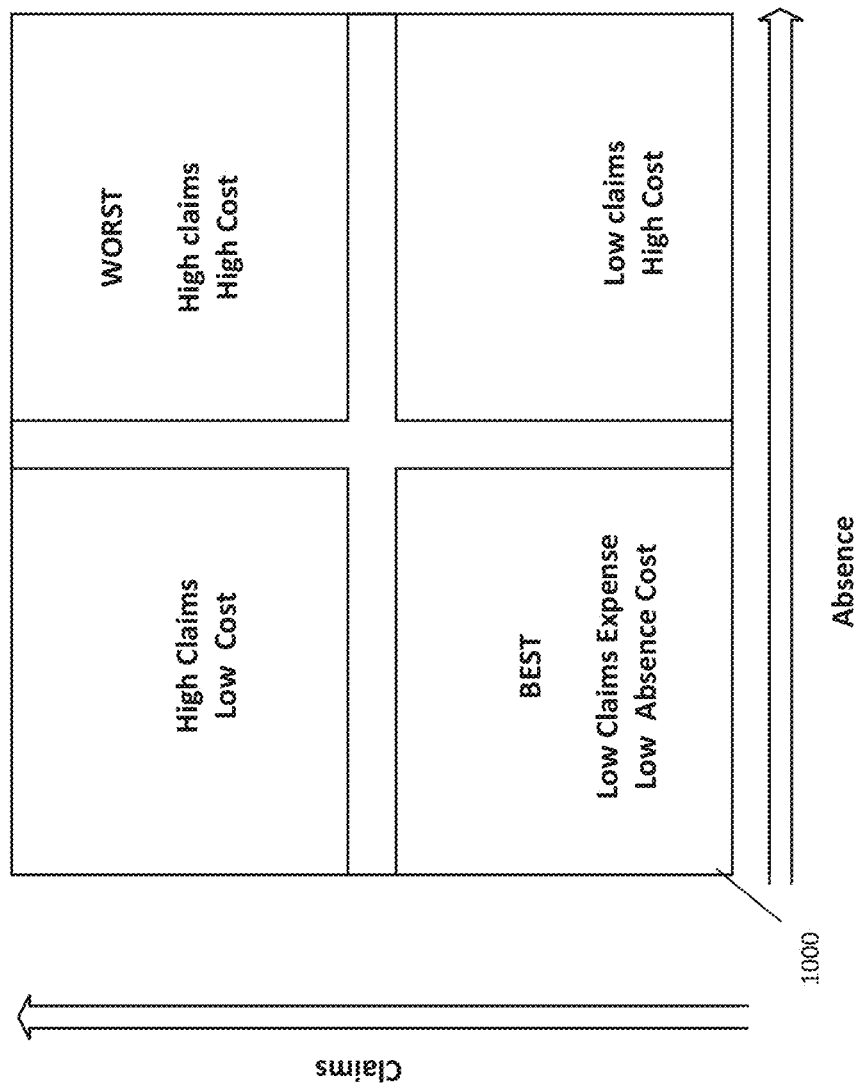
FIG. 6A depicts a rules engine and its considerations in defining a best outcomes comparison.
Figure 6B:
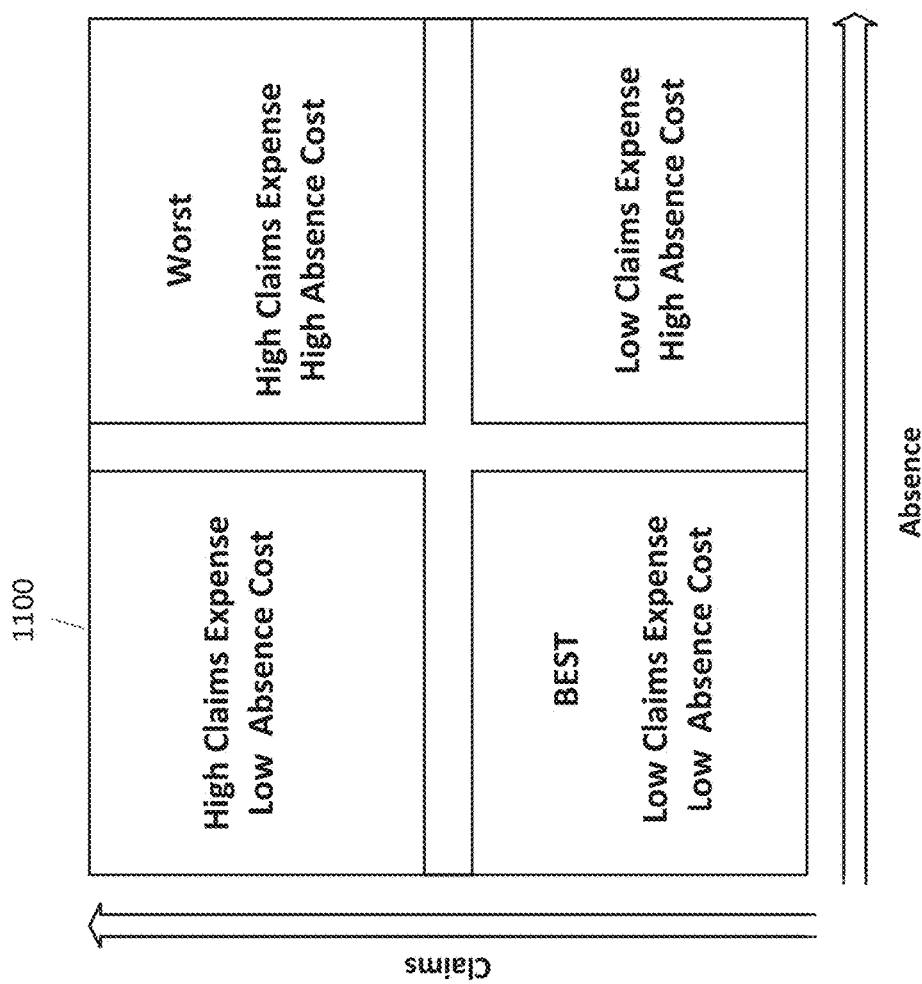
FIG. 6B depicts a total absence expense quadrant defining scenarios based on a best outcomes result with the lowest cost to achieve a specific best outcome.

FIG. 6A describes further rules that compare best outcomes. The rules engine addresses constraints that define a best outcome in a comparison of claims versus absences 1000. FIG. 6B is a total absence expense quadrant 1100 that defines scenarios based on a best outcomes result with the lowest cost 1104 to achieve a specific best outcome based on the scenario. In a first scenario, a provider produces the lowest claims expense, but the patient has a higher total absence cost. In a second scenario, a provider produces a lower total absence cost, but has a higher claims expense. The best outcome is reflected by the lowest absence cost and the lowest medical claims expense. The outcome depends on the individual circumstances. The system can then determine "best practices" for each diagnosis by evaluating the medical and pharmacy claims of the best providers for that diagnosis (lowest claims expense combined with lowest absence expense) to determine the procedures and treatment patterns that they use to get those best results as compared to the procedures and treatment patterns of the other providers.

Figure 7A:
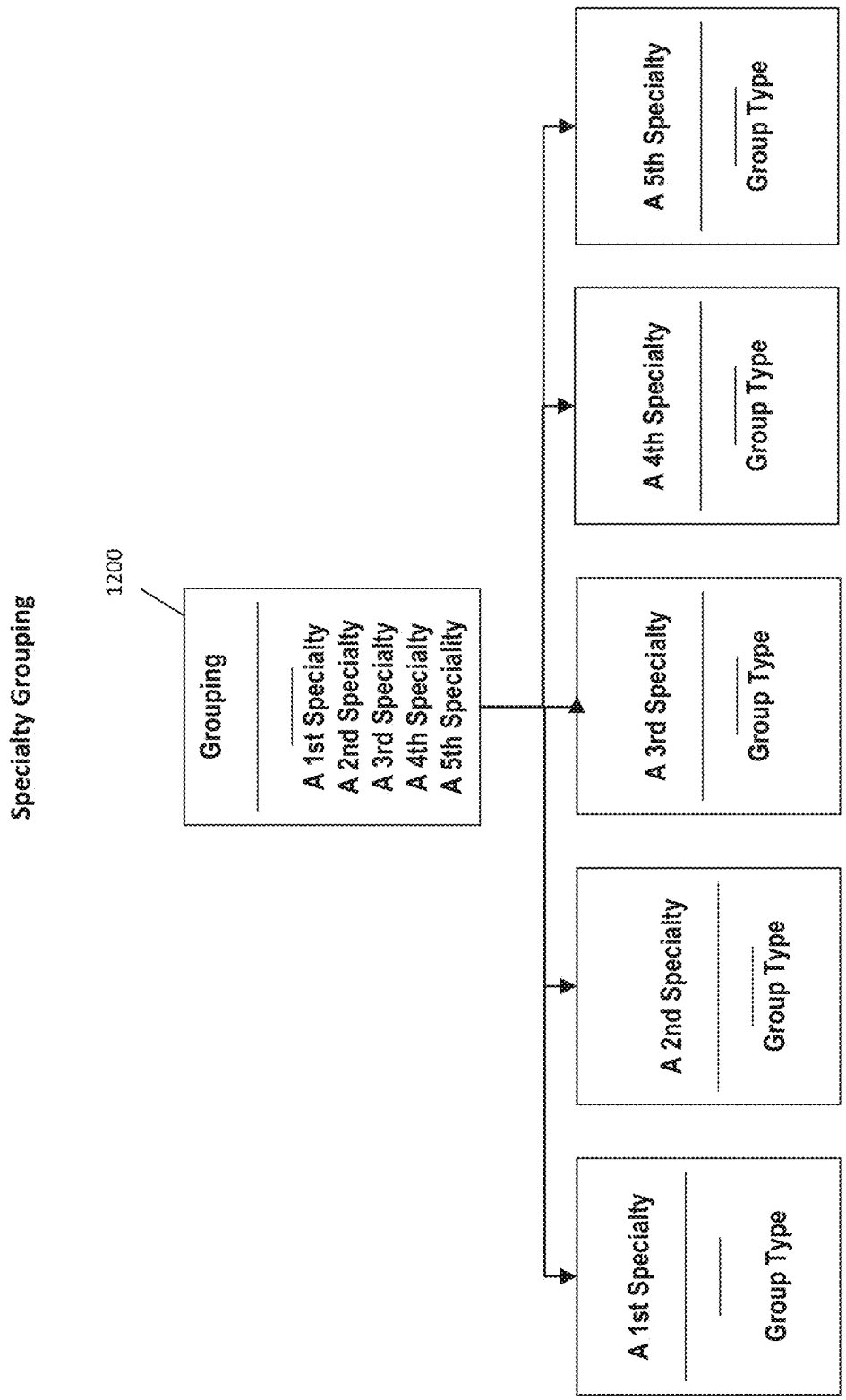
FIG. 7A depicts a specialty grouping based on a series of types of specialties.

FIG. 7A further describes a specialty grouping 1200, utilizing the grouping algorithm groups of specific specialties assembling based on a series of types of specialties. FIG. 7B provides an overview of various provider groupings 1300, including for example by specialty 1302. When comparing total absence expense (cost), a primary care physician should not be compared to a facility or surgeon. Therefore, providers are grouped into categories based on the types of services performed.

Figure 8A:
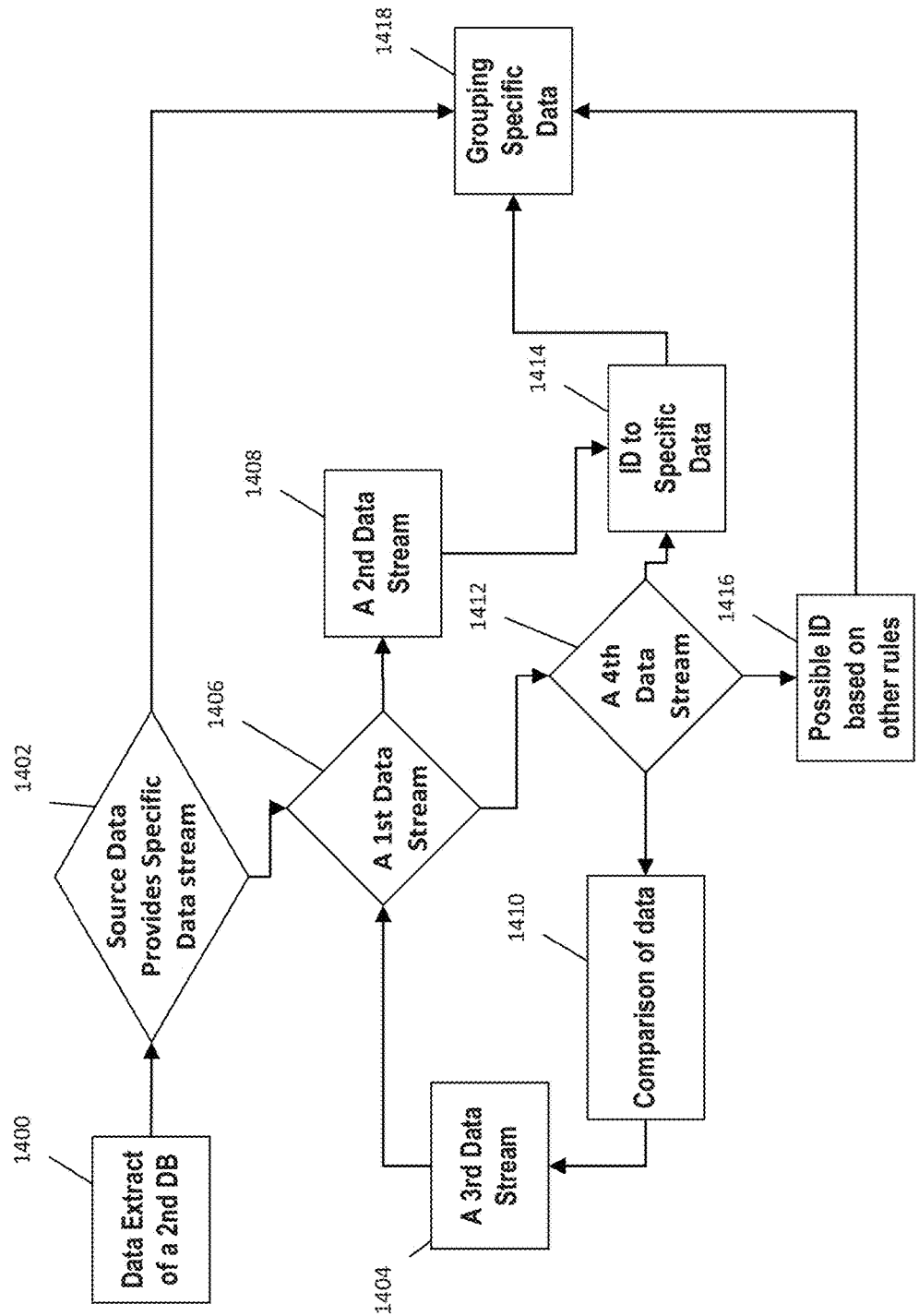
FIG. 8A depicts a grouping decision process flow and data input diagram describing the input of a data extract of a second database as source data for specific streams of provider data including a comparison for identification of specialties.

FIG. 8A depicts a grouping decision process flow and data input diagram describing input of a data extract of a second database 1400 as source data for specific streams of data 1402. The source data is input to a first data stream 1406 and a grouping algorithm that groups the specific inputted data 1418. A second data stream 1408 receives data from first data stream 1406 and sends data to a function that identifies specific data 1414. The first data stream 1406 sends data to a fourth data stream 1412. The fourth data stream 1412 sends data to identification (e.g., ID) 1414 to identify specific data. A possible ID based on a second set of rules (other rules) 1414 receives data from 1412 and sends its data to a grouping algorithm 1418, which groups specific data. A third data stream receives data from a comparator 1410 and sends data to first data stream 1406, through either a third data stream 1404, or through a fourth data stream 1412.

Figure 8B:
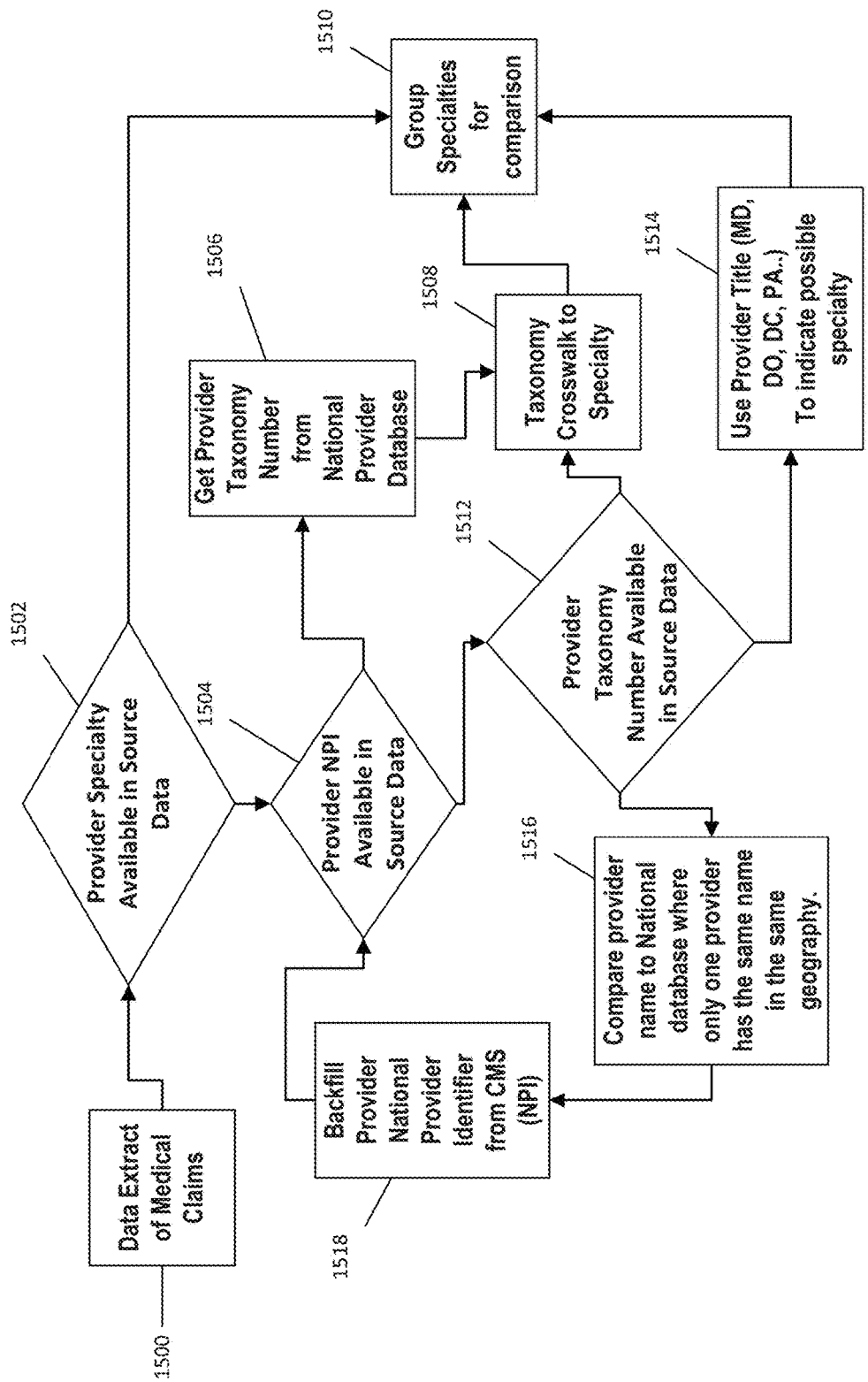
FIG. 8B depicts a provider grouping process. An input of a second data extract of medical claims and data regarding the providers who provided the care are used to compare providers based on categories and types of services performed. Provider data includes a first provider data, a second provider data, a third provider data, and a fourth provider data with a comparison for identification of specialties. When comparing total absence expense, a primary care physician should not be compared with a surgeon or a facility, so providers are grouped into categories in accordance with the types of services performed.

FIG. 8B depicts a provider grouping process that receives an input of a data extract of medical claims (which includes from FIG. 5B medical claims from a third party administrator (TPA) and pharmacy benefits claims as a combined data extract) 1500. That data is transferred to a provider specialty that is available in the source data 1502. The provider specialty 1502 transfers its data to a grouping algorithm that groups specialties of providers for comparison 1510. The grouping algorithm 1510 also receives data from a taxonomy crosswalk to a specialty 1508, and also receives data from a use provider title (MD-medical doctor, DO-doctor of osteopathy, DC, PA, etc. . . . ) to indicate a possible specialty from the provider's title 1514. Provider taxonomy number available in source data 1512 sends data to use provider title 1514. The taxonomy crosswalk to a specialty 1508, and 1512, send data to a provider comparator 1516. The comparator compares provider names to national databases where only one provider has the same name in the same geography 1516. A backfill of a provider through access to a national database as NPI (National Provider Identifier) from CMS 1518 then sends data on to an NPI provider database available in source data 1504.

Figure 9A:
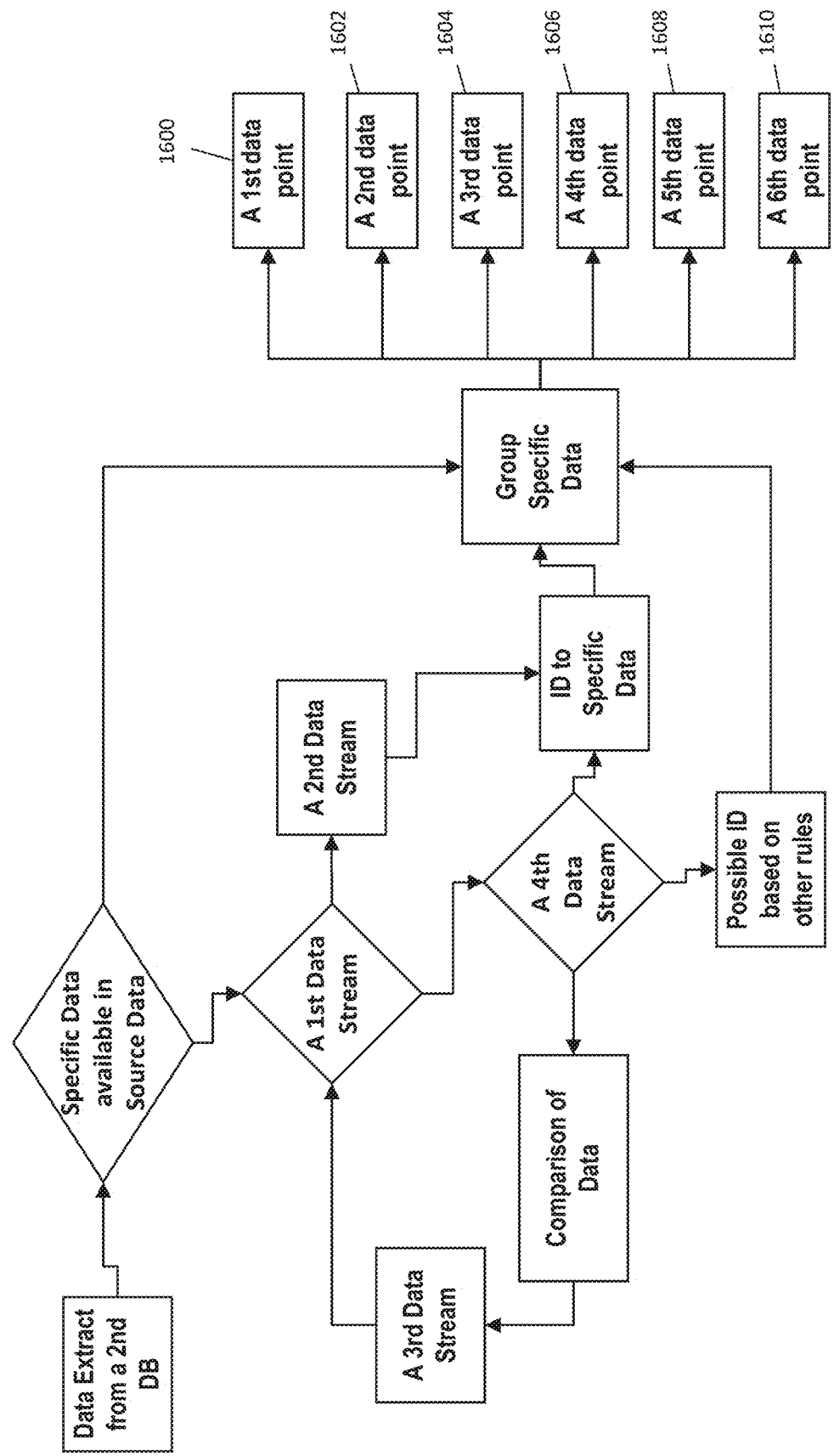
FIG. 9A depicts grouping process details for identification of specific data points.

FIG. 9A shows grouping process details for a machine learning application for identification of specific data points. FIG. 9A depicts the uses of six data points, including a first data point 1600, a second data point 1602, a third data point 1604, a fourth data point 1606, a fifth data point 1608, and a sixth data point 1610, which receive from the grouping algorithm specific data that allows the data points to address the data routed to specific databases.

Figure 9B:
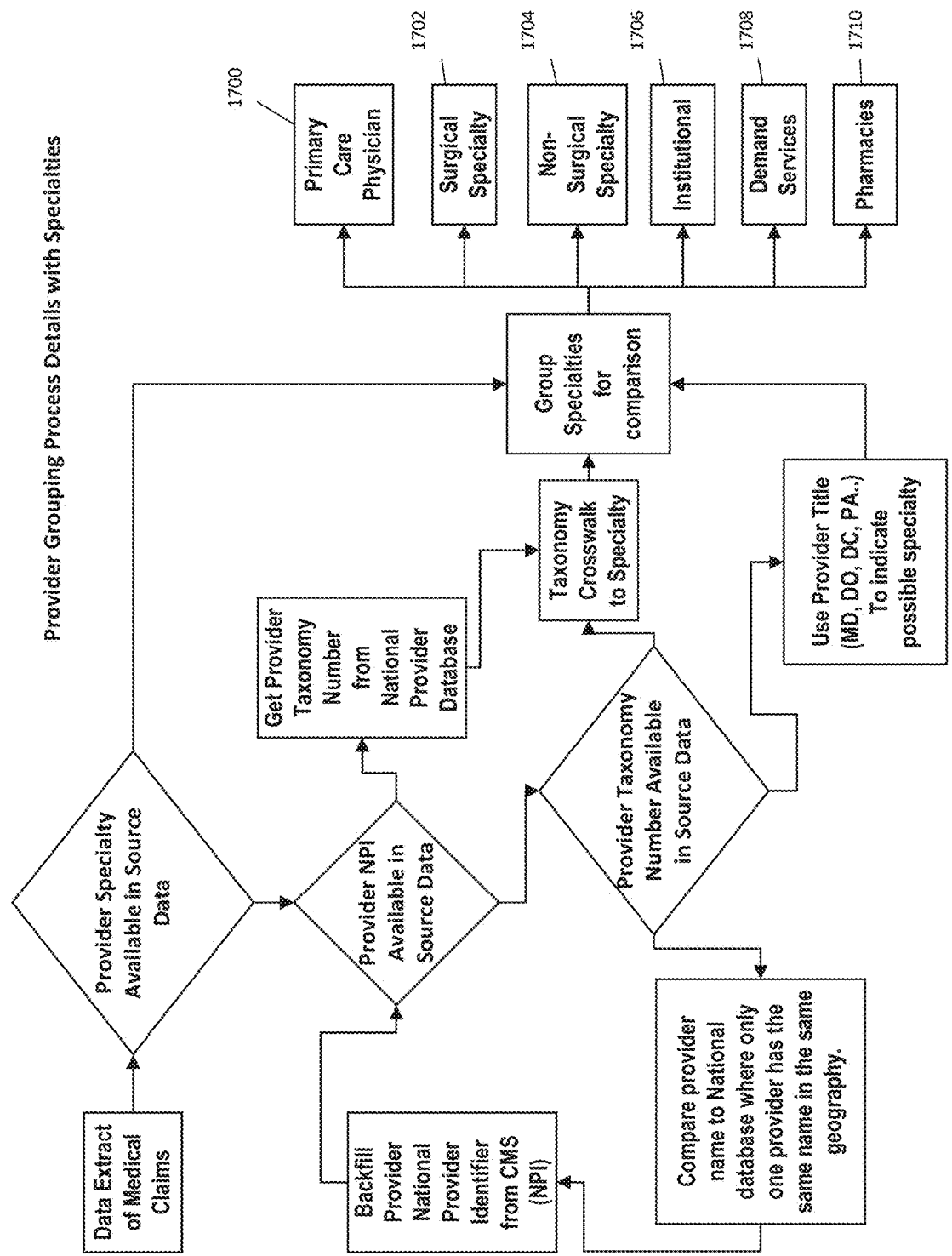
FIG. 9B depicts provider grouping process details with group specialties showing how the group specialties are determined from the provider grouping process.

FIG. 9B shows grouping process details and relates to specialties and the different types of specialties that help to prevent providers with widely differing practices from being compared without adjusting the practice of a provider based on the type of provider and the provider's specific capabilities. Shown are a primary care physician (PCP) 1700, a surgical specialty 1702, a non-surgical specialty 1704, an institutional provider 1706, demand services 1708, and pharmacies 1710.

Figure 10A:
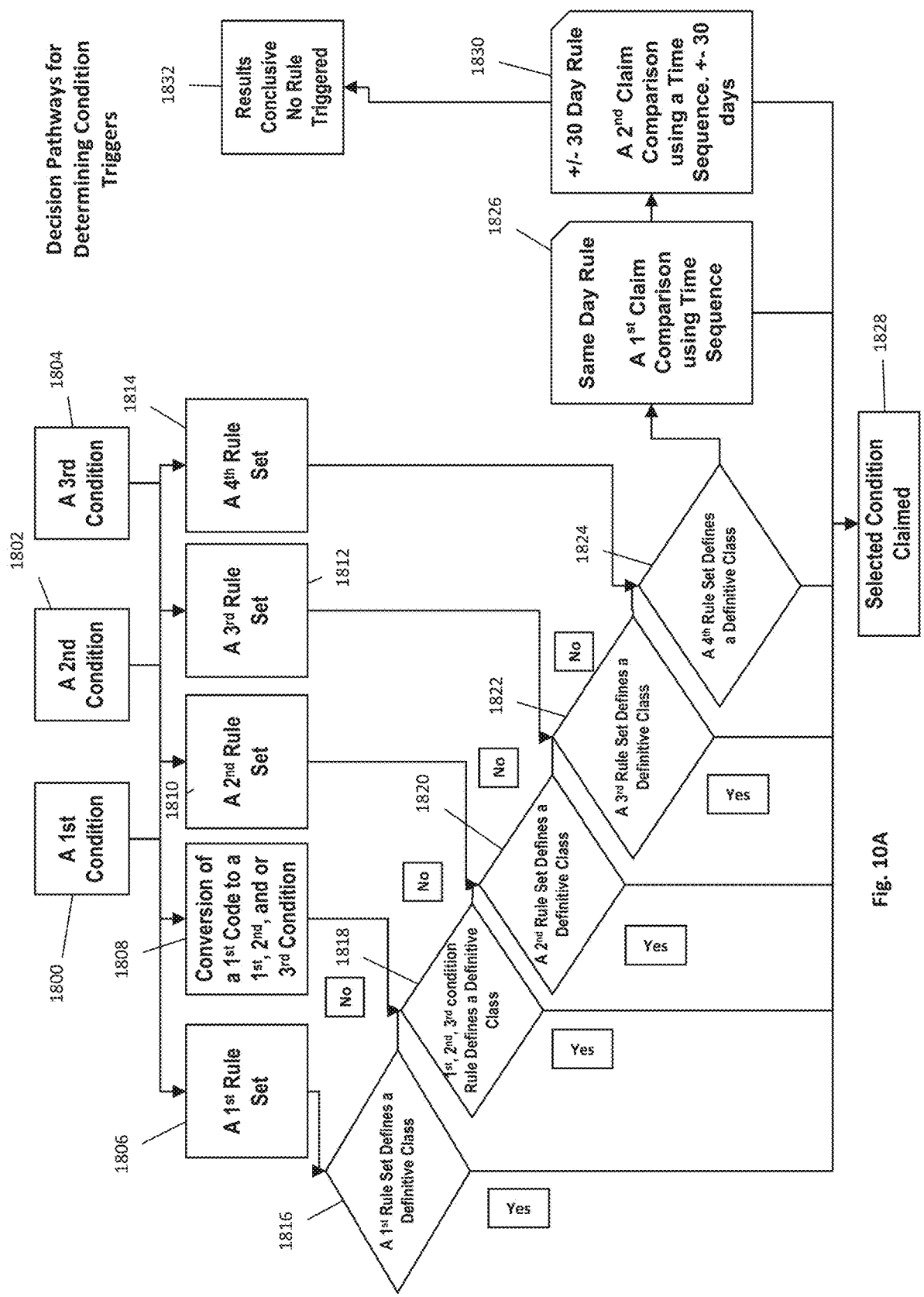
FIG. 10A depicts decision pathways for determining condition triggers.

FIG. 10A describes decision pathways for determining condition triggers. A first condition 1800, and a second condition 1802, and a third condition 1804 transfer data to a first rule set 1806; a converter which converts a first code to a first, second and/or third condition rule 1808; a second rule set 1810; a third rule set 1812; and a fourth rule set 1814. If the first rule set 1806 defines a first definitive class 1816, the decision pathway of yes inputs a selected condition claimed 1828. No as a response inputs into the next process step 1818. In decision block 1818, if the first, second, third condition rule defines a first, second, third definitive class, the answer travels along the decision pathway of yes to the selected condition claimed 1828. If not, the data feeds into a second rule set which defines a second definitive class 1820. If the answer is yes, then 1820 sends data from 1818 into 1828. If 1820 is no, then the data is sent into a third rule set that defines a third definitive class 1822. Decision block 1822 asks if a third rule set defines a third definitive class. If yes, then 1822 sends data to 1828. If no, then 1822 sends data to a fourth rule set which defines a fourth definitive class 1824. If yes for 1824, then data is sent from 1824 to 1828. If not, then 1824 sends data to same day rule 1826, where a first comparison using time sequence is performed. If the result is yes, then the data proceeds to 1828, whereas if the same day rule is insufficient, then 1826 sends data to +/−30-day rule 1830. In 1830, a second comparison is made using a time sequence of +/−30 days. If the result is yes, then data is sent to 1828, and if the result is no then results are conclusive and no rule is triggered, no condition is triggered, and no condition is selected as shown in 1832.

Figure 10B:
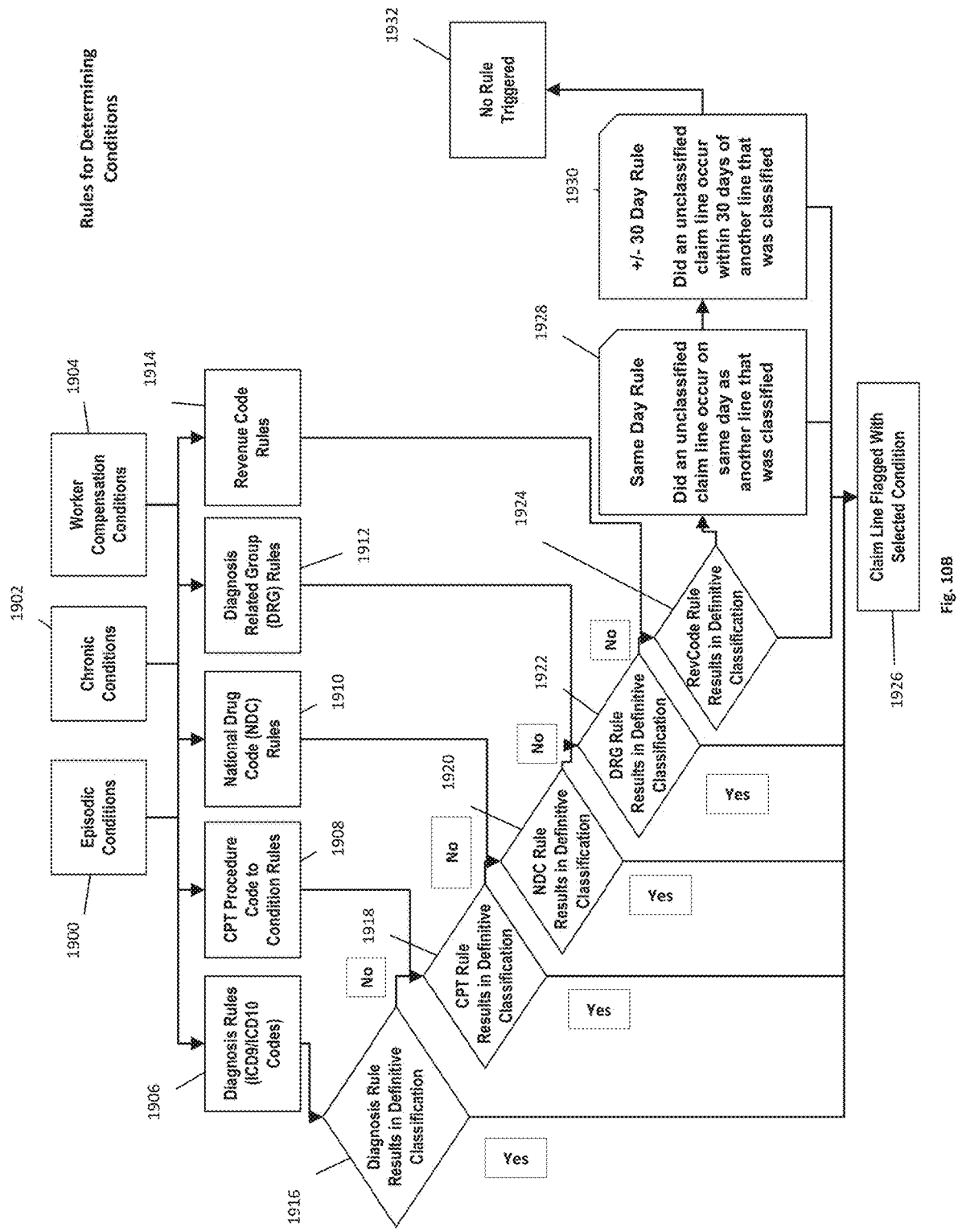
FIG. 10B depicts an overview of the rules for determining conditions, with the diagnosis revenue code (revcode) identifying claims with a particular condition.

FIG. 10B is an overview of the rules for determining conditions. The medical expense calculation shown in FIG. 5B was used to group conditions to define treatment patterns 910. In FIG. 10B, various conditions are shown, such as episodic conditions 1900, chronic conditions 1902, and workers' compensation conditions 1904. These conditions send data to diagnosis rules (e.g., ICD9/ICD10 codes) 1906, Health care Common Procedure Coding System (HCPCS) has Current Procedural Terminology (CPT) procedure code to condition rules 1908, national drug code (NDC) rules 1910, diagnosis related group (e.g., DRG) rules 1912, and revenue code (e.g., revcode) rules 1914. Where diagnosis rules from 1906 result in definitive classification in 1916, data is sent to claim line flagged with selected condition 1926 and a condition is assigned. If the result in 1916 is no, then 1916 sends information to CPT rule 1918. If CPT rule 1918 results in a definitive class, then data from 1918 is transmitted to 1926. If not, then data is transmitted to NDC rule results in definitive classification 1920. If the result in block 1920 is yes, then data is provided to block 1926. If not, then data is provided to DRG rule results in definitive classification 1922. If the result in block 1922 is yes, then data is provided to block 1926. If not, then data is provided to Revcode Rule 1924, which checks if revcode results in definitive classification. If yes, then the data proceeds to block 1926. If not, then data proceeds to same day rule 1928, which asks if an unclassified claim line occurred on the same day as another line that was classified. If yes, then data proceeds to claim line flagged with selected condition 1926. If not, then data proceeds to +/−30-day rule 1930 (which asks if an unclassified claim line occurred within 30 days of another line that was classified. If yes, then data proceeds to 1926, and claim line is flagged with a selected condition. If not, then no rule is triggered in block 1932.

Figure 11A:
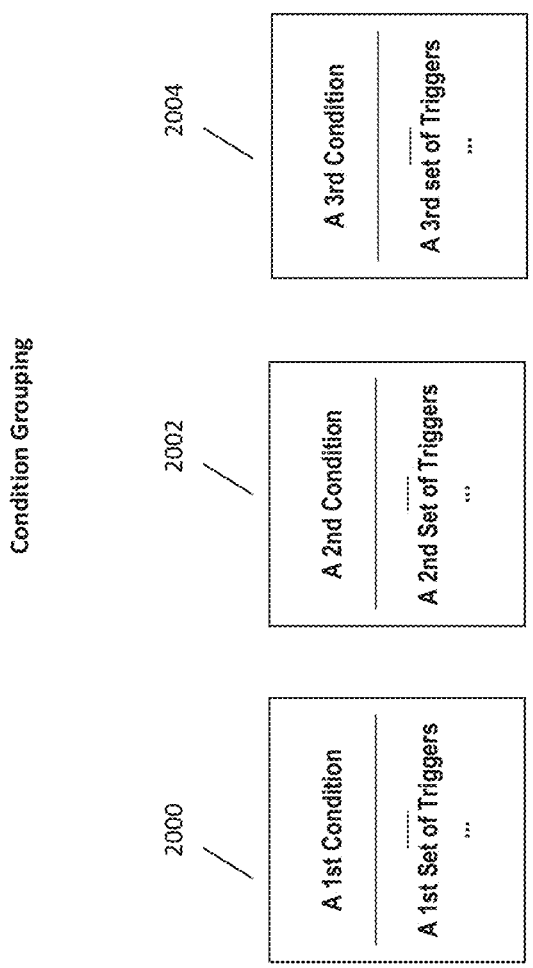
FIG. 11A depicts how a first condition yield is constrained by a first set of triggers; how a second condition yield is constrained by a second set of triggers; and how a third condition yield is constrained by a third set of triggers.
Figure 11B:
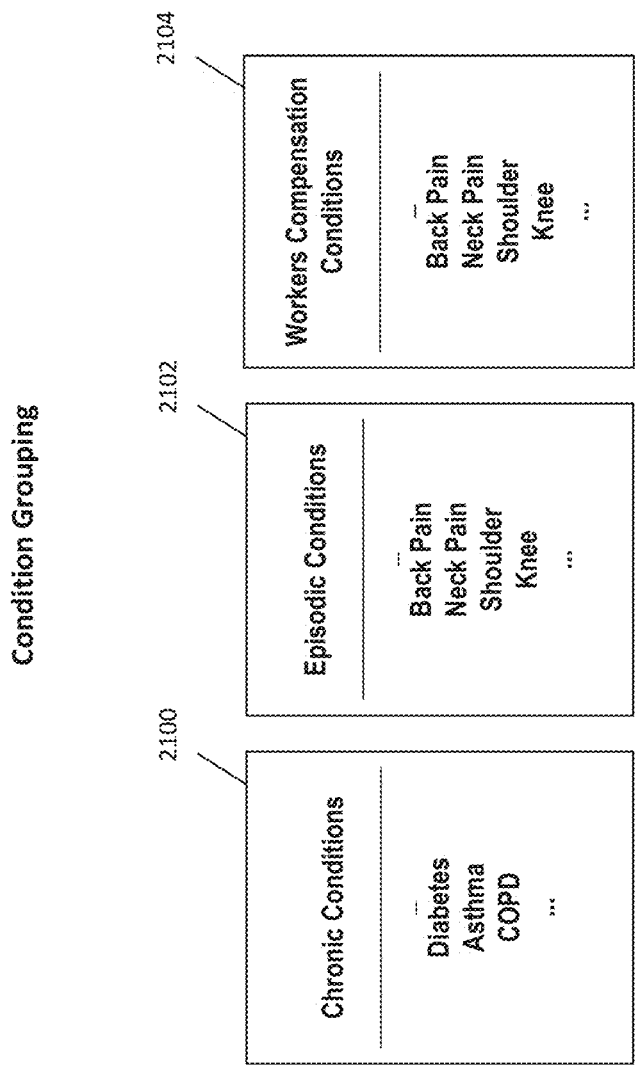
FIG. 11B depicts an overview of condition grouping based on a first condition.

FIG. 11A and FIG. 11B describe condition grouping with a first condition having a first set of triggers 2000, a second condition having a second set of triggers 2002, and a third condition having a third set of triggers 2004. In FIG. 11B, conditions are grouped according to episodic conditions, being those that are treatable conditions, such as neck pain, shoulder pain and back pain where recovery is possible 2100. Chronic conditions 2102 are, for example, diabetes, asthma, and COPD, and are long term conditions where the patient's (e.g., employee) condition can be managed but does not go away. Workers' compensation conditions 2104 are similar to episodic conditions 2100, but the absence of the employee from work is the result of a work injury, often an accident, and may also include sprains, fractures, and burns, and may also include a Covid-19 infection. Controlling the costs associated with these three conditions requires managing the total cost of absence. Accordingly, the rules used to define a condition should take into account where change can be effectuated. For example, effectuating change is not practical when the employee (e.g., patient) shows up in the emergency room with a sprained shoulder (episodic condition), the patient cannot feasibly be directed to the best provider. In that case, the sprained shoulder would be excluded from the rules set for an episodic condition. However, for a workers' compensation condition, a sprained shoulder would be included.

Figure 12:
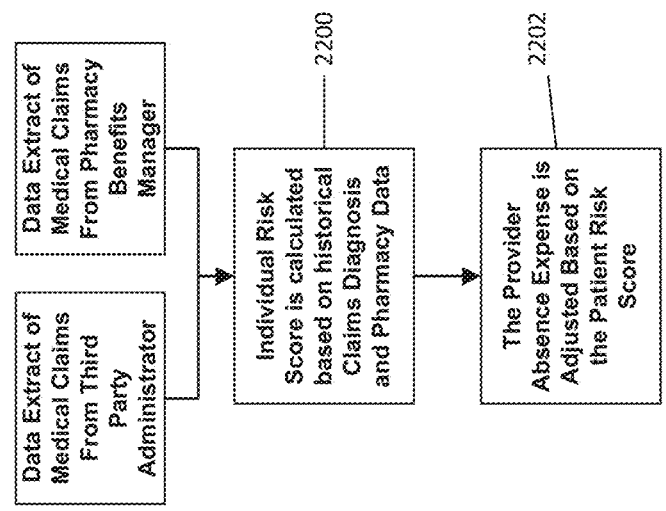
FIG. 12 depicts a population risk adjustment, in this case using an outside risk adjustment with data extracts from two databases.

Since an individual provider may see sicker patients than the provider's peers, the patient expenses should be adjusted to account for this. FIG. 12 is a population risk adjustment utilizing at least two of three specific data bases constraining the results to providers who may see sicker patients than their peers and adjusting for that possibility by including at least one of a plurality of industry standard risk adjustment systems (e.g., Medicare HCC, Medicaid CDPS, John Hopkins ACG). Data extracts of medical claims from a third party administrator (e.g., TPA) 102 and data extracts of medical claims from a pharmacy benefit manager 300 are combined into an individual risk score calculated based on historical claims diagnosis and pharmacy data 2200. The result is then combined into a provider absence expense that is adjusted based on a patient risk score 2202.

Figure 13:
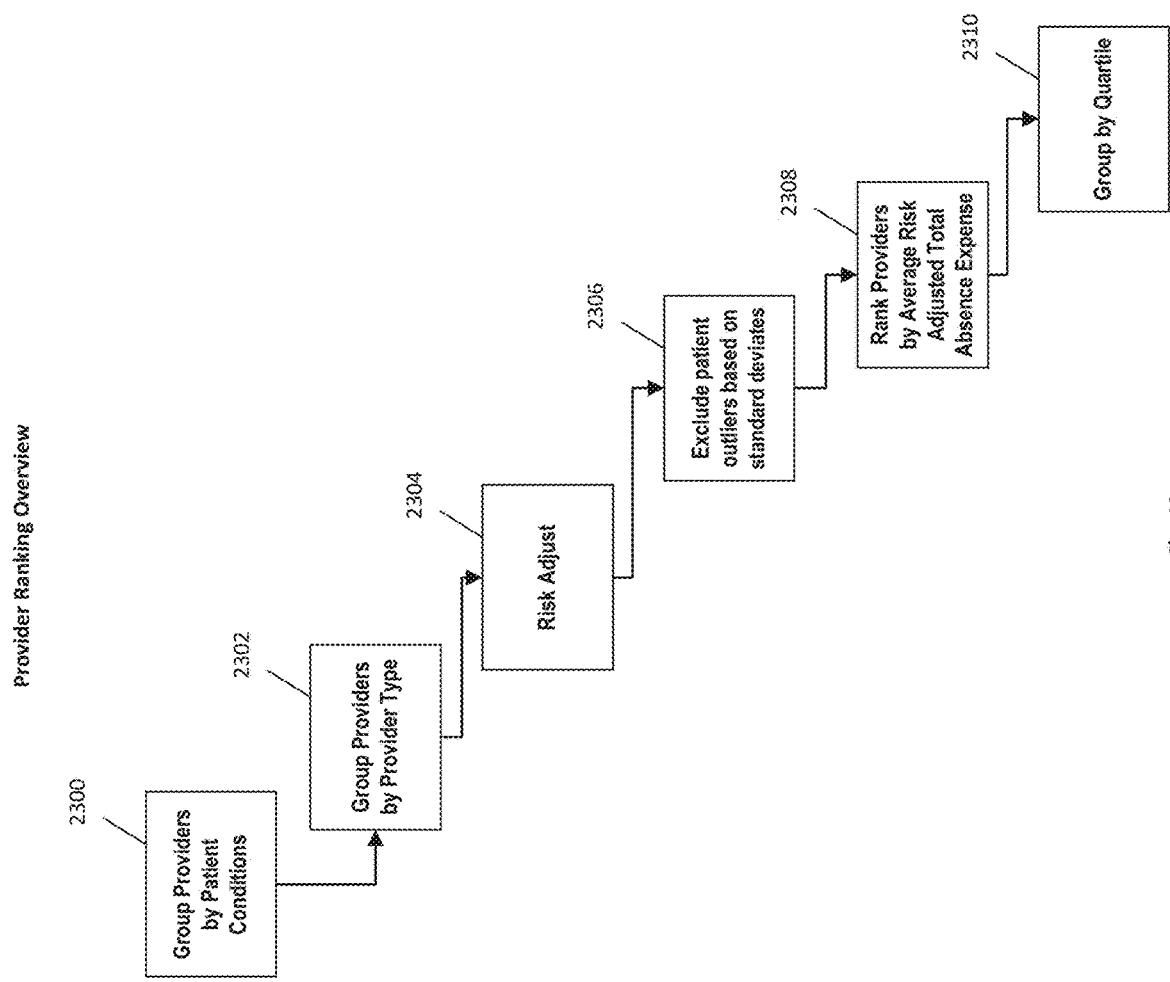
FIG. 13 depicts a provider ranking overview, which describes the grouping of providers by patient conditions (episodic, chronic, and worker's compensation), then by provider type (surgical, non-surgical, and others). The results go through a risk adjustment and exclusionary constraint based on outliers according to standard deviations. Average risk provides a basis for ranking providers through an analysis of adjusted total absence expense, and all providers are grouped by quartile.

FIG. 13 depicts a provider ranking overview in which providers are grouped by patient conditions (episodic, chronic, and workers' compensation) 2300, then as to provider type (surgical, non-surgical, and others) 2302. A risk adjustment 2304 is performed, and patient outliers are excluded based on standard deviations in 2306. In 2308, average risk provides a basis for ranking providers through an analysis of adjusted total absence expense, and in 2310, all providers are grouped by quartile.

Figure 14:
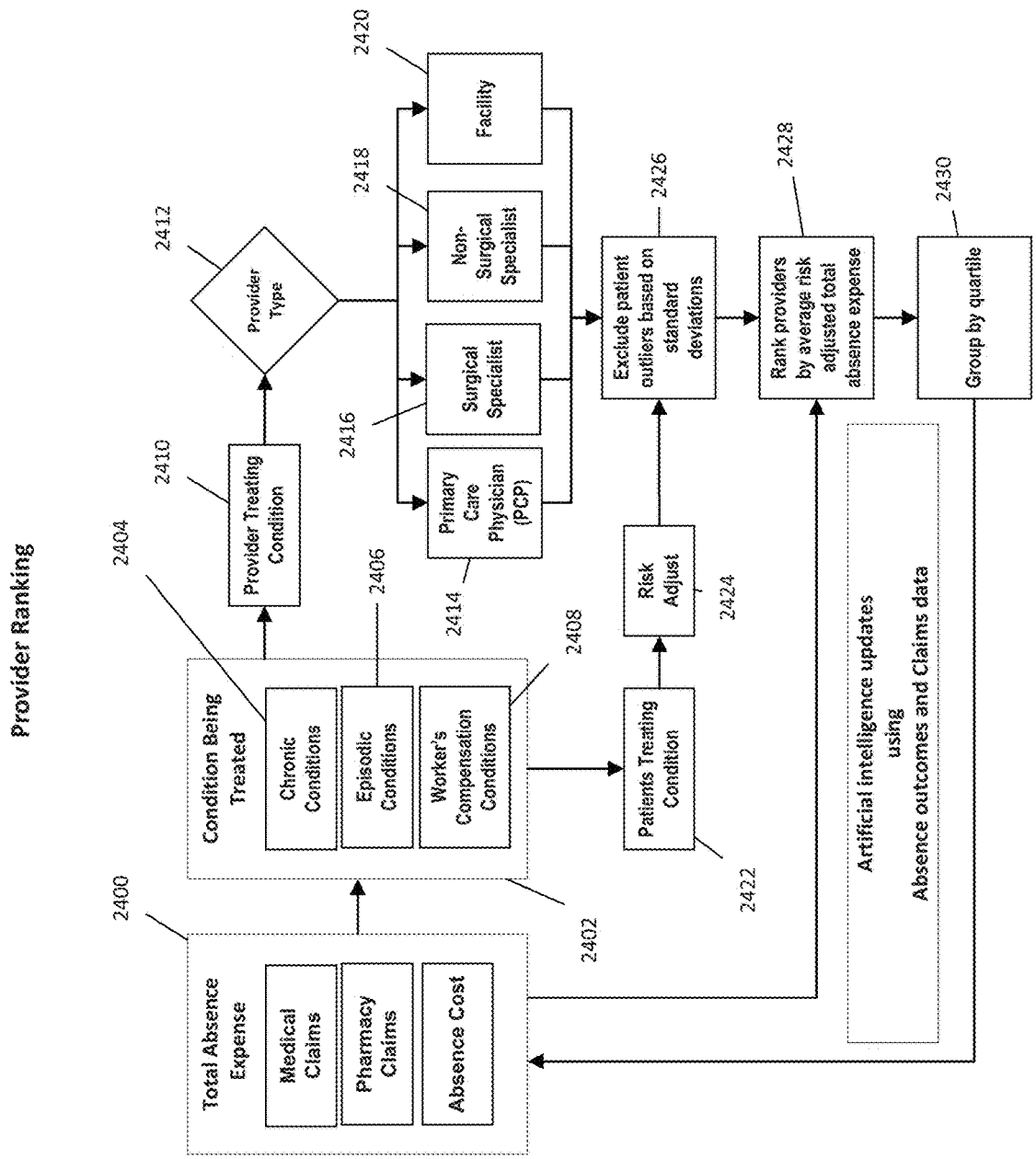
FIG. 14 depicts a ranking detail by claims, conditions, specialties and treating conditions risk adjusted utilizing artificial intelligence to provide updates using data outcomes and costing data for establishing a provider rank.

FIG. 14 depicts a provider ranking utilizing total absence expense 2400, which consists of medical claims from a third party administrator TPA, and pharmacy benefit manager claims, and absence cost. Data flows from total absence expense to conditions being treated 2402, which consists of episodic conditions (a first condition) 2404, chronic conditions (a second condition) 2406, and worker's compensation conditions (a third condition) 2408. From there, data proceeds to a provider treating a condition (a first treating condition) 2410, then to a provider type 2412. Additionally, provider type 2412 provides data to four specialties: a first specialty 2414, a second specialty 2416, a third specialty 2418, and a fourth specialty 2420, all of which transfer data into exclude patient outliers 2426. Referring back to condition being treated 2402, data then flows to patients treating condition (a second treating condition) 2422, which transfers data to a risk adjustment method 2424, and then to a system that reviews claims to exclude outliers based on standard deviations 2426. Data from total absence expense 2400 and block 2426 are provided to rank providers by average risk adjusted total absence expense 2428, which then provides that data to group by quartile 2430, which feeds data back to total absence expense 2400.

Figure 15:
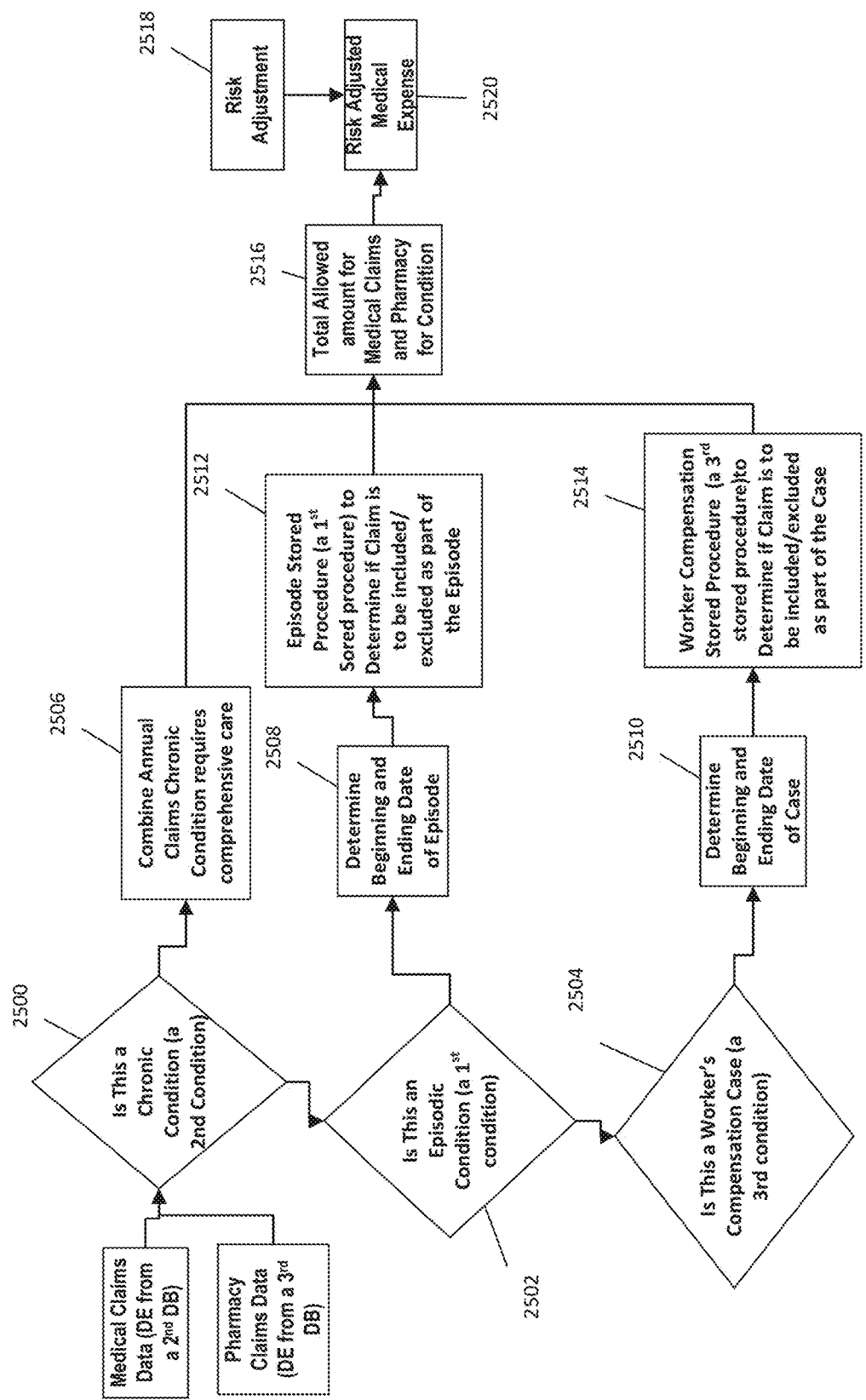
FIG. 15 depicts a decision flowchart describing a medical expense calculation pathway for healthcare medical claims data (i.e., a data extract from a second database of a third party administrator), which is inputted along with pharmacy claims data (a data extract from a third database of a pharmacy benefit manager and management system).

FIG. 15 shows a flow chart describing a medical expense calculation decision pathway for healthcare. The medical claims data (DE from a second DB) 102 and pharmacy claims data (DE from a third DB) 300 flow into a series of choices. Block 2500 asks if this is a chronic condition (a second condition), block 2502 asks if this is an episodic condition (a first condition), and block 2504 asks if is this worker's compensation case (a third condition). For a chronic condition, as determined in block 2500, annual claims are combined in block 2506, since a chronic condition requires comprehensive care which is a combination of care costs for a second condition. For an episodic condition, as determined in block 2502, commencement and ending dates of an episode are determined in block 2508, which feeds into an episode stored procedure 2512 (a first stored procedure which determines if a claim is included or excluded as part of an episode). For a worker's compensation case, as determined in block 2504, the commencement and ending dates are determined in block 2510, which feeds data into a worker's compensation stored procedure 2514. The output of blocks 2506, 2512, and 2514 are combined for a total allowed amount for medical claims and pharmacy for condition 2516, which provides the basis for a risk adjusted 2518, medical expense 2520.

Figure 16:
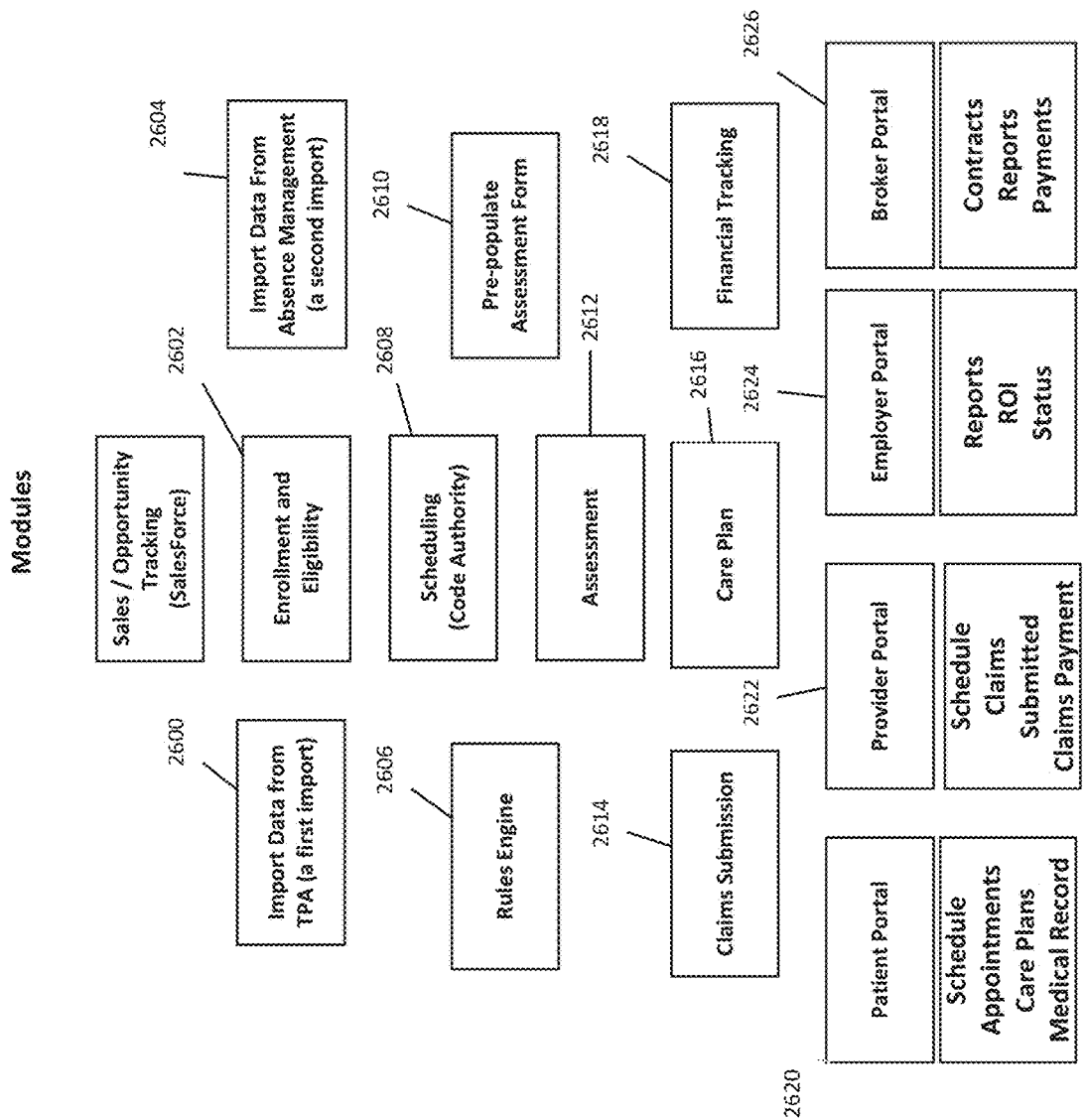
FIG. 16 depicts a broad description of major modules as containers for major code parts utilizing an outside provided system for tracking (e.g. Salesforce), import of data from a third party administrator and from an absence management system as part of the data extract from a first database, application of a scheduling system which acts as the coding authority for activation of any of a number of stored procedures, and assessment from claims submission (from medical claims of the third party administrator data extract of a second database).

FIG. 16 depicts modules as containers for code parts utilizing an outside provided system for tracking (e.g., Salesforce), import of data from a third party administrator (a first data import) 2600, an enrollment and eligibility module 2602, an import of data from absence management (a second import) 2604, a module for Rules Engines 2606, scheduling the code authority for the system 2608, including a pre-populate assessment form 2610, modules for assessment 2612, claims submission 2614, a customized care plan 2616, and financial tracking 2618. Also shown are modules for importing and exporting data through a series of portals, including a patient portal 2620, a provider portal 2622, an employer portal 2624, and a broker portal 2626.

FIG. 17 depicts a table of type of databases utilized, including industry reference databases 2700, logic rules database 2702, stage database 2704, production database 2706, and combined data 2708, all describing the database name in the system and a description of functionality. Industry reference databases 2700 provide a referential basis for risk scores as an industry standard and government standard which provides a knowledge base for the other databases for comparative purposes and as rules generator. The industry reference databases are operationally coupled and logically coupled to logic rules 2702. The logic rules 2702 provide priority information based on parameters passed to the comparators such as step 07, one of the stored procedures 740 (described with reference to FIG. 4B), which can either determine chronic conditions or episodic conditions or worker's compensation conditions depending on the parameters passed in the method. This stored procedure 740 (described with reference to FIG. 4B), acts to operationally group patients by condition and total medical expense. It is the logic rules 2702 that draw on data stored in industry reference databases 2700. Stage database 2704 is a type of database that exists in the form Stage_Client_XXX. It contains raw data or data extracted to specifications of industry reference databases 2700 and logic rules 2702. This data mirrors an employer's and a provider's and a TPA's data except for the addition of logic rules 2702 to the raw source data. Further, the production database 2706 is referenced in the format PTO_Saver_XXX and processed into a specialized format for use in specific schemas (i.e., groups of tables and other database structures organized in logical groups) within the database. The combined data 2708 is formatted in accordance with the style Master_Saver. This Master_Saver combined database 2708 is used to combine multiple sources of data for analysis under the logic rules 2702 or the industry reference database 2700. All of the databases are connected operationally through both comparator processes listed and utilization of logic rules 2702.

FIG. 18 depicts a table 2800 of databases utilized by the system, arranged by database name and schema for the various databases of risk adjustments, assessments, and standards. Shown are database objects and defaults 2802 and Miscellaneous schema 2804 (e.g., NEPPES, CMS HCC, USC-CDPS, CDC, CMS). Additionally, some of these references provide databases utilized by the logic rules 2702 (shown in FIG. 17) and also by the industry reference database 2700 with the naming schema for the first 8 databases shown as Alchemy.

Figure 19:
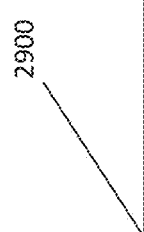
FIG. 19 is a table showing the naming of the master database in the system, schema (which are groupings of tables in logical groups), and a description of the schema. In this table, the schemas are Absence, Claims, Credentials, Database Object (default), Dictionary, Evaluation, foundation, Option List, Person, Schedule, and Workers Compensation.

FIG. 19 delineates the naming of the Master_Saver database (DB) 2900 in the system and its form as well as all other main non-transitory databases (DB) that draw their information and parameters from Master_Saver 2900. The schema (i.e., grouping of tables and other database structures in logical groups) in Master_Saver databases are at least Absence, Claims, Credentials, Database Object (default), Dictionary, Evaluation, Foundation, Option List, Person, Schedule, and Workers Compensation.

FIG. 20 depicts a table with a description of the PTO_Saver_XXX (DB) 3000. The PTO-Saver XXX database is the standard form from the Master_Saver database 2900, containing the same schema as described in FIG. 19, except that this PTO database also allows for the use of particularized data of employers and providers, including employee data.

FIG. 21 is a table identifying the list of stored procedures 3100, with stored procedures for the healthcare scenario as being Step 00 through Step 08 (steps 736, described with reference to FIG. 4B). Stored procedures 634 are more generally identified with reference to FIG. 4A. The stored procedures table 3100 is for stored procedures of any nature used in the system, including those not numbered by steps. Stored procedures are used to identify and perform a series of automatic tasks that the system can perform upon data input, identification, analysis, creation of transitory and non-transitory algorithms, and input and output of data over secured pathways over the cloud or a network. Stored procedures make calls on the database from code describing the nature of the report or analysis needed by a system participant. Stored procedures may change in real time based on conditional formatting within the code determined by pre-determined ranges and in some case based on transitory ranges that change based on changing input. Not all objects in a table are needed for each stored procedure call on the tables of the database, meaning that some objects may not be used in each stored procedure call (e.g., a pull or push to the database) based on rules and rules conditions of non-transitory stored procedures. The same rule and rules conditions apply to transitory stored procedures and stored procedure calls, however, those rules and rules conditions are generated in real time as conditions change. The stored procedures are identified in the following manner: Step 00—Run Process 3102, Step 01—CreateTables 3104, Step 02—PopulateData 3106, Step 03—CreateDictionaries 3108, Step 04—CreateFact 3110, Step 05—HCC Score 3112, Step 06—CDPS Score 3114, Step 07—LogicRules (e.g., LogicRules_EpisodicConditions 3118, LogicRules_ChronicConditions 3116, and LogicRules_WorkersCompensation 3120), and Step 08—Qscore 3122.

FIG. 22A provides functional descriptions for steps 00 to 03 of Stored Procedure. Step 00 Run Process is used to automate other steps; Step 01 Create Tables creates all the tables needed in the PTO_Saver Database; Step 02 Populate Data populates production tables from other raw data tables. This step is specific to the company supplying the data, and there are separate sections of code for each table being populated. This step populates tables with a schema type of "Foundation," "Absence," "Person," and "Claims." Step 03 CreateDictionaries populates production tables with data from "Populate Data" and "Alchemy" to create lookup tables with standardized definitions. The tables populated in this step have schema types of "OptionList" and "Dictionary." The first record of these tables should contain a generic record that can be used to indicate what information from the source database was not available. Although all objects are usable in a table of the PTO_Saver database, not all objects are used for each Stored Procedure call. Each call may be unique.

FIG. 23A depicts code demonstrating logical and operational function of condition and duration constraint. Episodic patients are analyzed based on procedures tied to the specific condition and duration, where conditions that cannot be impacted are excluded. The code describes an episodic employee (patient) and data analysis tied to specific conditions and duration, with conditions that cannot be impacted being excluded. Included in FIG. 23A is exemplary application code that allows for that process to occur.

FIG. 23B depicts code logic demonstrating rule functioning where a condition and duration rule is not satisfied. Episodic patients are analyzed based on procedures tied to the specific condition and duration. Claims where a rule was not satisfied are analyzed in context with other claims to determine if they contributed to the overall cost of the episode. This figure includes exemplary code for an episodic patient (employee) tied to a specific condition and duration. This figure represents the code that analyzes rules contextually with other claims to determine if a particular claim contributed to the overall cost of the episode.

```
update Claims.Charges [updating claims charges]
set LogicGroup = dbo.temp_LogicGroup_Diag_classified.LogicGroup, [logic group set and
classified] LogicRule='Same Date'
From Claims.Charges INNER JOIN
Dbo.temp_logicGroup_Diag_classified
ON Claims,Charges.Person_Id=dbo.temp_logicGroup_Diag_classified.Person_Id
AND Claim-Charges.DateofService =
dbo.temp_LogicGroup_Diag_classified.DateofService
Where Claims.Charges.logicGroup = 'No Rule Triggered'
Update Claims.Charges
set logicGroup = dbo.temp_logicGroup_Diag_classified.logicGroup, LogicRule = '-30 to -1
Days'[logic rule changed from Fig. 23A as this seeks outlier claims in the 1-30 day time frame]
FROM Claims.Charges INNER JOIN [an inner join as between two tables in databases, charged
against the person Identified]
dbo.temp_LogicGroup_Diag_classified
ON Claims.Charges.Person_Id = dbo.temp_LogicGroup_Diag_classified.Person_Id
AND Claims.Charges.DateofService between
dateadd(d,-30,dbo.temp_LogicGroup_Diag_classified.DateofService) [against the date of service
and the person Id claim charges may be made]
and dbo.temp_LogicGroup_Diag_classified.DateofService
where (Claims.Charges.LogicGroup ='No Rule Triggered') [when not within the 1-30 days cycle
then no charges are made]
```

FIG. 22B highlights aspects of Functional Descriptions of Stored Procedures for Step 04-06: Step 04 CreateFact; Step 05 HCC score, which is the Medicare risk score for comparative purposes; and Step 06 CDPS Score, which represents the University of Southern California at San Diego Chronic Illness and Disability Payment System (CDPS).

FIG. 22C depicts the general rules that apply to presentation of data to the system prior to structuring in a DB or through schema in a database (DB). In accordance with diagnosis, procedure, ICD/ICD9/ICD10 (International Classification of Diseases, 9.sup.th Revision and 10.sup.th Revision, respectively), and ICD-CM (International Classification of Diseases-Clinical Modifications), DRG (Diagnosis Related Group), Revenue Code, or prescription rules, as appropriate, patients are classed as episodic, chronic and worker's compensation. These are functional descriptions for patient (employee) classifications episodic, chronic and worker's compensation, that demonstrate the logical relationship. The ICDs are a standardized classification of disease, injuries, and causes of death, organized by etiology and anatomic localization and codified into a 6-digit number. They allow clinicians, statisticians, politicians, health planners and others to speak a common language, both within the United States and internationally.

FIG. 23C depicts code logic for when LogicRules Workers Compensation rules are not satisfied. Step 07 LogicRules Workers' Compensation Rules Not Satisfied represents the system functioning with additional conditions not found in an episodic patient (employee). Workers Compensation rules are defined by a triggering event, which occurs when a medical practitioner suggests that an absence is a Workers' Compensation absence. Another triggering event occurs when the employee returns to work. The employee's absence is measured by the time duration between the two triggering events. In an Episodic or Chronic condition there may be more than the two triggering events (i.e., repeating encounters) as well as the patient's release to return to work at full duty. Many conditions omitted from Episodic condition will be included in Workers' Compensation. The analysis is based on the type of provider seeing the patient. Exemplary code is depicted in the figure.

Select top 100 percent claims [identifies all the claims] Claims.Charges.Person_Id, Claims.Charges.DateofService, [correspondingly identifies a patient (person/employee) by medical claims a data extract of a TPA medical claims second database], Charges [costing of the medical claims], and
DateofService [correspondingly, an employer's human resources first database].

Claims where a rule was not satisfied are analyzed in context with other claims, including outlier claims to determine if they contributed to the overall cost of the episode.

FIG. 23D depicts Step 08—QScore. For each condition type (Chronic, Episodic, Workers Compensation) and provider type (primary care physician, non-surgical specialist, surgical specialist, institution, and demand services), and the corresponding patient population is identified. Each patient has an individual calculation for their risk score based on a number of parameters such as total medical expense and absence expense. The Provider is then ranked based on total risk adjusted absence expense. Providers outside two standard deviations are individually reviewed for possible extenuating circumstances (i.e., a patient is obese, has a chronic condition, high blood pressure, etc.). Providers are then assigned a quality score (QScore) based on their ranking. In addition to identifying the best doctors and other providers, the QScore reflects the employer's opportunities for savings by moving employees away from the low value providers. The QScore is the product of a contextualization engine. It analyzes and compares time and attendance with positive outcome for the lowest costs, and also determines whether other conditions must be observed to provide the best care. Even with a HVP and an employee with a positive outcome, an employee's risk factor could be rising perhaps due to other factors. The system learns contextually to look for other factors that may present as latent longer term effects, and the system makes that information available.

Shown below is a simplified overview of the logic behind the QScore (e.g., QScore Card or Doctor's QScore) use of algorithms as part of the artificial intelligence of the learning system.

1. Group each employee's medical claims by diagnosis:
   a. Chronic conditions (e.g. cardiac, diabetes, etc.)
   b. Episodic conditions (e.g. back, neck, etc.)
2. Sort by provider:
   a. Primary care physician ("PCP")
   b. Non-surgeon specialist
   c. Surgeon
   d. Institution (e.g., hospital)
3. Claims—Accumulate all related medical and pharmacy claims for the employee
   a. Productivity Costs
4. Juxtapose the claim dates against the HR attendance records
5. Accumulate and value all time off work related to the claims
   a. Add claims and productivity costs
6. Risk adjust the total costs by the employee's CDPS risk adjustment score (Chronic Illness and Disability Payment System)
   a. Score<1.00—No adjustment
   b. Score>1.00—Divide total costs by the risk adjustment score to decrease the cost to account for a sicker patient
7. Calculate the provider's average cost per employee for the diagnosis category (total risk adjusted costs divided by the number of employees)
8. Compare each provider's average cost per employee for that diagnosis to the group average (e.g., all PCPs, etc.)
   a. If a provider's average cost is less than the group average, there is no opportunity for savings
   b. If the provider's average cost is above the group average, then an opportunity for savings exists by moving employees from this high cost provider to a lower cost provider.

The QScore (e.g., a ranking number as between providers) encapsulates the above algorithms for each provider on each diagnostic category in a number ranging from 0 to 100. The higher the QScore, the higher the value of that provider when treating that diagnosis and a diagnosis of that condition.

Figure 24:
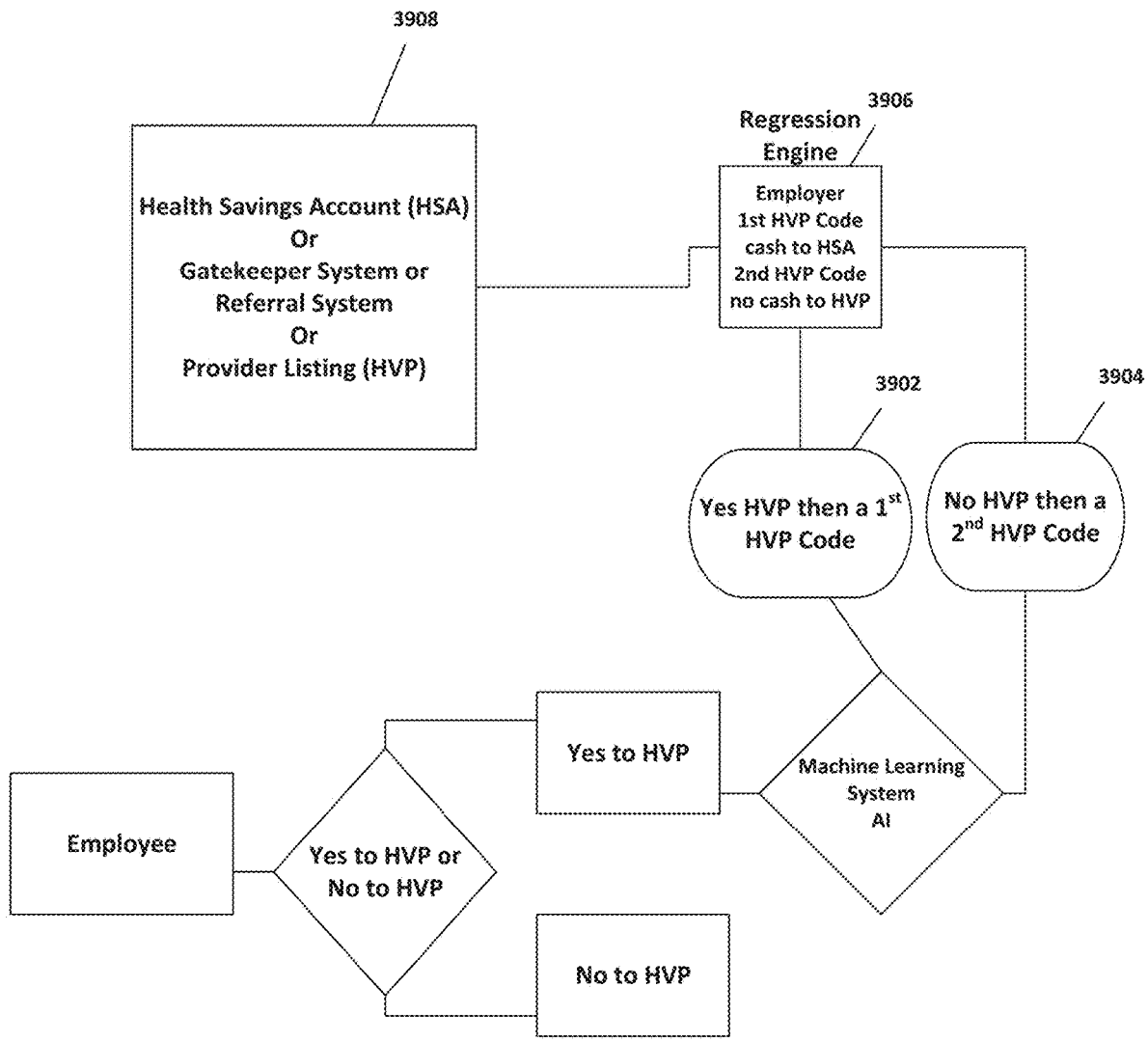
FIG. 24 depicts a system of incentivizing employees to select High Value Providers (HVP) and further depicts a regression analysis engine.

FIG. 24 depicts a flowchart of an incentive plan which incentivizes the employee to achieve quality healthcare by selecting a high value provider (HVP) through an additional deposit of money in an employee's Health Savings Account (HSA) upon selecting the High Value Provider 3908. Also shown is a regression analysis engine 3906, which analyzes the collected data and prepares best practices for conditions, specialties, geographic and demographic analysis. The engine's algorithm determines the reason for one provider performing better than another provider. The engine's algorithm also suggests that the best practices for one provider be utilized by another provider with the ultimate goal of improving the provisioning of healthcare. In the regression analysis engine, a first HVP code 3902 and a second HVP code 3904 are brought together to determine a cash or no cash situation.

The regression engine 3906 is used for further analysis of blinded or non-blinded data to determine best practices in a particular specialty, by provider, or geographically and in some cases demographically. This data provides sufficient information in a particular area (specialty, condition, geographically, or demographically) to provide a base of data not requiring individualized company-by-company analysis. This is because all providers in a given area would be included with standardized best practices established so that a company may only need to use a subscription based model to get appropriate information for its employees.

The regression engine 3906 further supports the filtering of data for later use in a subscription based model where other employers in a given area may not need the analysis conducted on their data. This is particularly applicable where all of an employer's providers have already been analyzed and QScores have already been assigned as a result of other employers in the area utilizing this machine learning system. Additionally, if other employers can utilize the data, then even non self-insured employers could utilize the data for their employees.

A self-insured employer that does not have a specific HSA program may instead use a gatekeeper program, in which an employer can require that its employees be referred to the HVP in all cases. The self-insured employer may also use a referral program. The system maintains a HVP database that an employer may use on a subscription basis with their employees.

FIG. 25A depicts the PTO_Saver Charges table 4000, describing the various objects under consideration for the system. The table is shown in three columns in the figure for compactness. Charges are identified by Charge_Id, Third-PartyAdministrator_Id, TPANativeKey, CompanyNativeKey, CompanyName, Company_Id, Company_Location, Corporation, WorkSite_Id, WorkSiteName, EmployeeNativeKey, RevCode, PersonNativeKey, Person_Id, ProviderNativeKey, Provider_Id, BillingProviderNativeKey, BillingProvider_Id, ReferringProviderNativeKey, ReferringProvider_Id, ServicingProviderNativeKey, ServicingProvider_Id, Ordering ProviderNativeKey, OrderingProvider_Id, Midlevel Provider_Id, SupervisingProviderNativeKey, SupervisingProvider_Id, ClaimNumber, EncounterNumber, which is a claim number parent name, DateofService, MonthofService, AdmitDate, DischargeDate, LengthofStay, TypeofService, TypeofService_Id, and BillType, which is a three-digit alphanumeric code that provides three specific pieces of information to a Charge. A first digit identifies the type of facility. A second digit classifies the type of care. A third digit indicates a sequence of this bill in this particular episode of care. It is referred to as a "frequency" code. Charges in the PTO Saver Charges table 4000 are further identified by CPT and Mod1, which is a service or procedure that can be further described by using 2-digit modifiers. The Modifier Reference Guide Lists Level I (CPT-4), Level II (non-CPT-4 alpha numeric), and Level III (local) modifiers. Level I and Level II modifier definitions are contained in the Healthcare Common Procedure Coding System (HCPCS). HCPCS is a set of health care procedure codes based on the American Medical Association's Current Procedural Terminology (CPT). Charges in the PTO_Saver Charges table 4000 are further identified by Mod2 (see the foregoing description of Mod1), ChargeAmount, DiagnosisType, Diagnosis 1, Diagnosis 2, Diagnosis 3, Diagnosis 4, Diagnosis 5, Diagnosis 6, Diagnosis 7, Diagnosis 8, Diagnosis 9, Diagnosis 10, Diagnosis 11, RevenueCode, which is a Uniform Billing (UB) revenue code on a claim, NDC, HCPCS, RVU, which is a related value unit, Specialty, Facility_Id, Location_Id, Location, LocationNativeKey, which is a natural key from the client, Department_Id, Department, PlaceofService, PlaceofService_Id, and Units. For HCPCSs and NDCs, units is an amount. When a HCPCS is required, units are entered in multiples of the units shown in the HCPCS narrative description. For example, if the description for the code is 50 mg, and 200 mg are provided, units are shown as 4. Charges in the PTO_Saver Charges table 4000 are further identified by ClaimEnteredBy, ClaimEnteredDate, AllowedAmount, InsurancePortion, PatientPortion, Fee, CoPayAmount, OtherinsurancePayment, and WorkRVU, which stands for work relative value units—a method for calculating the volume of work or effort expended by a physician. Charges in the PTO Saver Charges table 4000 are further identified by PatientNumber, AccountNumber, TotalPaid, TotalAdjustments, TotalBalance, and Betos_Id, which refers to Berenson-Eggers Type of Service (BETOS) codes, which are assigned for each Health Care Financing Administration Common Procedure Coding System (HCPCS) procedure code. The BETOS Coding system was developed primarily for analyzing the growth in Medicare expenditures. The coding system covers all HCPCS codes, assigns a HCPCS code to only one BETOS (Berenson-Eggers) type of service code, consists of readily understood clinical categories (as opposed to statistical or financial categories), consists of categories that permit objective assignment, is stable over time, and is relatively immune to minor changes in technology or practice patterns. Charges in the PTO Saver Charges table 4000 are further identified by PrimaryInsurance_Id, CurrentInsuranceNativekey, PrimaryInsurance, PrimaryInsuranceNativeKey, FinanceClass_Id, FinancialClass, ResponsibleProviderNativeKey, ProcedureCode_Id, DiagnosisGroup_Id, Diagnosis_Id, ProcedureType_Id, DiagnosisGroup, ProcedureGroup, DrugType_Id, and LogicRule, which is a rule for the claim line that was triggered, such as 1 to 30 days or Same Date. Charges in the PTO_Saver Charges table 4000 are further identified by LogicGroup_Id, LogicGroup, LogicGroup_iag, LogicGroup_CPT, LogicGroup_DRG, LogicGroup_RevCode, LogicGroup_NDC, Diagnosis_Group_WorkerComp, LogicGroup_ConditionType, Claim_Id, Injury_Id, which is a date of injury for a Workers Comp claim, LogicGroup_AssignedProvider_Id, Corvel doi, (e.g., VendorDateofInquiry) and ClaimType_Id.

Figure 25B:
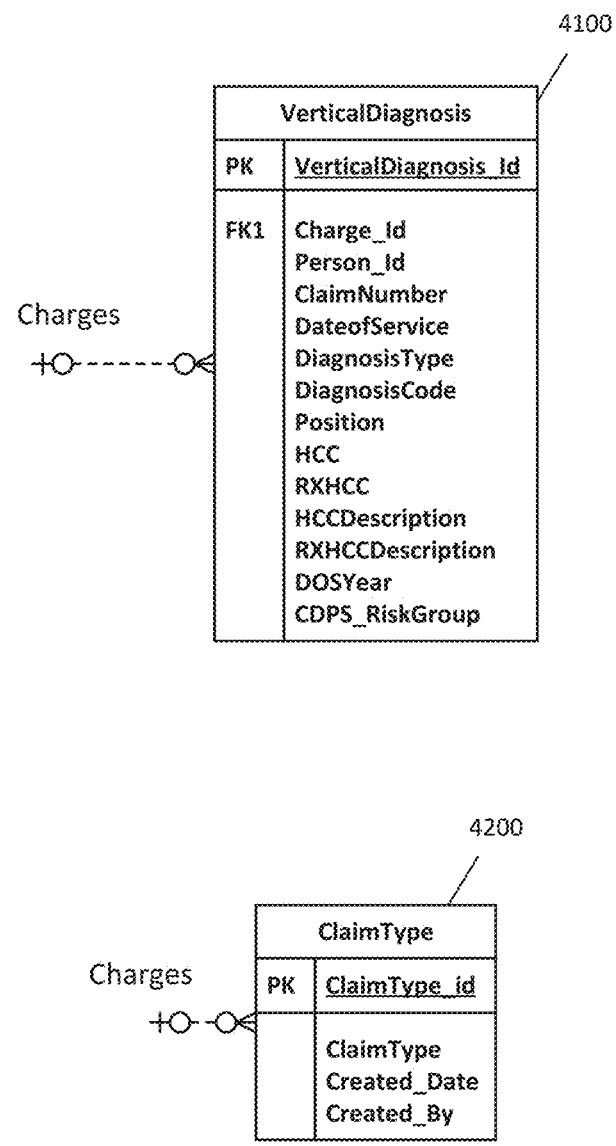
FIG. 25B depicts the PTO_Saver VerticalDiagnosis and ClaimType tables.

FIG. 25B depicts PTO_Saver VerticalDiagnosis table 4100 and ClaimType table 4200. PTO_Saver VerticalDiagnosis has Charge_Id, Person_Id, ClaimNumber, DateofService, DiagnosisType, DiagnosisCode, Position, HCC, RXHCC, HCCDescription, RXHCCDescription, DOSYear (i.e., Date of Service Year), and CDPS_RiskGroup. A single claim in the Charges table 4000 has many diagnoses, so for each claim the system creates a row per diagnosis code. VerticalDiagnosis table 4100 is connected with and communicates with the Charges table 4000, from which the Charge_Id is derived. ClaimType table 4200 also communicates with Charges table 4000 and has a primary key of ClaimType_Id with a ClaimType (e.g., object of a table), Created_Date, and Created_By.

Figure 25C:
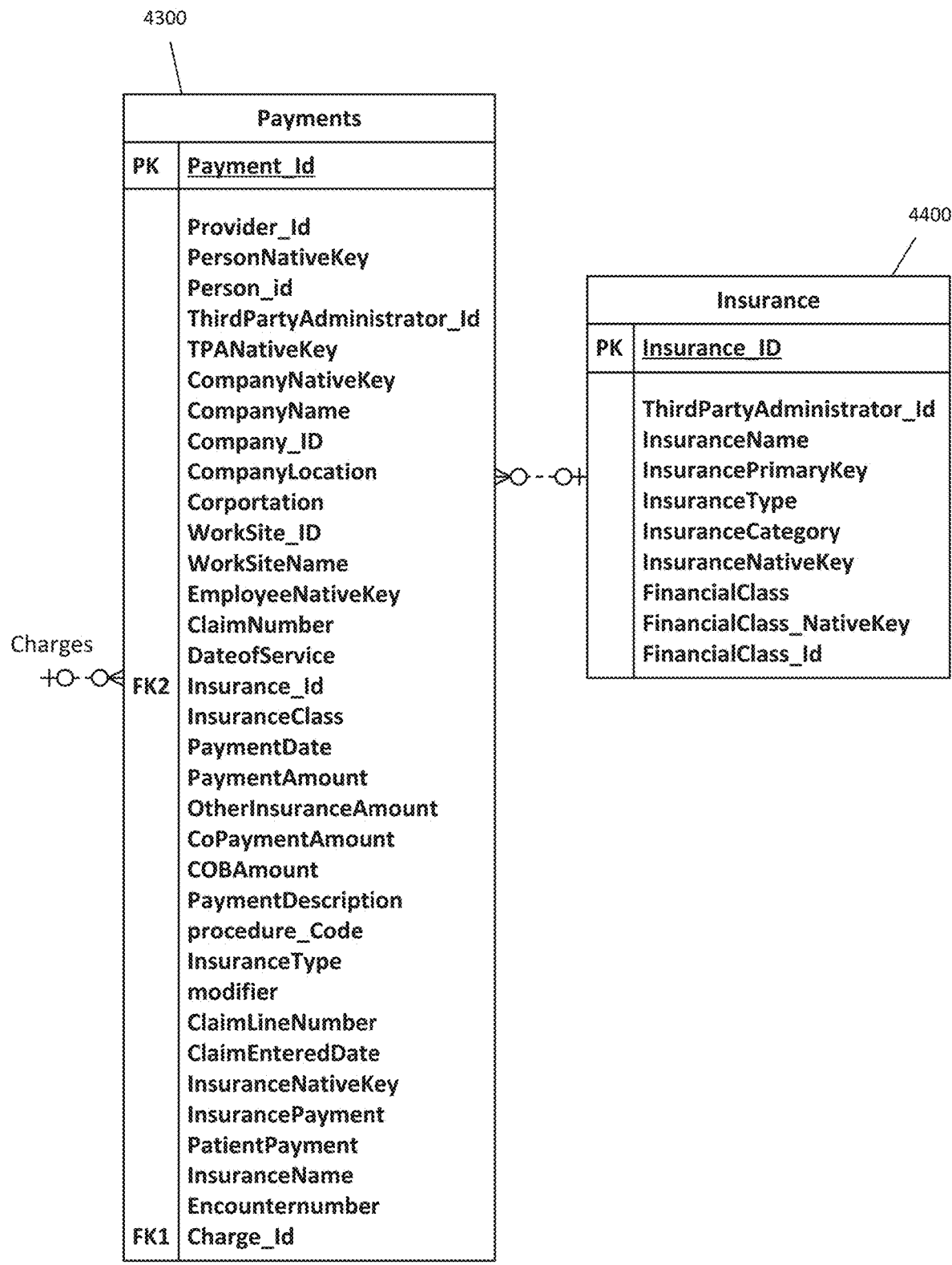
FIG. 25C depicts the PTO_Saver Payments and Insurance tables.

FIG. 25C depicts PTO_Saver Payments table 4300 and Insurance table 4400. The Payments table 4300 has a primary key Payment_Id and has Provider_Id, PersonNativeKey, Person_Id, ThirdpartyAdministrator_Id, TPANativeKey, CompanyNativeKey, CompanyName, Company_Id, CompanyLocation, Corporation, WorkSite_Id, WorkSiteName, EmployeeNativeKey, ClaimNumber, DateofService, Insurance_Id, InsuranceClass, PaymentDate, PaymentAmount, OtherInsuranceAmount, CoPaymentAmount, COBAmount, PaymentDescription, Procedure_Code, InsuranceType, and Modifier, in which a service or procedure can be further described by using a 2-digit modifier. The Modifier Reference Guide Lists Level I (CPT-4), Level II (non-CPT-4 alpha numeric), and Level III (local) modifiers. Level I and Level II modifier definitions are contained in the Healthcare Common Procedure Coding System (HCPCS). The Payments table 4300 also has ClaimLineNumber, ClaimEnteredDate, InsuranceNativeKey, InsurancePayment, PatientPayment, InsuranceName, EncounterNumber, and Charge_Id. Insurance table 4400 has Insurance_Id, ThirdPartyAdministrator_Id, InsuranceName, InsurancePrimaryKey, InsuranceType, InsuranceCategory, InsuranceNativeKey, FinancialClass FinancialClass_NativeKey, and FinancialClass_Id.

Figure 25D:
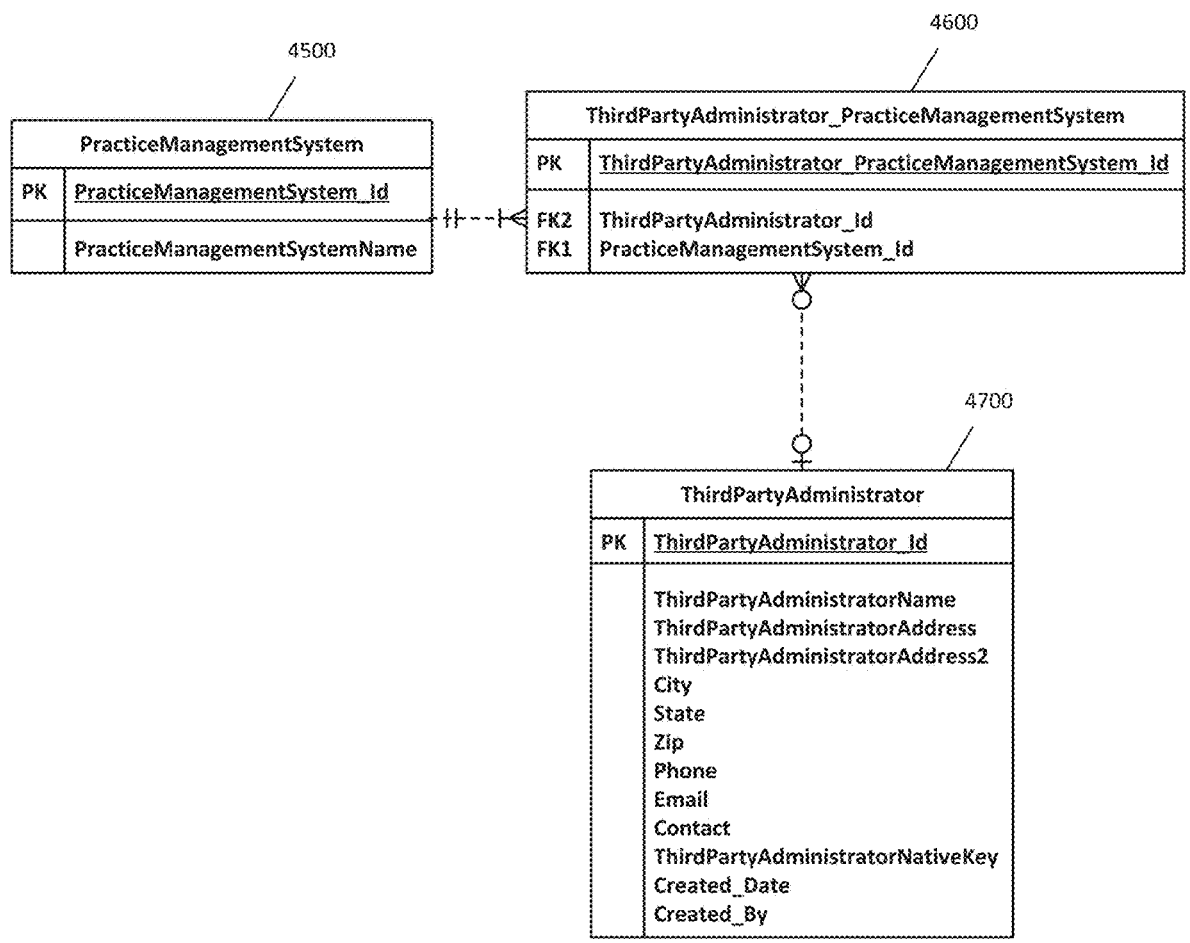
FIG. 25D depicts the PTO_Saver PracticeManagementSystem, ThirdPartyAdministrator PracticeManagementSystem, and ThirdPartyAdministrator tables.

FIG. 25D depicts PTO_Saver PracticeManagementSystem table 4500, which has PracticeManagementSystem_Id and a PracticeManagementSystemName. Also shown is PTO_Saver ThirdPartyAdministrator PracticeManagementSystem table 4600, with the primary key ThirdPartyAdministrator PracticeManagementSystem_Id and ThirdPartyAdministrator_Id, and PracticeManagementSystem_Id. Also shown is PTO_Saver ThirdPartyAdministrator table 4700. which has a primary key of ThirdPartyAdministrator_Id, and ThirdPartyAdministratorName, ThirdPartyAdministratorAddress, ThirdPartyAdministratorAddress2, City, State, Zip, Phone, Email, Contact, ThirdPartyAdministratorNativeKey, which is the natural key from the client used to identify files separate and distinct from other third parties, Created_Date, and Created_By.

Figure 25E:
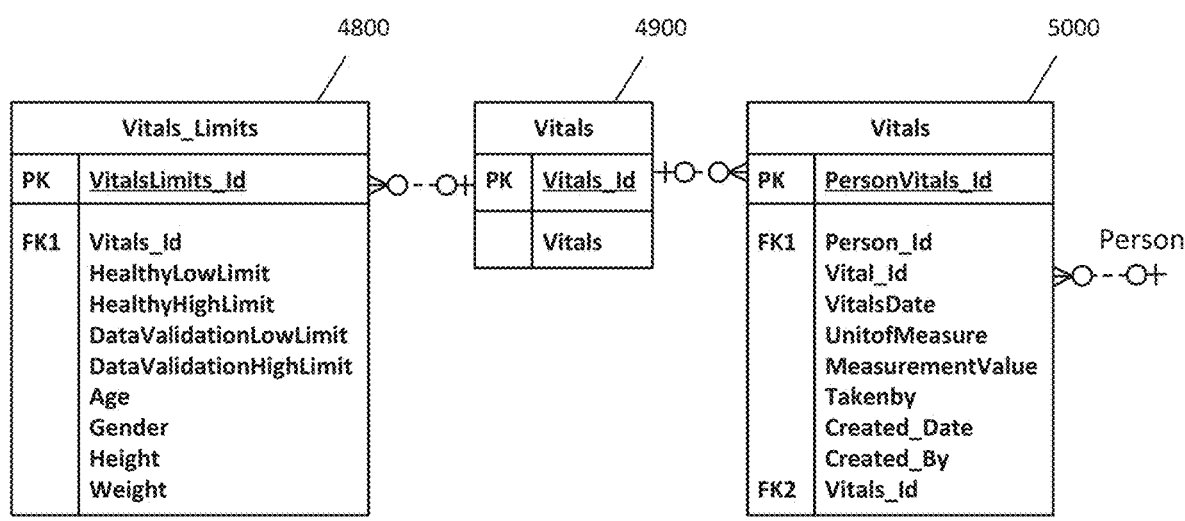
FIG. 25E depicts the PTO_Saver Vitals_Limits and Vitals tables.

FIG. 25E depicts PTO_Saver VitalsLimits table 4800, which has VitalsLimits_Id as a primary key and Vitals_Id, HealthyLowLimit, HealthyHighLimit, DataValidationLowLimit, DataValidationHighLimit, Age, Gender, Height, and Weight. Also shown is a first Vitals table 4900, which has Vitals_id as a primary key and Vitals as an object of the table. Also shown is a second Vitals table 5000, with PersonVitals_Id, a Foreign key of Person_Id, from another table, Vital_Id (from Vitals table), VitalsDate, UnitofMeasure, MeasurementValue, TakenBy, Created_Date, Created_By, and a Vitals_Id, a second foreign key in the second Vitals table 5000.

Figure 25F:
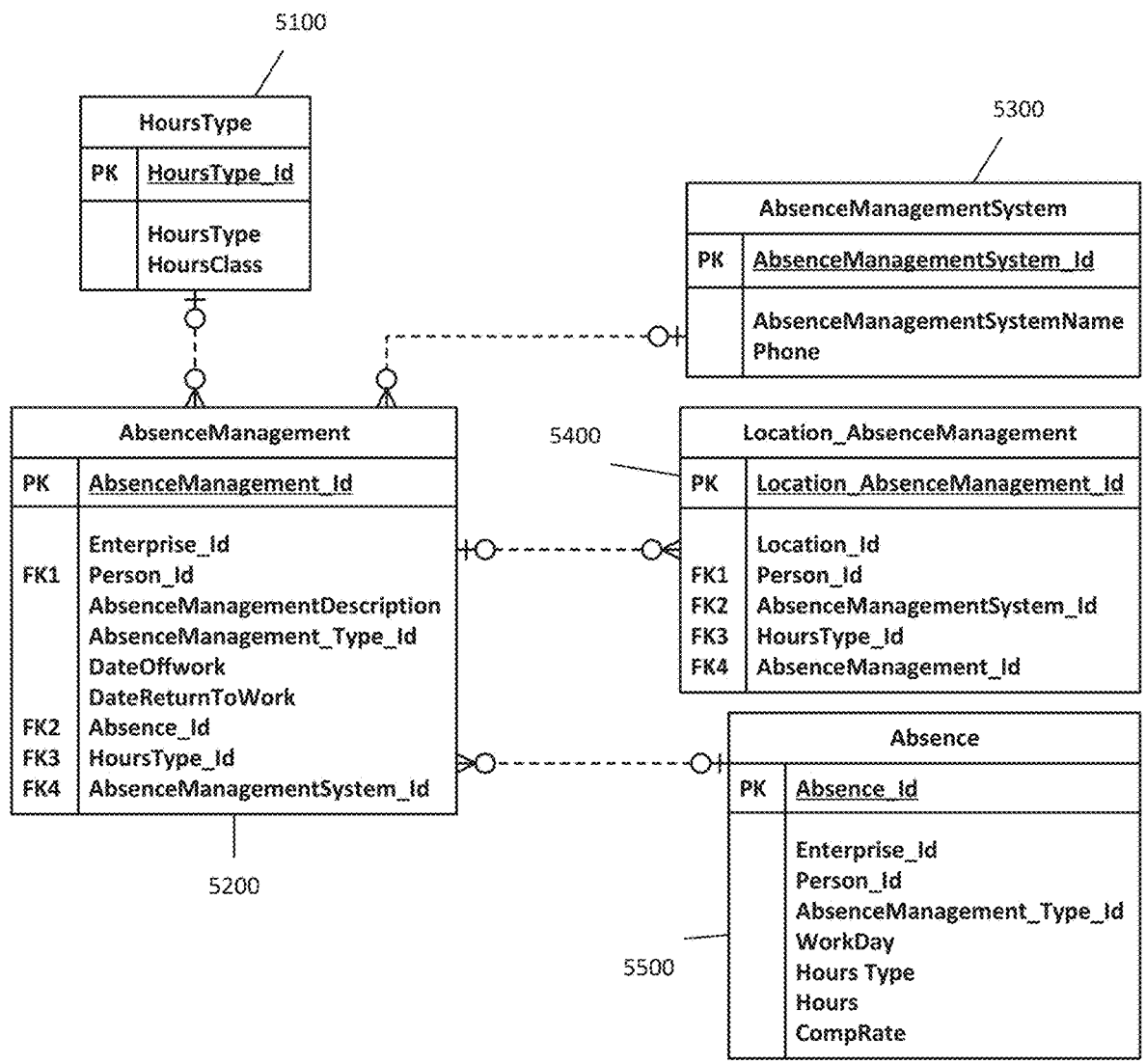
FIG. 25F depicts the PTO_Saver HoursType, AbsenceManagement, Location_AbsenceManagement, and Absence tables.

FIG. 25F depicts PTO_Saver AbsenceManagement table 5200, which references AbsenceManagement_Id as the primary key, and Enterprise_Id, Person_Id, which is a first foreign key, AbsenceManagementDescription, AbsenceManagement Type_Id, DateOffWork, DateReturnToWork, Absence_Id, which is a second foreign key, HoursType_Id, which is a third foreign key, and AbsenceManagementSystem_Id, which is a fourth foreign key. The AbsenceManagement table 5200 conveys data and communicates with the Person Table 10600. PTO_Saver HoursType table 5100 has a primary key of HoursType_Id, and includes HoursType, (an object of the table HoursType 5100) and HoursClass. Also shown is PTO Saver Location_AbsenceManagement table 5400, with a primary key of Location AbsenceManagement_Id, and the sub-objects of the object Location_Id, with Person_Id as a first foreign key, AbsenceManagementSystem_Id as a second foreign key, HoursType_Id as a third foreign key, and AbsenceManagement_Id as a fourth foreign key. Also shown is PTO_Saver Absence table 5500, which communicates with AbsenceManagement table 5200 and has a primary key of Absence_Id, Enterprise_Id, AbsenceManagement Person_Id, AbsenceManagement_Type_Id, WorkDay, HoursType, Hours, and CompRate. Also shown is AbsenceManagementSystem table 5300, which has AbsenceManagementSystem_Id as a primary key and further includes AbsenceManagementSystem-Name and Phone.

Figure 25G:
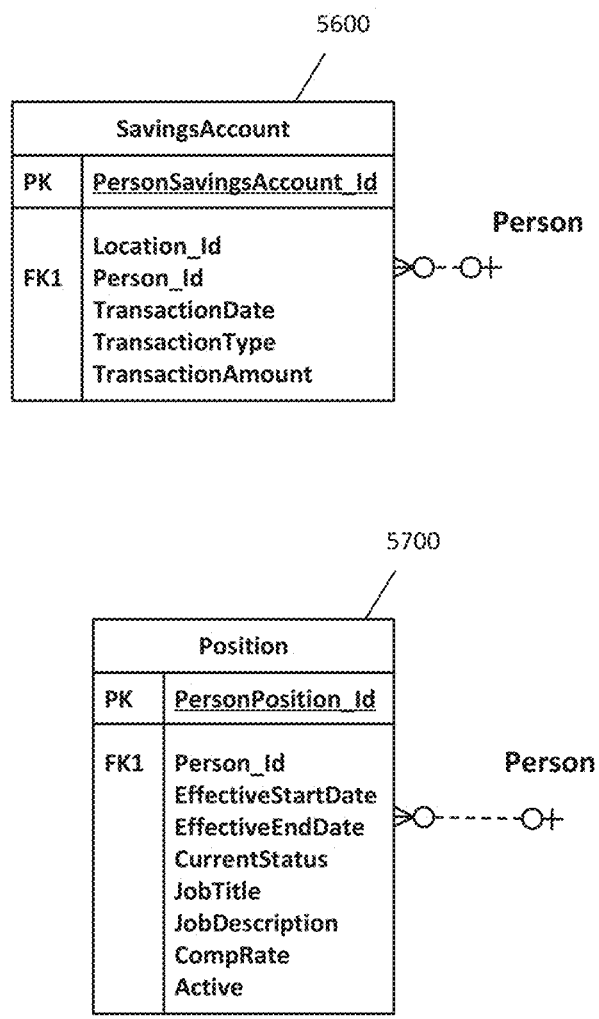
FIG. 25G depicts the PTO_Saver SavingsAccount and Position tables.

FIG. 25G depicts PTO_Saver SavingsAccount table 5600, with a primary key of PersonSavingsAccount_Id, a Location_Id, Person_Id, which is a first foreign key, TransactionDate, TransactionType, and Transaction Account. SavingsAccount table 5600 feeds many to one with the Person Table 10600. Also shown is PTO_Saver Position table 5700, which is a position of which diagnosis code field the code was in. The primary position (i.e., position 1) is the most important. Position table 5700 also feeds to Person table 10600 and has a primary key of PersonPosition_Id, a first foreign key of Person_Id, EffectiveStartDate, EffectiveEndDate, a CurrentStatus, a JobTitle, JobDescription, a CompRate, and Active.

Figure 25H:
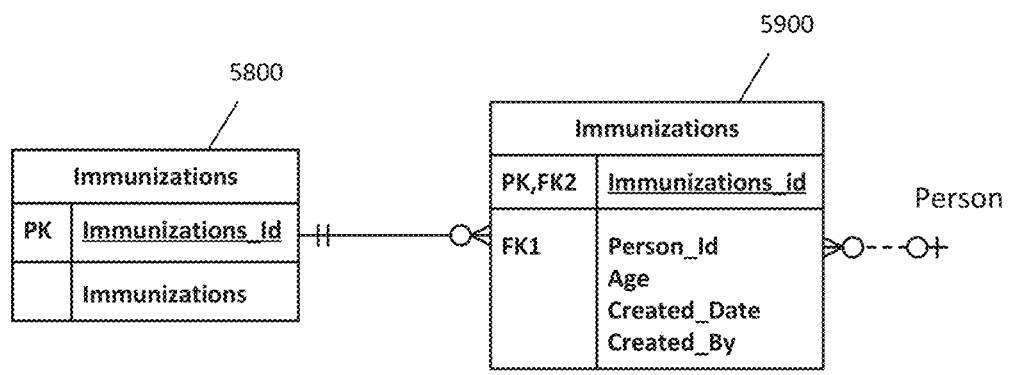
FIG. 25H depicts the PTO_Saver Immunizations tables.

FIG. 25H depicts PTO_Saver Immunizations table 5800, with Immunizations_Id as a primary key and Immunizations. In Immunizations table 5900, Immunizations_Id is both a primary key and a second foreign key, with Person_Id as a first foreign key, Age, Created_Date, and Created_By. Both tables are linked and are many to one related to the Person table 10600.

Figure 25I:
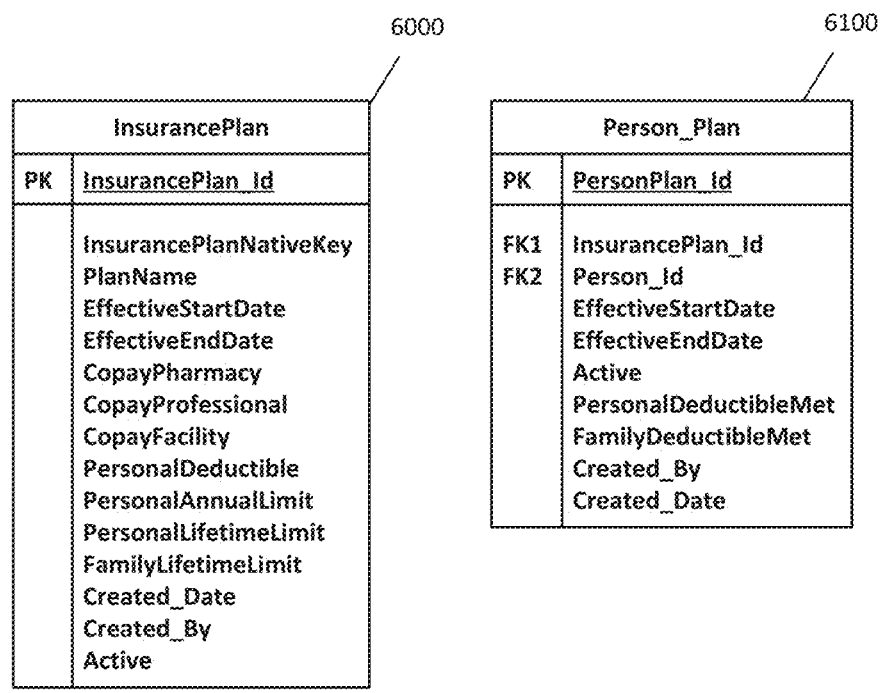
FIG. 25I depicts the PTO_Saver Person_Plan and InsurancePlan tables.

FIG. 25I depicts PTO_Save Person_Plan table 6100, with a primary key of PersonPlan_Id, a first foreign key InsurancePlan_Id, a second foreign key of Person_Id, Effective StartDate, EffectiveEndDate, Active, PersonalDeductibleMet, FamilyDeductibleMet, Created_By, and Created_Date, which relates to the Person Table 10600. PTO_Saver InsurancePlan table 6000 has a primary key of InsurancePlan_Id, InsurancePlanNativeKey, PlanName, EffectiveStartDate, EffectiveEndDate, CoPayPharmacy, CoPayProfessional, CoPayFacility, PersonalDeductible, PersonalAnnualLimit, PersonalLifetimeLimit, FamilyLifeTimeLimit, Created_Date, Created_By, and Active.

Figure 25J:
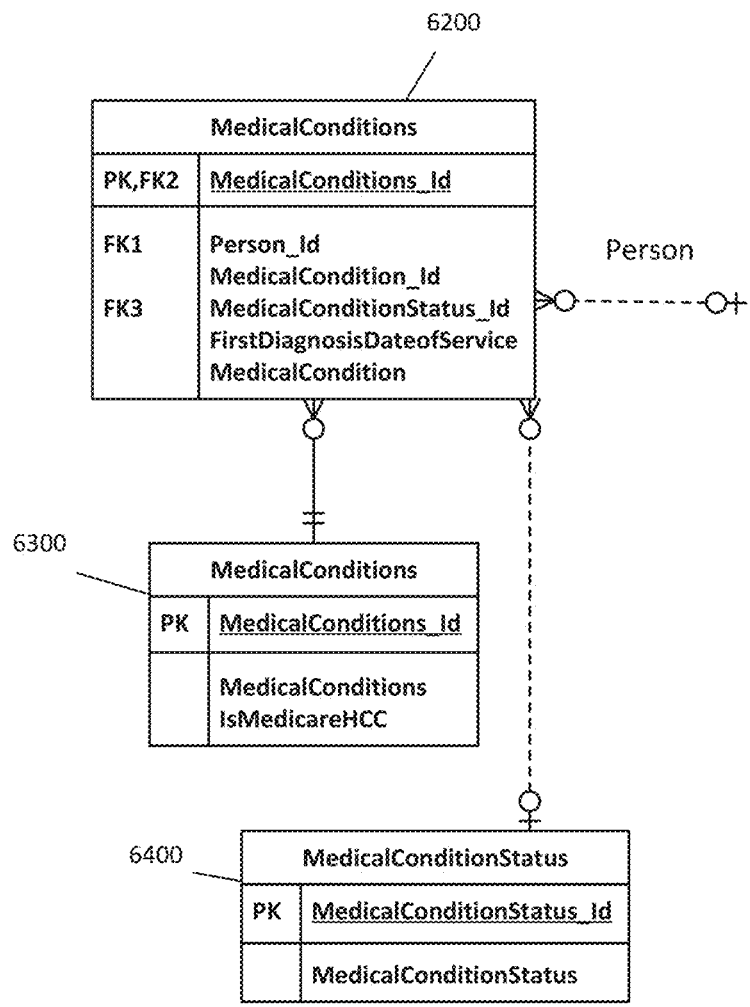
FIG. 25J depicts the PTO_Saver MedicalConditions and MedicalConditionStatus tables.

FIG. 25J depicts PTO_Saver MedicalConditions table 6200, which communicates with Person table 10600. MedicalConditions table 6200 has a primary key and second foreign key of MedicalConditions_Id, a first foreign key of Person_Id, MedicalCondition_Id, MedicalConditionStatus_Id, FirstDiagnosisDateofService, and MedicalConditions. Medical Conditions table 6300 has a Primary Key of MedicalConditions_Id, MedicalConditions, and IsMedicareHCC. Also shown is MedicalConditionStatus table 6400, with a MedicalConditionStatus_Id as a primary key and MedicalConditionStatus as an object.

Figure 25K:
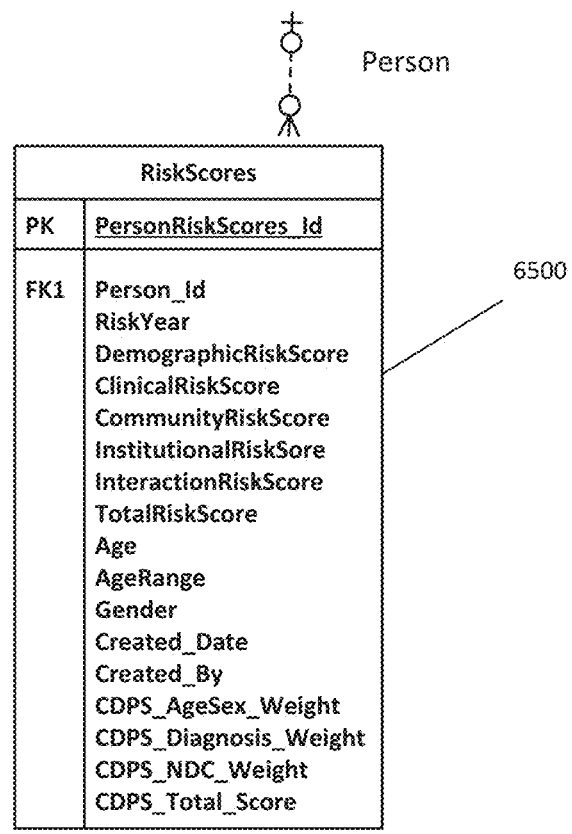
FIG. 25K depicts the PTO_Saver PersonRiskScores table.

FIG. 25K depicts PTO_Saver RiskScores table 6500, which communicates with the Person table 10600. RiskScores table 6500 has a primary key of PersonRiskScores_Id, a first foreign key of Person_Id, RiskYear, DemographicRiskScore, ClinicalRiskScore, CommunityRiskScore, InstitutionalRiskScore, InteractionRiskScore, TotalRiskScore, Age 8012, AgeRange, Gender, Created_By, Created_Date, a CDPS_AgeSex_Weight, CDPS_Diagnosis_Weight, CDPS_NDC_Weight, and CDPS_Total_Score.

FIG. 25L depicts PTO_Saver PossibleInteractions table 6600, which communicates with Person table 10600. PossibleInteractions table 6600 has a primary key of PossibleInteractions_Id, first foreign key of Person_Id, Sepsis, Opportunistic Infections, Cancer, Diabetes, Bone/Joint/Muscle Infections/Necrosis, Immune Disorders, Schizophrenia, Multiple Sclerosis, Seizure Disorders and Convulsions, Cardiorespiratory Failure, Congestive Heart Failure, Chronic Obstructive Pulmonary Disease (COPD), Aspiration and/or Specified Bacterial Pneumonias, Renal Disease, Pressure Ulcer, Chronic Ulcers of Skin, except Pressure, Artificial Openings for Feeding or Elimination, int1, int2, int3, int4, int5, int6, and InteractionRiskScore.

Figure 25M:
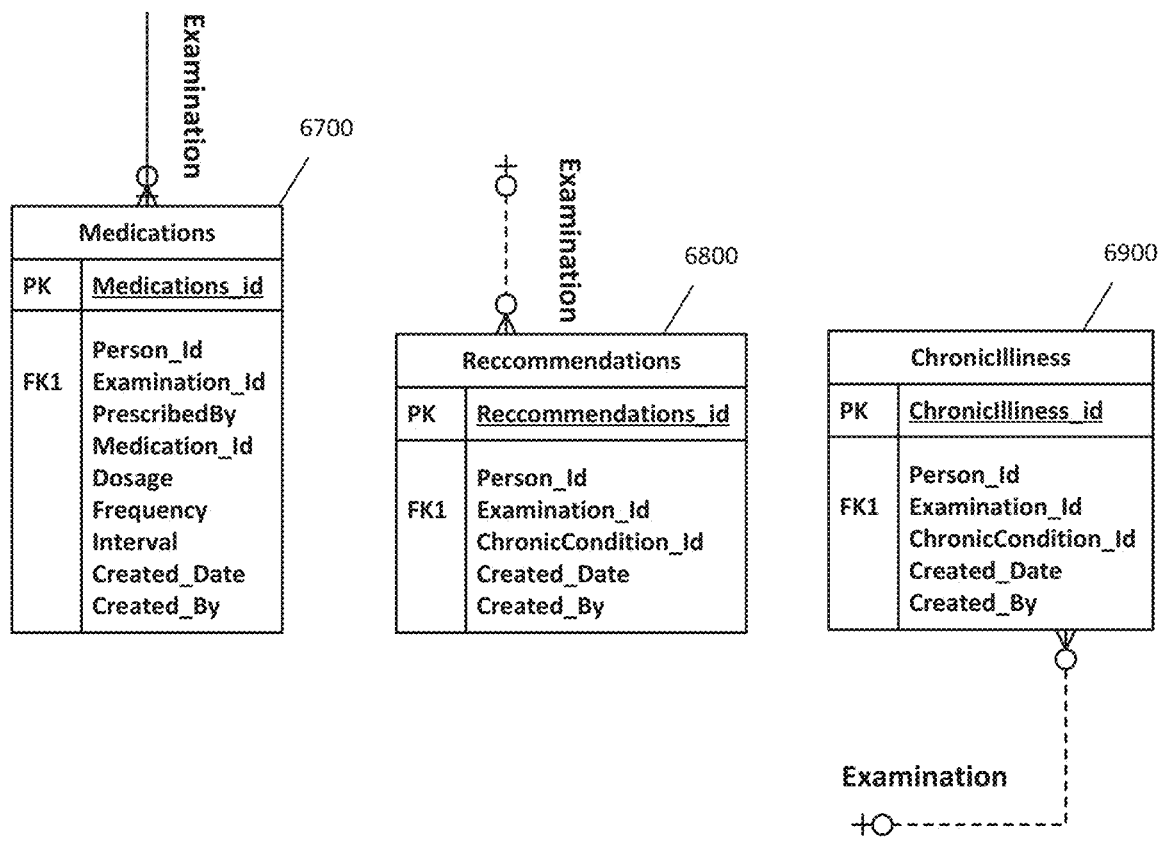
FIG. 25M depicts the PTO_Saver Medications, Recommendations, and ChronicIllness tables.

FIG. 25M depicts PTO Saver Medications table 6700, which has Medications_Id as primary key, Person_Id, Examination_Id as foreign key, Prescribed_By, Medication_Id, Dosage, Frequency, Interval, Created_Date, and Created_By. Medications table 6700 communicates in a many to one fashion with Examination table 7700. Recommendations table 6800 has primary key of Recommendations_Id, Person_Id, a first foreign key of Examination_Id, ChronicCondition_Id, Created_By, and Created_Date. ChronicIllness table 6900 has a primary key of ChronicIllness_Id, Person_Id, a first foreign key of Examination_Id, ChronicCondition_Id, Created_Date, and Created_By.

Figure 25N:
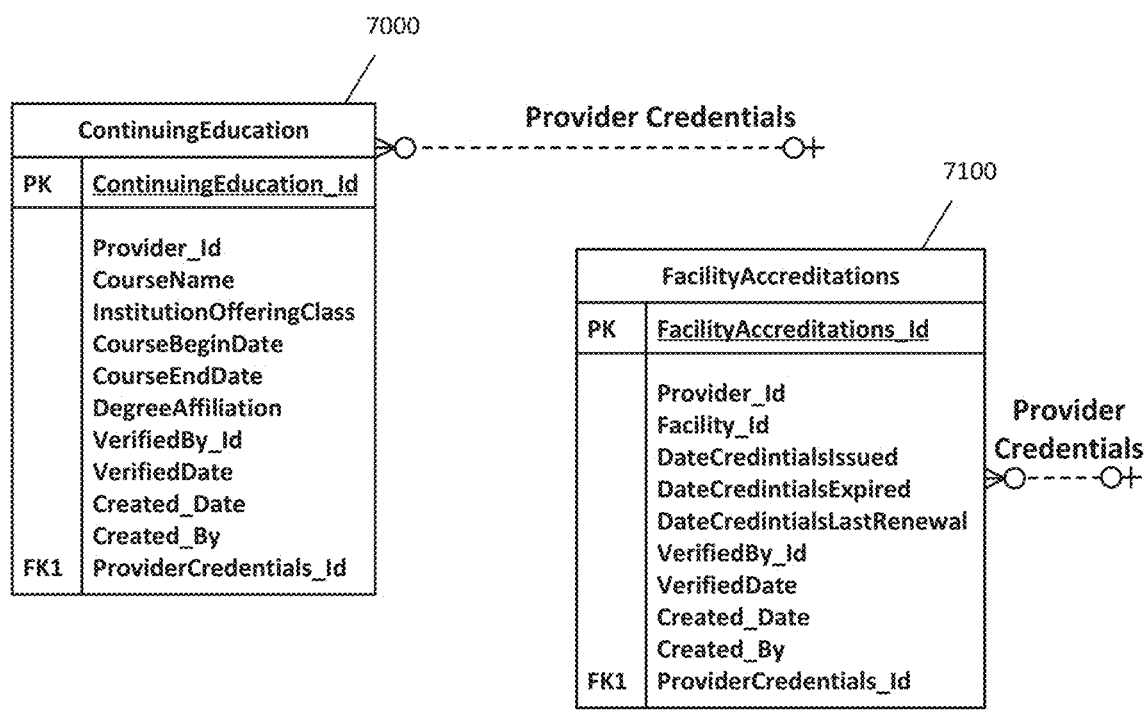
FIG. 25N depicts the PTO_Saver ContinuingEducation and FacilityAccreditations tables.

FIG. 25N depicts PTO_Saver ContinuingEducation table 7000, which has a primary key of Continuing Education_Id, Provider_Id, CourseName, InstitutionOfferingClass, CourseBeginDate, CourseEndDate, DegreeAffiliation, Verified_By_Id, VerifiedDate, Created_By, Created_Date, and a first foreign key of ProviderCredentials_Id. ContinuingEducation table 7000 communicates with Provider_Credentials table 7200. FacilityAccreditations table 7100 has a primary key of FacilityAccreditations_Id, Provider_Id, Facility_Id, DateCredentialsIssued, DateCredentialsExpired, DateCredentialsLastRenewal, VerifiedBy_Id, VerifiedDate, Created_Date, Created_By, and ProviderCredentials_Id as a first foreign key from Provider_Credentials table 7200.

Figure 25O:
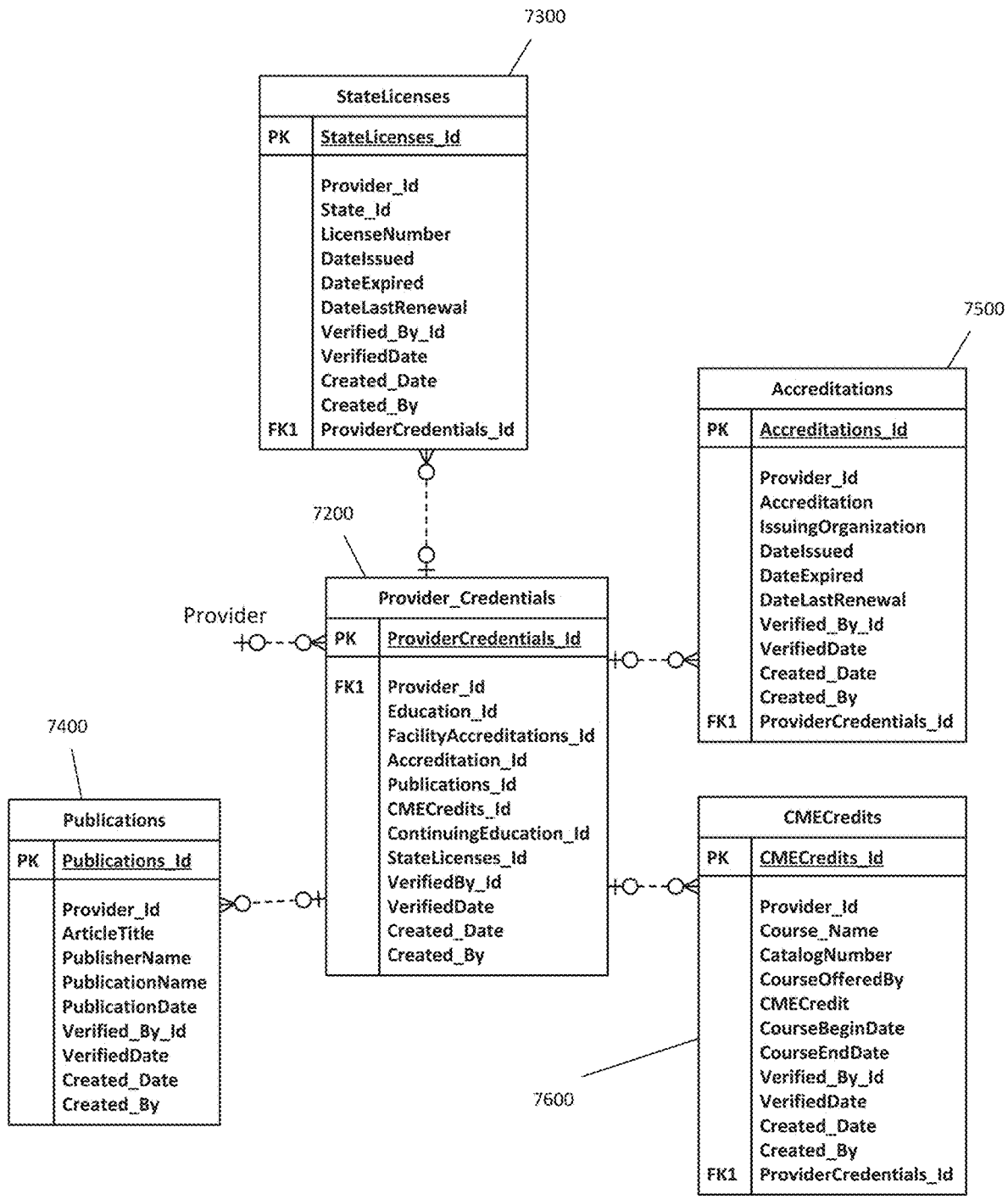
FIG. 25O depicts the PTO_Saver StateLicenses, Publications, Accreditations, ProviderCredentials, and CMECredits tables.

FIG. 25O depicts PTO_Saver Provider_Credentials table 7200, which has a primary key of ProviderCredentials_Id, a first foreign key of Provider_Id, Education_Id, FacilityAccrediation_Id, Accrediations_Id, Publications_Id, CMECredits_Id, ContinuingEducation_Id, StateLicenses_Id, VerifiedBy_Id, VerifiedDate, Created_Date, and Created_By. Publications table 7400 has a primary key of Publications_Id, a Provider_Id, ArticleTitle, PublisherName, PublicationName, PublicationDate, Verified By_Id, Created_Date, and Created_By. StateLicenses table 7300 has a primary key of StateLicenses_Id, Provider_Id, State_Id, LicenseNumber, DateIssued, DateExpired, DateLastRenewal, Verified_By_Id VerifiedDate, Created_Date, Created_By, and a first foreign key of ProviderCredentials_Id. CMECredits table 7600 has primary key of CMECredits_Id, Provider_Id, Course_Name, CatalogNumber, CourseOfferedBy, CMECredit, CourseBeginDate, CourseEndDate, Verified_By_Id, VerifiedDate, Created_Date, Created_By, and a first foreign key of ProviderCredentials_Id. Accreditations table 7500 has primary key of Accrediations_Id, Provider_Id, Accreditation, IssuingOrganization, DateIssued, DateExpired, DateLastRenewal, Verified_By_Id, VerifiedDate, Created_Date, Created_By, and a first foreign key of ProviderCredentials_Id. StateLicenses table 7300, Publications table 7400, Accreditations table 7500, and CMECredits table 7600 all have many to one relationships to Provider_Credentials table 7200, which communicates with Provider table 8400.

Figure 25P:
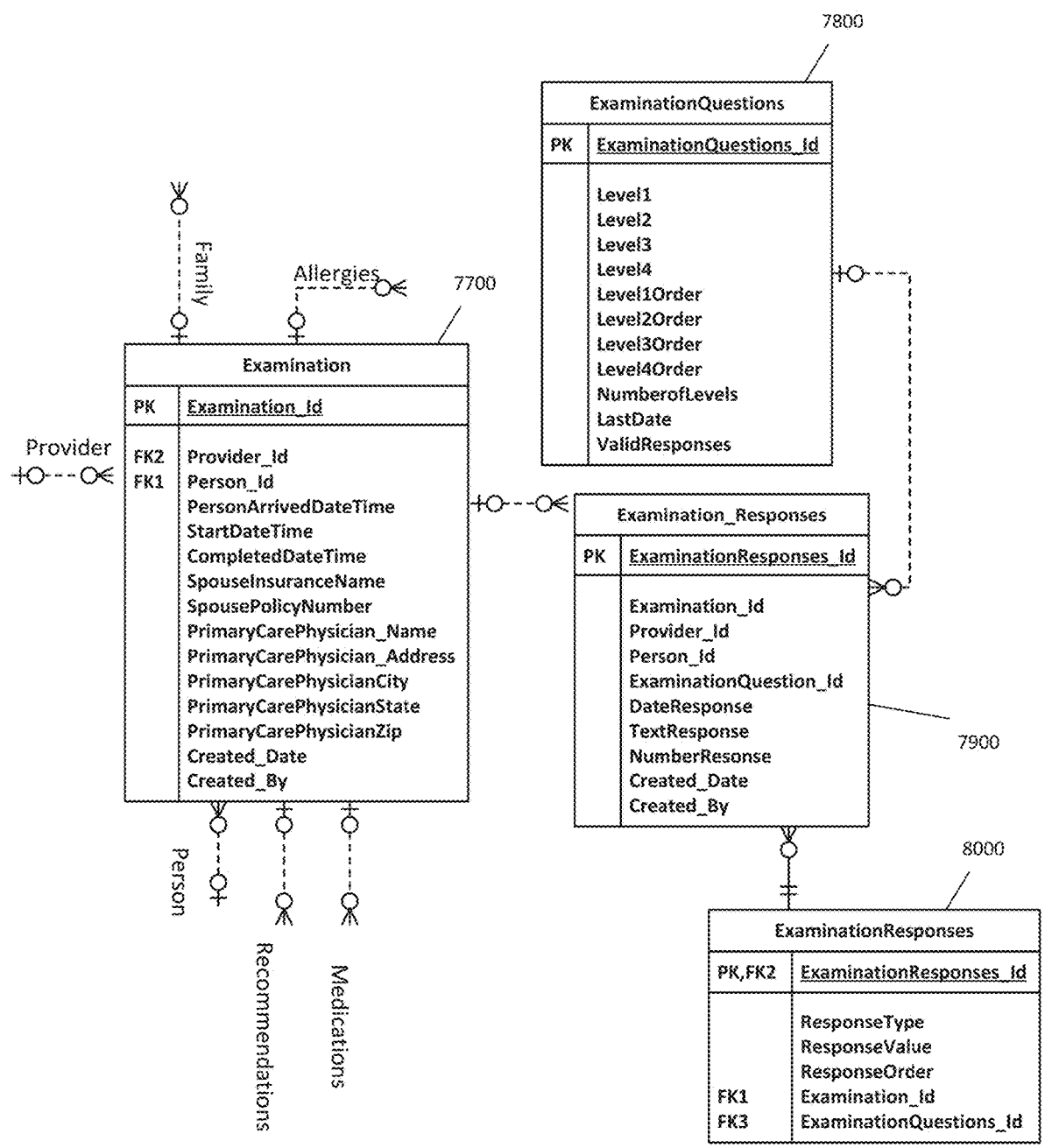
FIG. 25P depicts the PTO_Saver Examination, ExaminationQuestions, and ExaminationResponses tables.

FIG. 25P depicts PTO Saver Examination table 7700, which has as a primary key Examination_Id, a second foreign key of Provider_Id, and a first foreign key of Person_Id, with data feeds of Provider table 8400, Allergies table 8300, Medications table 6700, and Recommendations table 6800. Examination table 7700 also has PersonArrivedDateTime, StartDateTime, CompletedDateTime, SpouseInsuranceName, SpousePolicyNumber, PrimaryCarePhysician_Name, PrimaryCarePhysician_Address, PrimaryCarePhysicianCity, PrimaryCarePhysicianState, PrimaryCarePhysicianZip, Created_Date, and Created_By. Examination table 7700 either receives or sends data to ExaminationResponses table 7900, which has a primary key and a second foreign key of ExaminationResponses_Id, and has ResponseType, ResponseValue, ResponseOrder, Examination_Id as a first foreign key, and ExaminationQuestions_Id as a third foreign key. ExaminationQuestions table 7800 relates to ExaminationResponses table 7900. ExaminationQuestions table 7800 has Level1, Level2, Level3, Level4, Level1Order, Level2Order, Level3Order, Level4Order, Number of Levels, LastDate, and ValidResponses. Examination_Responses table 7900 has a primary key of ExaminationResponses_Id, Examination_Id, Provider_Id, Person_Id, ExaminationQuestion_Id, DateResponse, TextResponse, NumberResponse, Created_Date, and Created_By. Examination_Responses table 8000 has a primary key and second foreign key of ExaminationResponses_Id, with ResponseType, ResponseValue, ResponseOrder, Examination_Id as a first foreign key, and ExaminationQuestions_Id as a third foreign key.

Figure 25Q:
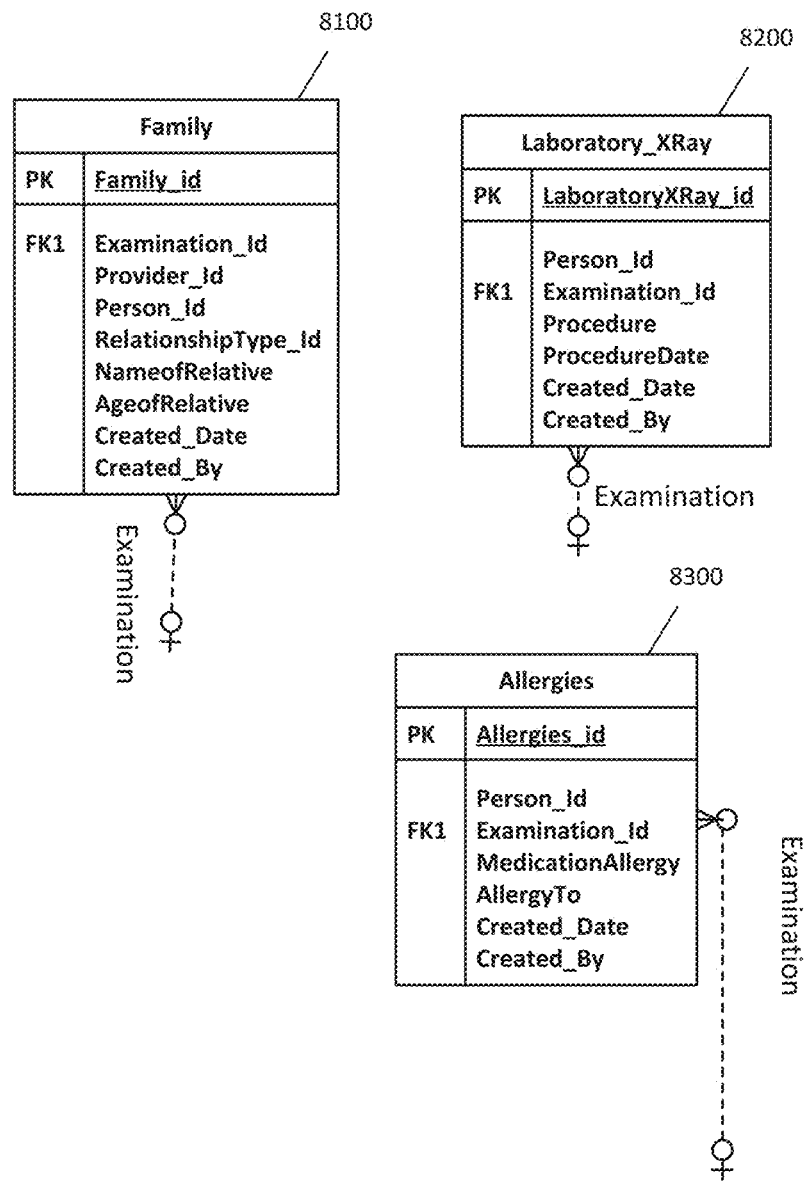
FIG. 25Q depicts the PTO_Saver Family, Laboratory XRay, and Allergies tables.

FIG. 25Q depicts PTO_Saver Family table 8100, which has Family_Id as a primary key, Examination_Id as a first foreign key, Provider_Id, Person_Id, RelationType_Id, NameofRelative, AgeofRelative, Created_Date, and Created_By. Also shown is Laboratory XRay table 8200, with a primary key of LaboratoryXRay_Id, Person_Id, a first foreign key of Examination_Id, Procedure, ProcedureDate, Created_Date, and Created_By 5026. Also shown is Allergies table 8300, with a primary key of Allergies_Id, Person_Id, a first foreign key of Examination_Id, a MedicationAllergy, an AllergyTo, Created_Date, and Created_By. Family table 8100, Laboratory XRay table 8200, and Allergies table 8300 each send and receive data to and from Examination table 7700.

Figure 25R:
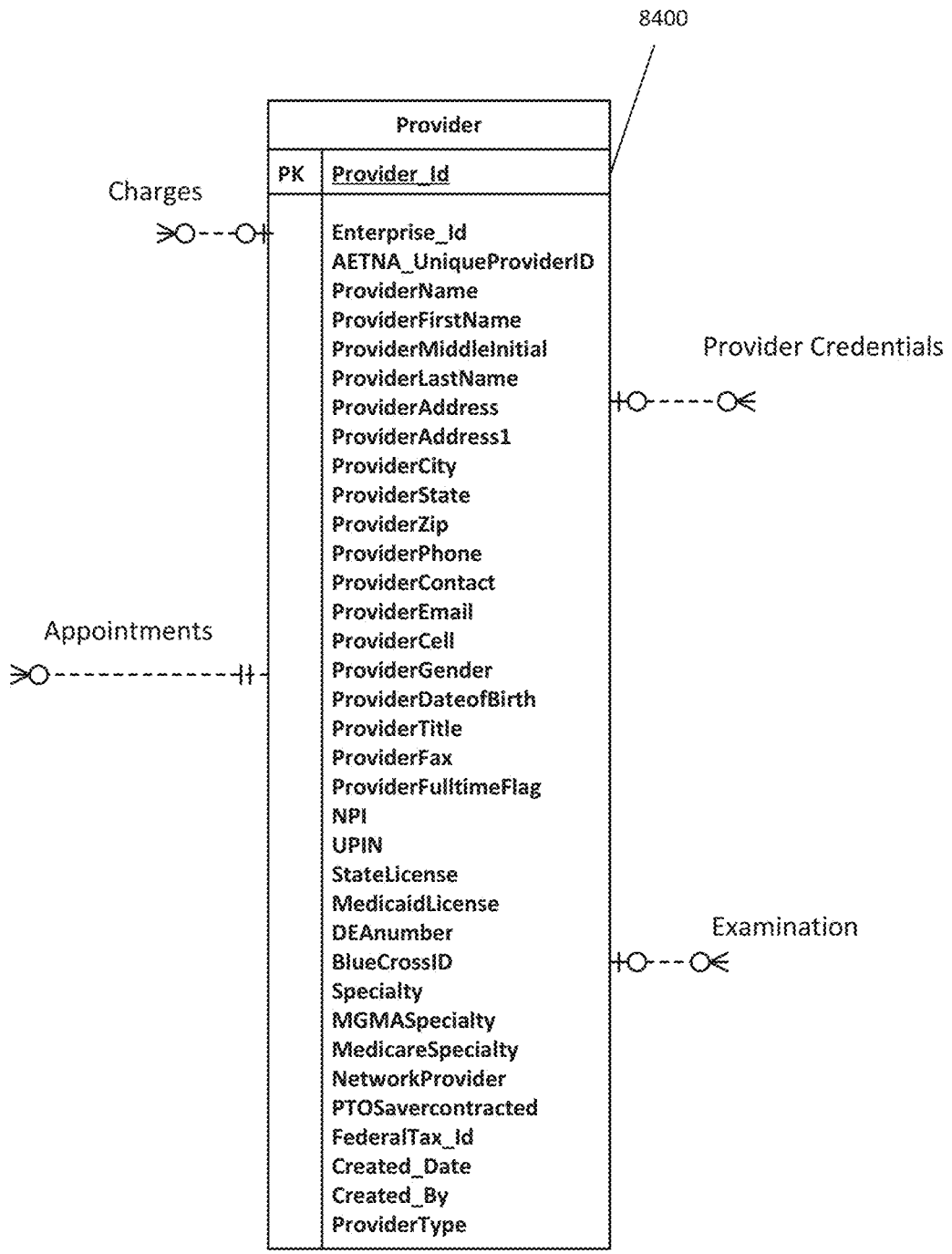
FIG. 25R depicts the PTO_Saver Provider table.

FIG. 25R depicts PTO_Saver Provider table 8400, which has a primary key of Provider_Id, an Enterprise_Id, an AETNA UniqueProviderID, ProviderName, ProviderFirstName, ProviderMiddleInitial, ProviderLastName, ProviderAddress, ProviderAddress1, ProviderCity, ProviderState, ProviderZip, ProviderPhone, ProviderContact, ProviderEmail, ProviderCell, ProviderGender, ProviderDateofBirth, ProviderTitle, ProviderFax, ProviderFullTimeFlag, NPI, UPIN, StateLicense, MedicaidLicense, DEAnumber, BlueCrossID, Specialty, MGMASpecialty, MedicareSpecialty, NetworkProvider, PTOSavercontracted, FederalTax_Id, Created_Date, Created_By, and ProviderType. Provider table 8400 communicates with Appointment table 8500, Charges table 4000, Examination table 7700, and Provider Credentials table 7200.

Figure 25S:
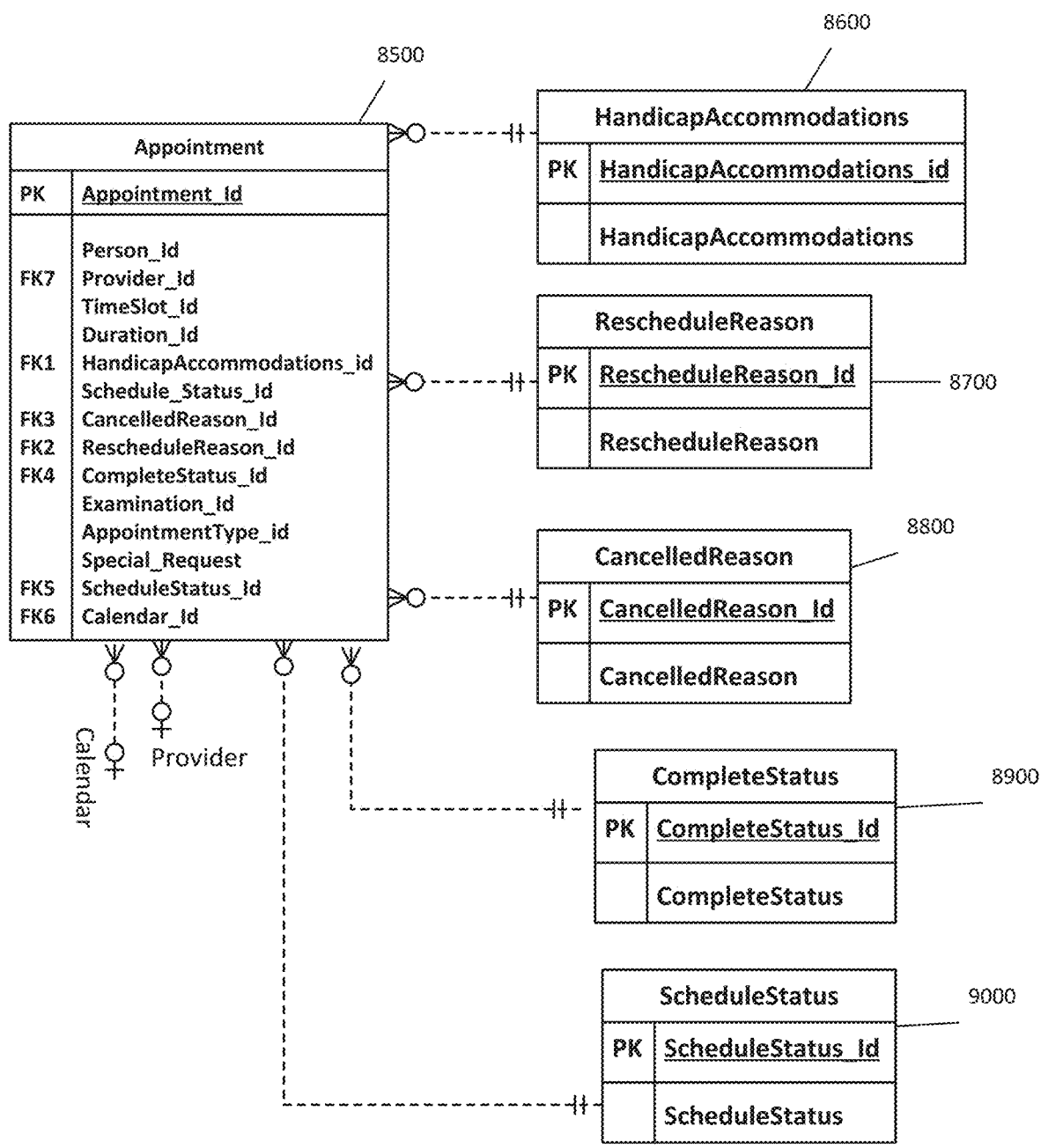
FIG. 25S depicts the PTO_Saver Appointment, HandicapAccommodations, RescheduleReason, CancelledReason, CompleteStatus, and ScheduleStatus tables.

FIG. 25S depicts PTO_Saver Appointment table 8500, which has a primary key of Appointment_Id, Person_Id, a seventh foreign key of Provider_Id, TimeSlot_Id, Duration_Id, HandicapAccommodation_Id as a first foreign key, Schedule_Status_Id, CancelledReason_Id as a third foreign key, RescheduledReason_Id as a second foreign key, CompletedStatus_Id as a fourth foreign key, Examination_Id, AppointmentType_Id, SpecialRequest, Schedule Status_Id as a fifth foreign key, and Calendar_Id as a sixth foreign key. Appointment table 8500 relates and communicates with Provider table 8400, Calendar table 9800, and HandicapAccommodations table 8600. HandicapAccommodations table 8600 has a primary key of HandicapAccommodations_Id and an object HandicapAccommodations. Appointment table 8500 communicates and relates to RescheduleReason table 8700, which has a primary key of RescheduleReason_Id and an object RescheduleReason. Appointment table 8500 communicates with CancelledReason table 8800, which has a primary key of CancelledReason_Id and an object CancelledReason. Appointment table 8500 communicates with and relates to CompleteStatus table 8900, which has a primary key of CompleteStatus_Id and an object CompleteStatus. Appointment table 8500 communicates and relates to ScheduleStatus table 9000, which has a primary key of ScheduleStatus_Id and an object ScheduleStatus.

Figure 25T:
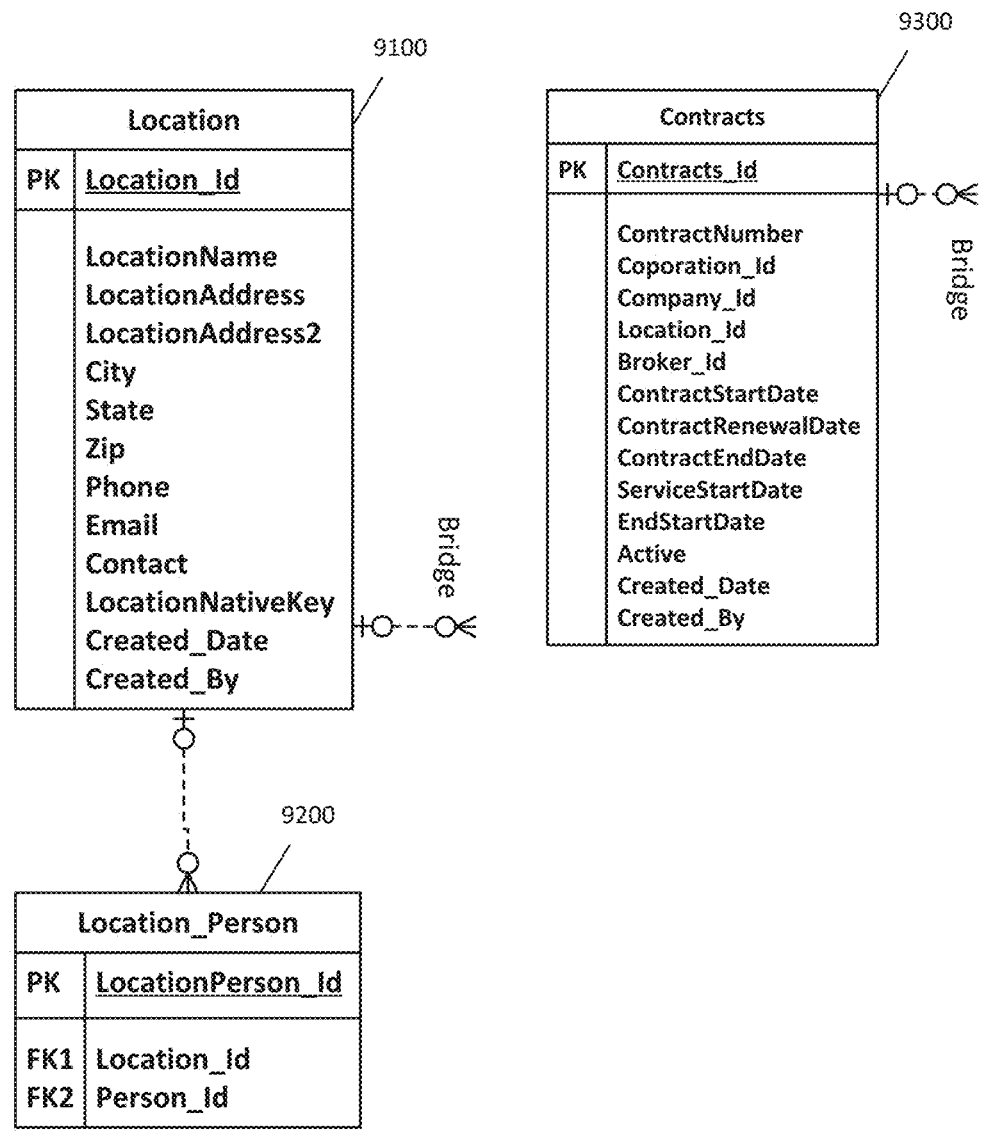
FIG. 25T depicts the PTO_Saver Contracts, Location_Id, and Location_Person tables.

FIG. 25T depicts PTO_Saver Contracts table 9300, which has a primary key of Contracts_Id, ContractNumber, Corporation_Id, Company_Id, Location_Id, Broker_Id, ContractStartDate, ContractRenewDate, ContractEndDate, ServiceStartDate, EndStartDate, Active, Created_Date, and Created_By. Location table 9100 has a primary key of Location_Id, LocationName, LocationAddress, LocationAddress2, LocationCity, LocationState, LocationZip, LocationPhone, LocationEmail, LocationContact, LocationNativeKey, Created_Date, and Created_By. Contracts table 9300 and Location table 9100 both communicate with Bridge table 9400 and Corporation table 9400. Location_Person table 9200 has a primary key of Location_Person_Id, a first foreign key of Location_Id, and a second foreign key of a Person_Id. Location_Person table 9200 communicates with Person table 10600.

Figure 25U:
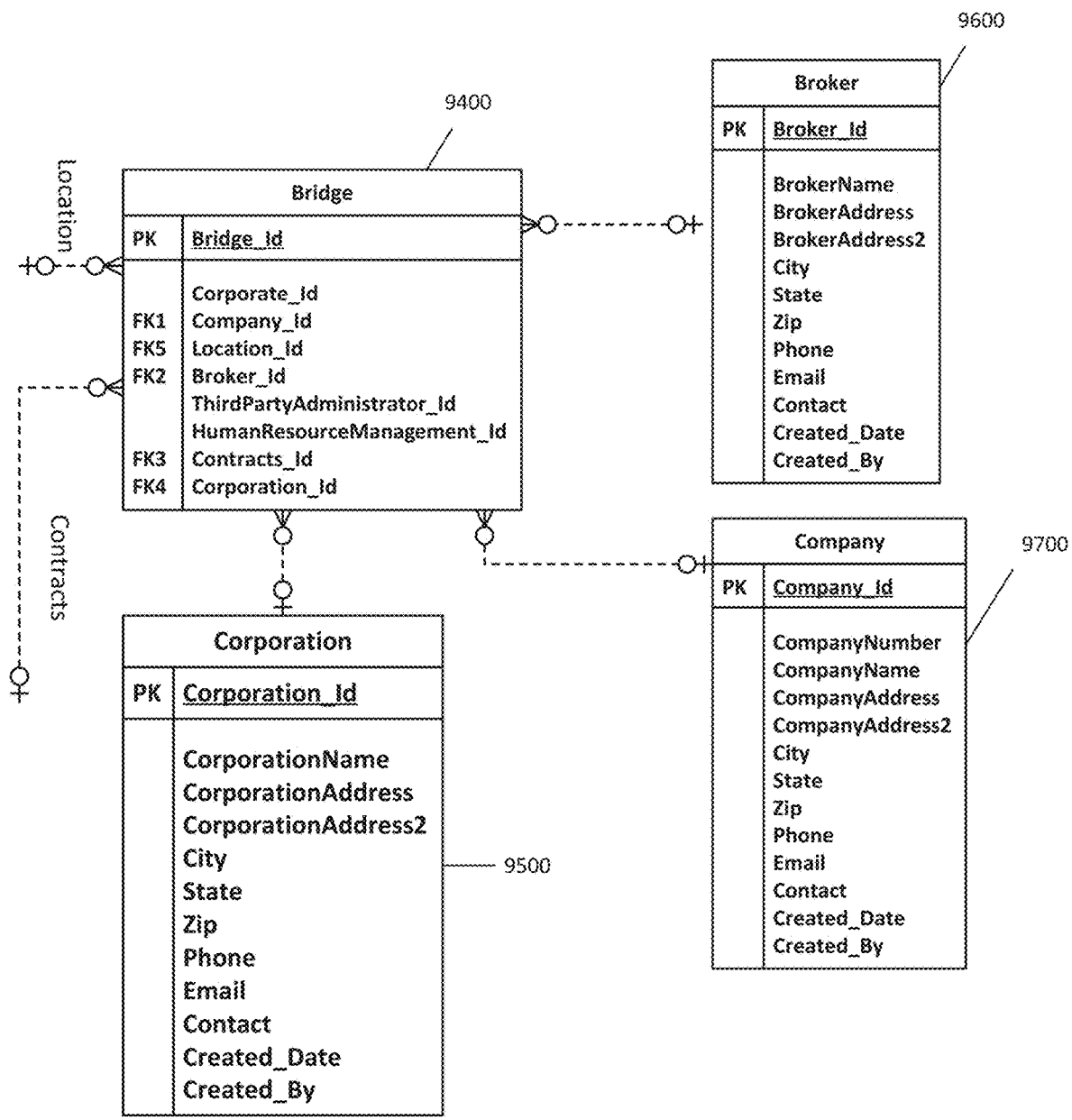
FIG. 25U depicts the PTO_Saver Bridge, Corporation, Broker, and Company tables.

FIG. 25U depicts PTO_Saver Bridge table 9400, which communicates with Contracts table 9300 and has a primary key of Bridge_Id, Corporate_Id, Company_Id as a first foreign key, Location_Id as a fifth foreign key, Broker_Id as a second foreign key, ThirdPartyAdministrator_Id, HumanResourcesManagement_Id, Contracts_Id as a third foreign key, and Corporation_Id as a fourth foreign key. Corporation table 9500 has the primary key of Corporation_Id, CorporationName, CorporationAddress, CorporationAddress, CorporationAddress2, CorporationCity, CorporationState, CorporationZip, CorporationPhone, CorporationEmail, CorporationContact, Created_Date, and Created_By. Broker table 9600 has a primary key of Broker_Id, BrokerName, BrokerAddress, BrokerAddress2, BrokerCity, BrokerState, BrokerZip, BrokerPhone, BrokerEmail, BrokerContact, Created_Date, and Created_By. Company table 9700 has a primary key of Company_Id, CompanyNumber, Company- Name, CompanyAddress, CompanyAddress2, City, State, Zip, Phone, Email, Contact, Created_Date, and Created_By.

Figure 25V:
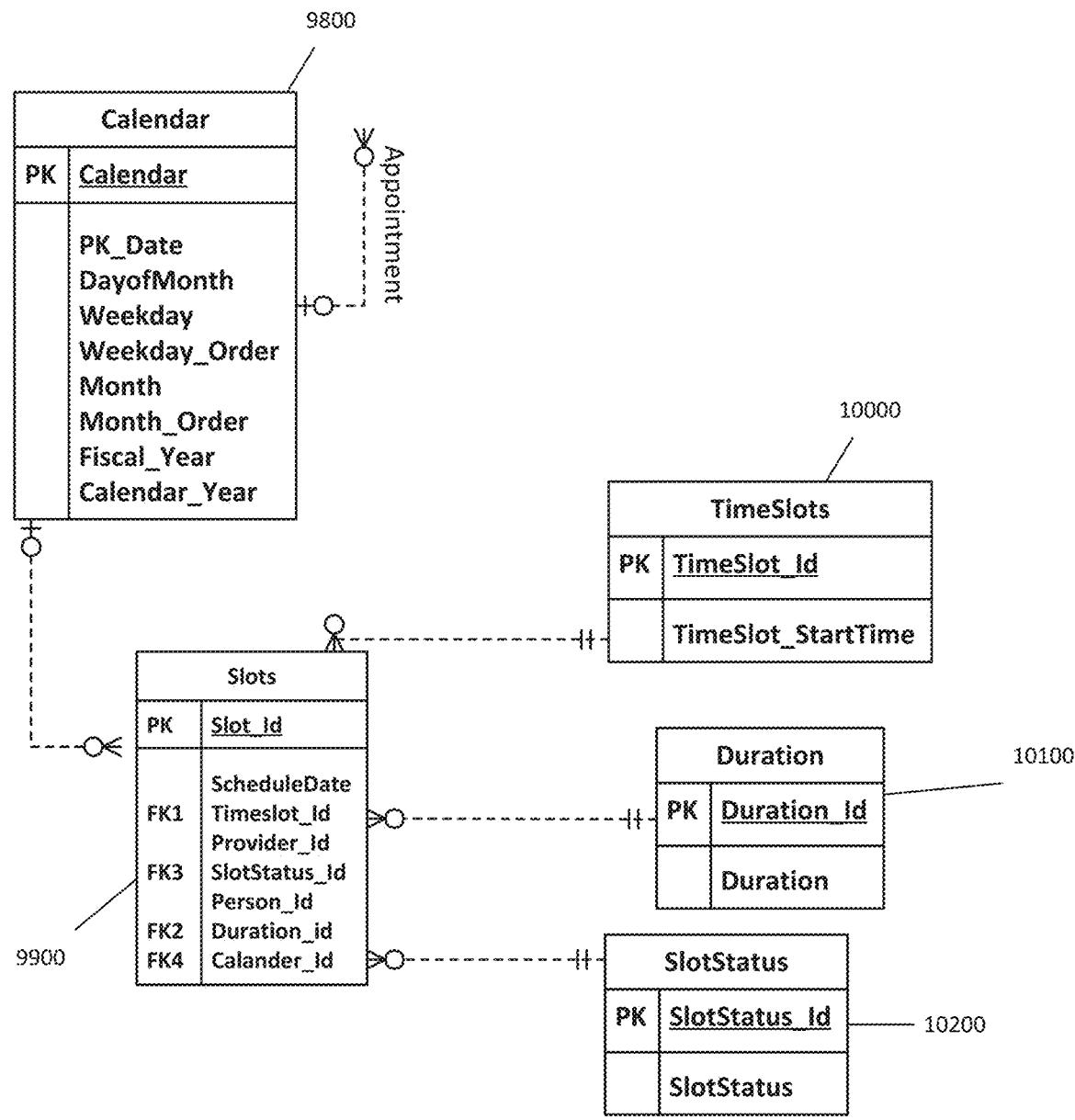
FIG. 25V depicts the PTO_Saver Calendar, Slots, Duration, SlotStatus and Time Slots tables.

FIG. 25V depicts PTO Calendar table 9800, which communicates with Appointment table 8500 and Slots table 9900, and has Calendar_Id as a primary key, PK_Date (i.e., Primary Key Date), DayofMonth, WeekDay, Weekday_Order, Month, Month_Order, Fiscal_Year, and Calendar_Year. Calendar table 9800 has output and input from Appointment table 8500 and to Slots table 9900. Slots table 9900 has a primary key of Slot_Id, ScheduleDate, a first foreign key of TimeSlot_Id, a Provider_Id, a third foreign key of SlotStatus_Id, Person_Id, second foreign key of Duration_Id, and a fourth foreign key Calendar_Id. Slots table 9900 communicates with TimeSlots table 10000, Duration table 10100, and SlotStatus table 10200 in a many to one relationship. TimeSlots table 10000 has a primary key of TimeSlot_Id and a TimeSlot_StartTime. Slots table 9900 further communicates with Duration table 10100, which has a primary key of Duration_Id and Duration as an object. Slots table 9900 further communicates with SlotStatus table 10200, which has a primary key of SlotStatus_Id and an object of SlotStatus.

Figure 25W:
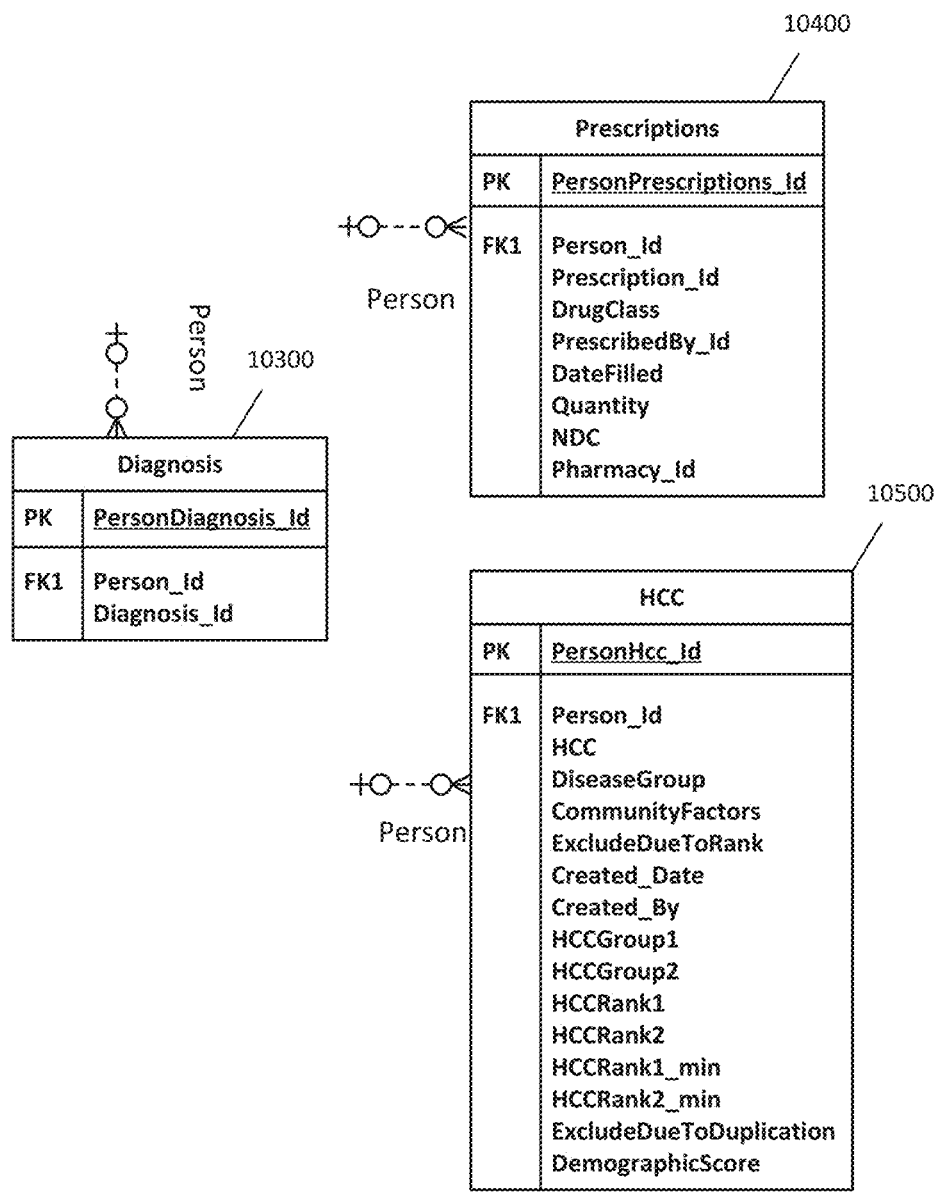
FIG. 25W depicts the PTO_Saver HCC, Diagnosis, and Prescriptions tables.

FIG. 25W depicts Diagnosis table 10300, which has a primary key of PersonDiagnosis_Id, a first foreign key of Person_Id, and Diagnosis_Id. Diagnosis table 10300 communicates with Person table 10600. Prescriptions table 10400 and HCC table 10500 both relate to and communicate with Person table 10600. Prescriptions table 10400 has a primary key of PersonPrescriptions_Id, a first foreign key of Person_Id, Prescription_Id, DrugClass, PrescribedBy_Id, DateFilled, Quantity, NDC, and Pharmacy_Id. HCC table 10500 has a primary key of PersonHcc_Id, a first foreign key of Person_Id, HCC, DiseaseGroup, CommunityFactors, ExcludeDueToRank, Created_Date, Created_By, HCC-Group1, HCCGroup2, HCCRank1, HCCRank2, HCCRank1_min, HCCRank2_min, ExcludeDueToDuplication, and DemographicScore.

Figure 25X:
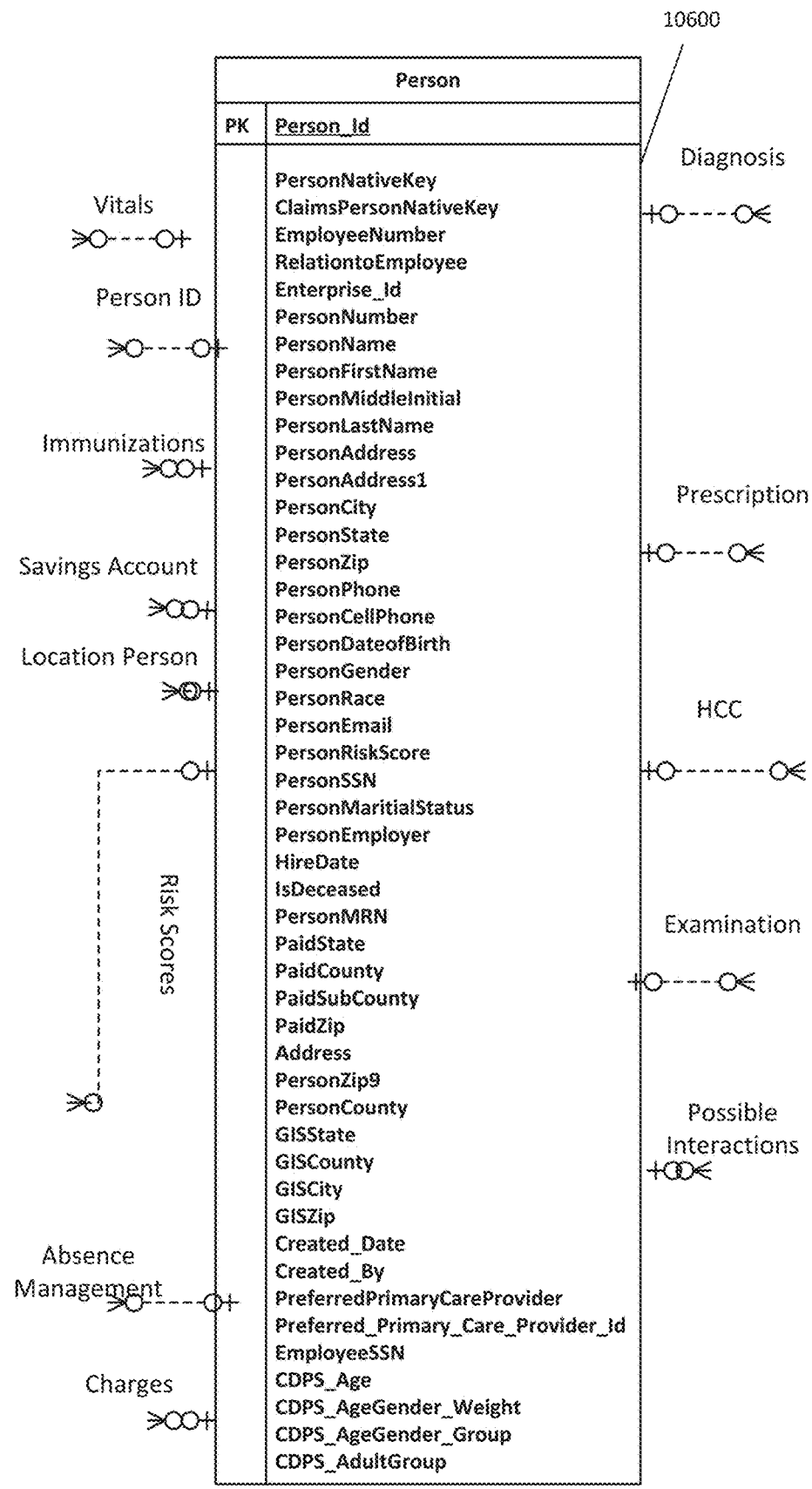
FIG. 25X depicts the PTO-Saver Person table.

FIG. 25X depicts PTO_Saver Person table 10600, identifying the information relative to the system and a person. Person table 10600 has a primary key of Person_Id, PersonNativeKey, ClaimsPersonNativeKey, EmployeeNumber, RelationToEmployee, Enterprise_Id, PersonNumber, PersonName, PersonFirstName, PersonMiddleName, PersonLastName, PersonAddress, PersonAddress1, PersonCity, PersonState, PersonZip, PersonPhone, PersonCellPhone, PersonDateofBirth, PersonGender, PersonRace, PersonEmail, Person RiskScore, PersonSSN, PersonMarital Status, PersonEmployer, HireDate, IsDeceased, PersonMRN, Paid-State, PaidCounty, PaidSubCounty, PaidZip, Address, PersonZip9, PersonCounty, GISState, GISCounty, GISCity, GISZip, Created_Date, Created_By, PreferredPrimaryCare-Provider, Preferred_Primary_Care_Provider_Id, EmployeeSSN, CDPS_Age, CDPS_AgeGender_Weight, CDPS_AgeGender_Group, and CDPSAdultGroup. The PTO_Saver Person table 10600 communicates with SavingsAccount table 5600, Position table 5700, PersonPlan table 6100, Charges table 4000, Vitals table 5000, Immunizations table 5900, LocationPerson table 9200, AbsenceManagement table 5200, MedicalConditions table 6200, RiskScores table 6500, PossibleInteractions table 6600, Examination table 7700, HCC table 10500, Prescriptions table 10400, and Diagnosis table 10300.

FIG. 25Y depicts a legend for symbols used in FIGS. 25A-25X.

Figure 26:
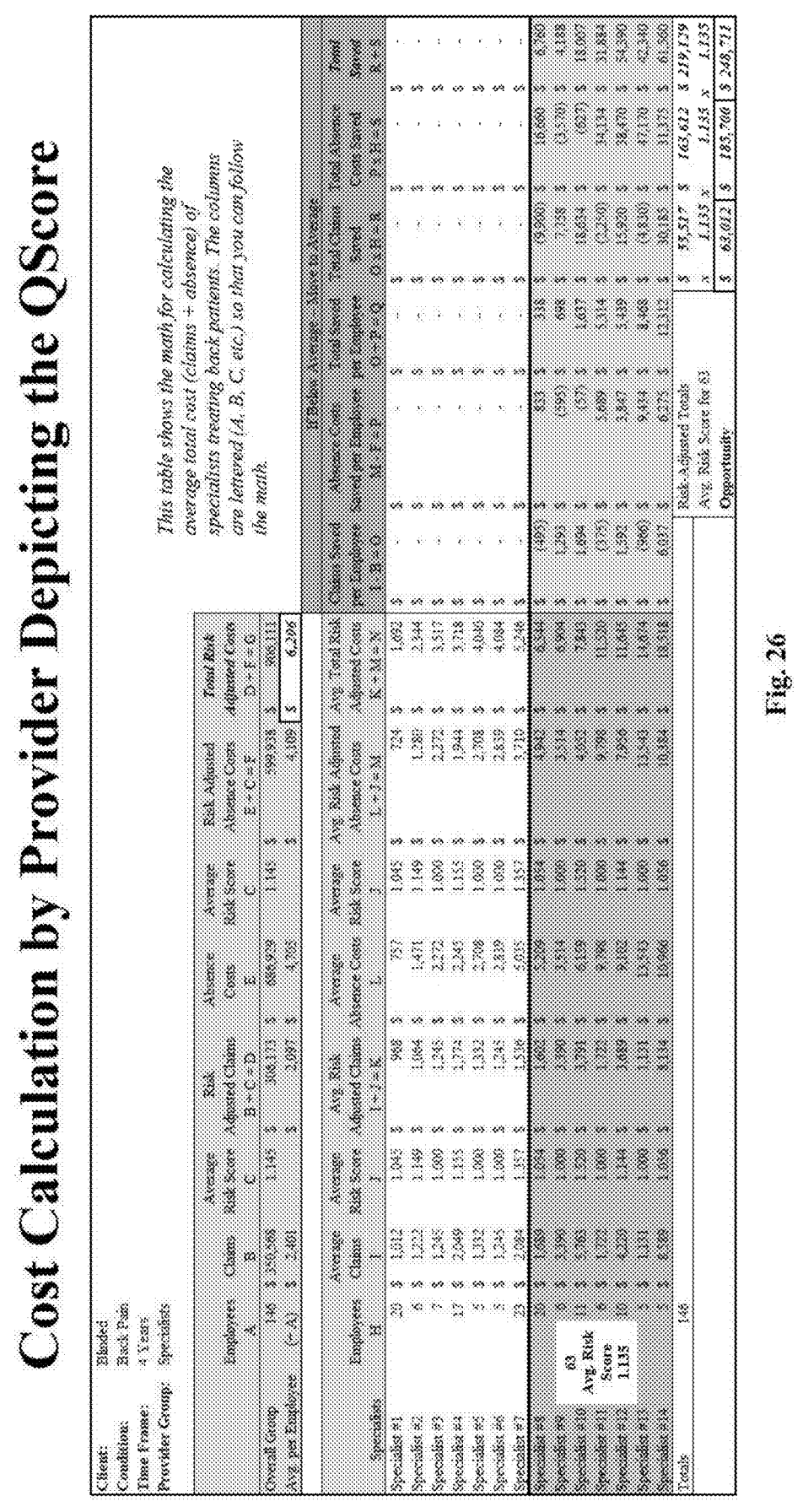

FIG. 26 depicts an example of the quantifying of healthcare outcomes and calculation of QScores for specialists treating back patients using data accumulated over four years. The columns in the table are lettered (A, B, C, etc.) to enable following the math.

The middle of the table shows the averages for the 146 employees in the data set (Column A). The total medical and pharmacy claims related to the back diagnosis for these 146 employees was $350,568 (Column B), making the average per employee $2,401 ($350,568÷146=$2,401).

Risk scoring of the employees is required to normalize the results across the providers and level the playing field so that providers treating sicker patients are not penalized. The average risk score for the 146 employees was 1.145. Under the risk scoring system an individual of average health receives a risk score of 1.000, an individual healthier than average a risk score below 1.000 (the lower, the healthier), and an individual sicker than average a risk score above 1.000 (the higher, the sicker). When calculating this average, individuals with risk scores below 1.000 are assigned a normalized risk score of 1.000. Any number of risk scoring systems may be used so long as they are demographically appropriate for the population. Risk scoring systems evaluate an individual's health based on several factors, which may include the individual's age, gender and comorbidities as determined by examining the individual's medical and pharmacy claims. Open-source risk-scoring systems include HHS-HCC (Department of Health and Human Services—Hierarchical Condition Categories), CDPS (Chronic Illness & Disability Payment System), or CMS-HCC (Centers for Medicare & Medicaid Services—Hierarchical Condition Categories). HHS-HCC and CDPS are appropriate for working age populations, while CMS-HCC is appropriate for retired ones. In addition, the engine may adjust the risk scores with certain social determinants of health (SDOH), job demographics, and health plan/clinical data. SDOH include a person's ZIP code (which may indicate the person's access to healthy food) and compensation (which may indicate the person's ability to pay for healthcare). Job demographics include a person's job description (and from that, the physicality required by their position), position rank, tenure, and compensation (including hourly versus salary and part-time versus full-time). Health plan/clinical data include the type of health plan that the person has enrolled in (e.g., HMO—Health Maintenance Organization, PPO—Preferred Provider Organization or HDHP—High Deductible Health Plan) and clinical variables such as height, weight, and the results of any health assessments or evaluations.

The claims are then divided by the risk score to determine the risk-adjusted claims, a total of $306,173 and an average of $2,097 (B÷C=D).

Next the employee absence costs related to those claims are determined by juxtaposing the dates of the claims against the employer's employee absence records (sick days or PTO—Paid Time Off). For example, if an employee has a hospital claim dated Day #1, then the PTO day that the employee took on Day #1 (and possibly a certain number of days thereafter) is related to that claim. Such medically-related absence costs are then valued at the employee's compensation rate or a normalized rate for all employees. The absence costs so determined that were related to the medical and pharmacy claims were a total of $686,929, with an average of $4,705 per employee (Column E). These absence costs are then divided by the average risk score to get the risk-adjusted absence costs of $599,938 in total, or $4,109 per employee (E÷C=F).

The risk-adjusted claims and risk-adjusted absence costs are then added together to obtain the group's average total risk-adjusted costs of $906,111 in total, or a group average of $6,206 per employee (D+F=G).

The balance of FIG. 26 shows the calculations for each of the 14 specialists treating the 146 employees. These specialists are listed according to their average total risk-adjusted cost per employee, with the specialist with the lowest average risk-adjusted cost on top, and the specialist with the highest average risk-adjusted cost on the bottom. The dark line between Specialist #7 and Specialist #8 separates specialists doing better than average who are above the line (their average risk-adjusted cost per employee is less than the group average of $6,206) from specialists doing worse than average (their average risk-adjusted cost per employee is more than the group average of $6,206).

For example, Specialist #14 on the bottom row treated five employees (Column H). The average medical and pharmacy claims for each of these employees was $8,589 (Column I). Note that when allocating claims and absence costs to a provider that the engine allocates to them all the costs for which they are responsible, both their direct costs and the indirect downstream costs from their referrals. This allows the engine to evaluate a provider's referral patterns, which is particularly useful when evaluating PCPs (Primary Care Physicians) who often refer patients to specialists and surgeons. The average risk score of the five employees is 1.056 (Column J), making the average risk-adjusted claims $8,134 (I÷J=K).

The average absence costs for the five employees was $10,966 (Column L), which when divided by the average risk score (Column J) makes the average risk-adjusted absence costs $10,384 (L÷J=M). Adding the average risk-adjusted claims cost (Column K) to the average risk-adjusted absence cost (Column M) gives Specialist #14's average risk-adjusted total cost to treat a back patient of $18,518 (K+M=N), three times the group average of $6,206 (Column G).

To quantify the magnitude of the opportunity for cost savings and care improvement, the remaining columns calculate what would happen if the employees going to worse than average specialists (below the line between Specialist #7 and Specialist #8) were moved to the average of $6,206, not to one of the best specialists on the top, but just to the average. Note that this example uses the group average to quantify this savings opportunity. The engine can perform this determination using any base, such as moving patients to providers at the $75^{th}$ percentile or $90^{th}$ percentile. The average ($50^{th}$ percentile) is given as an example.

Continuing with Specialist #14, the risk-adjusted claims per employee that would be saved by moving that specialist's patients to the average would be $6,037 (I−B=O), and the risk-adjusted absence costs per employee that would be saved would be $6,275 (M−F=P), making the total risk-adjusted savings per employee $12,312 (O+P=Q). The total savings on all five employees would be $61,560 (see Columns R, S and the last column which adds them together).

There were a total of 63 employees going to specialists who were worse than average (Specialists #8-Specialist #14), with an average risk score of 1.135. As shown in the bottom right corner, moving these 63 employees to the group average of $6,206 would save $219,129 risk-adjusted dollars. As these are risk-adjusted dollars (they have been divided by the risk scores) to determine the real savings opportunity requires multiplying them by the average risk score of 1.135 of the 63 employees being moved, resulting in a total savings opportunity of $248,711. Note that this savings opportunity is calculated on the employees only. Although the rankings are determined using only employee data, the rankings can be used to move both employees and non-employees alike to the better providers so that the actual savings would be even more.

The navigation engine organizes the medical and pharmacy claims under an employer's health plan (or other program) in tables with various headers that enable filtering, grouping and matching.

The navigation engine also organizes the human resource records of the employer (or other records) relating to employee absence, job category and payroll in tables that enable filtering, grouping and matching.

Root diagnoses for each patient's claims are identified. A "root diagnosis" is the patient's main problem from which all related claims emanate.

All a patient's claims related to a root diagnosis are grouped together over the entire continuum of care. The continuum of care for a chronic condition is a specified period, while the continuum of care for an episodic condition is from the first claim in the episode to the last (bookmarked by certain temporal constraints).

Absences related to an employee's root diagnosis are identified by juxtaposing the dates for all the claims grouped under that root diagnosis against the employee's absence records and identifying time off related to the claims based on temporal proximity.

Identified absences are valued at the employee's pay rate or a normalized rate.

These absence costs are not only a cost to the employer, but also measure the quality of care received by the employee because the quicker the employee returned to work, the more effective the care was. This novel use of absence costs to measure healthcare quality quantifies quality, which has never been done before in healthcare.

For each root diagnosis for an employee, all the claims and absence costs are combined to obtain the total cost of the care.

A risk score is determined for each patient using age, gender, disease and pharmaceutical data contained in the claims and/or human resource records. If a patient's risk score is 1.000 (an individual of average health) or below 1.000 (an individual healthier than average) a risk score of 1.000 is assigned. If the patient's risk score is above 1.000 (an individual sicker than average), the patient's actual risk score is used.

A numerical job factor is created for each employee based on that employee's job category. Elements that weigh on that factor include the physical exertion that the job requires, time spent standing versus sitting, repetitive stress movements, and the emotional, mental and physical stress of the job.

The providers (physicians, hospitals, etc.) and other Healthcare Items_whose outcomes are to be quantified are organized in tables that enable filtering, grouping and matching.

Each provider that filed a claim grouped with an employee's root diagnosis is allocated both: (1) that provider's claims grouped with that root diagnosis and the related absence costs; and (2) all "downstream" claims and related absence costs from direct and indirect referrals of the employee made by that provider to other providers. Note that if all the costs of all the providers were added together that this would result in double, triple counting, etc., although for ranking purposes it doesn't matter. For example, if a PCP treated an employee and then referred the employee to a specialist, that PCP's costs would be not only the claims and absence costs related to the PCP's treatment, but all the specialist's claims and absence costs too. In addition, the specialist's claims and absence costs would be attributed to the specialist, along with any downstream costs of further referrals (which would also be included in the PCP's costs).

Allocating downstream costs back to the referring physician enables evaluation of the physician's referral patterns, which is essential when determining the outcomes that a provider achieves.

The Healthcare Items whose outcomes are being quantified are sorted into categories and sub-categories and displayed as such in the navigation interface. For example, providers may be sorted into: (1) PCPs (including physician assistants and nurse practitioners); (2) Non-Surgeon Specialists; (3) Surgeons; and (4) Institutions (e.g., hospitals, out-patient surgery centers, etc.).

The average risk and job adjusted cost to treat an employee with a particular root diagnosis is determined. For example, when doing so for providers by: (1) combining all the employee claims and absence costs attributed to that provider when treating that root diagnosis (including downstream costs); (2) dividing those total costs by the average risk score of the employees treated, (3) dividing that resulting quotient by the average job factor of the employees treated (alternatively, the job factor may be applied to only the absence costs), and (4) dividing that resulting quotient by the number of employees treated.

When making these calculations, the data of employers in the same geographic area may be pooled if their employees are going to most of the same providers.

The Healthcare Items whose outcomes are being quantified, such as the providers in each category, are then ranked for each root diagnosis based on their average risk and job adjusted costs (claims plus absence costs to return an employee with that condition to work)—from the best with the lowest average cost, to the worst with the highest.

Figure 27:
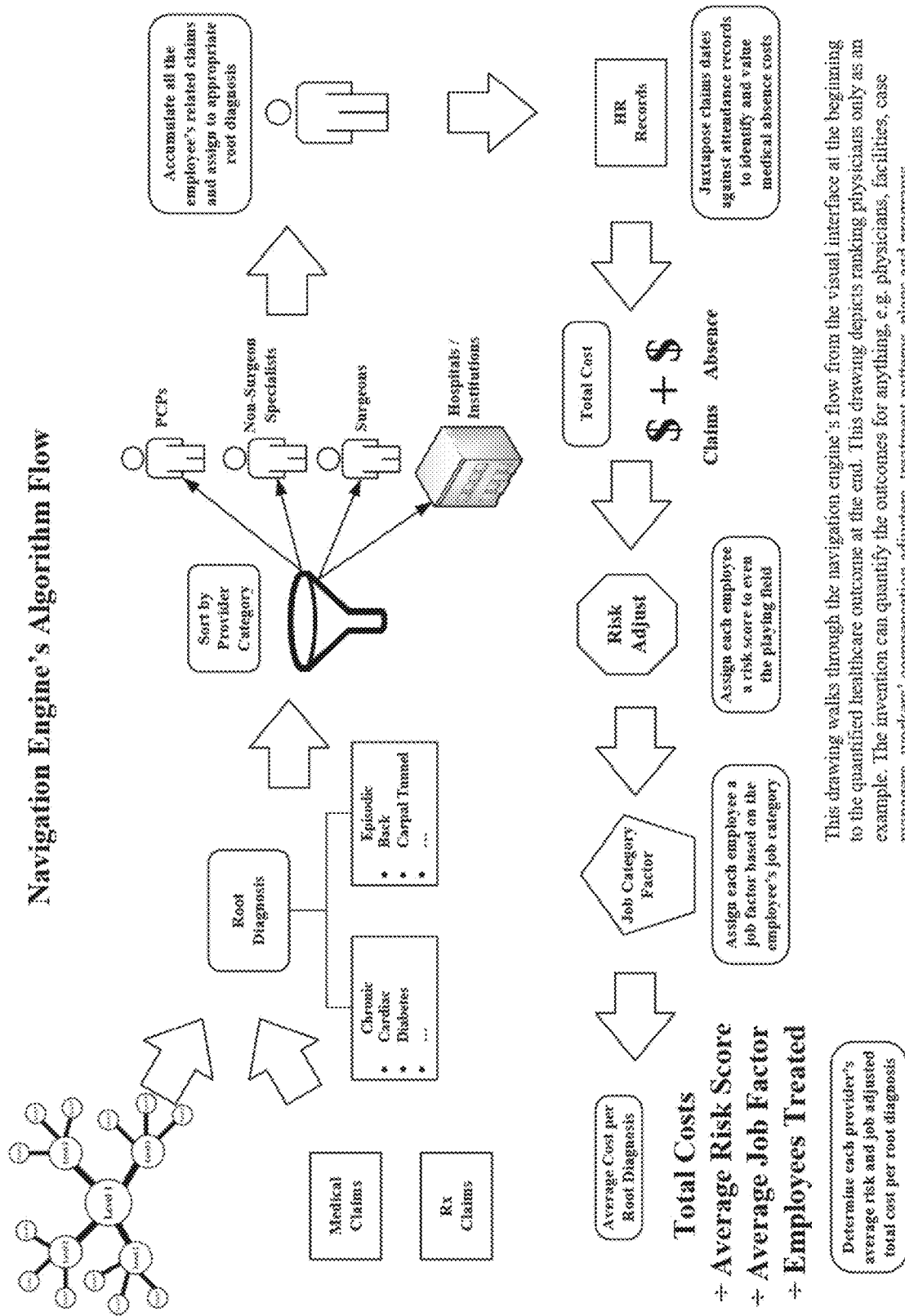
FIG. 27 walks through the navigation engine's algorithm flow from the visual interface at the beginning to the quantified healthcare outcome at the end. This drawing depicts quantifying the outcomes achieved by physicians only as an example. The invention can quantify the outcomes for any Healthcare Item.

The invention, up to this point, is depicted in FIG. 27.

The invention now shifts from calculating the historical average risk and job adjusted total cost when treating a root diagnosis, to predicting a particular patient's cost when treated for that condition.

For example, the prediction of a patient's total cost when going to a particular provider is determined by: (1) taking the provider's average risk and job adjusted cost for that root diagnosis, (2) multiplying it by the patient's risk score (1.000 for scores of 1.000 and below, the actual score for scores above 1.000), and (3) multiplying that product by the patient's job factor (if the patient is an employee).

The prediction is then compared to the actual costs. This comparison can be performed on historical data when the actual costs are known, or future data when the patient's actual costs are unknown, which would be the case when a person is using the search component of the navigation engine described below to select a provider.

Regression analysis is then employed to modify the risk score and job factor as they effect the root diagnosis, with the modifying factors deployed as additional elements in the prediction formula. This analysis may address components or subsets of the risk score and job factor, such as whether a diabetic condition (a factor in the risk score) should be given more or less weight when predicting the total costs for a particular root diagnosis.

The revised prediction is then compared to the actual costs, and the modifying factors adjusted in a "loop" of neural network and machine learning until the predicted costs equal the actual ones.

Figure 28:
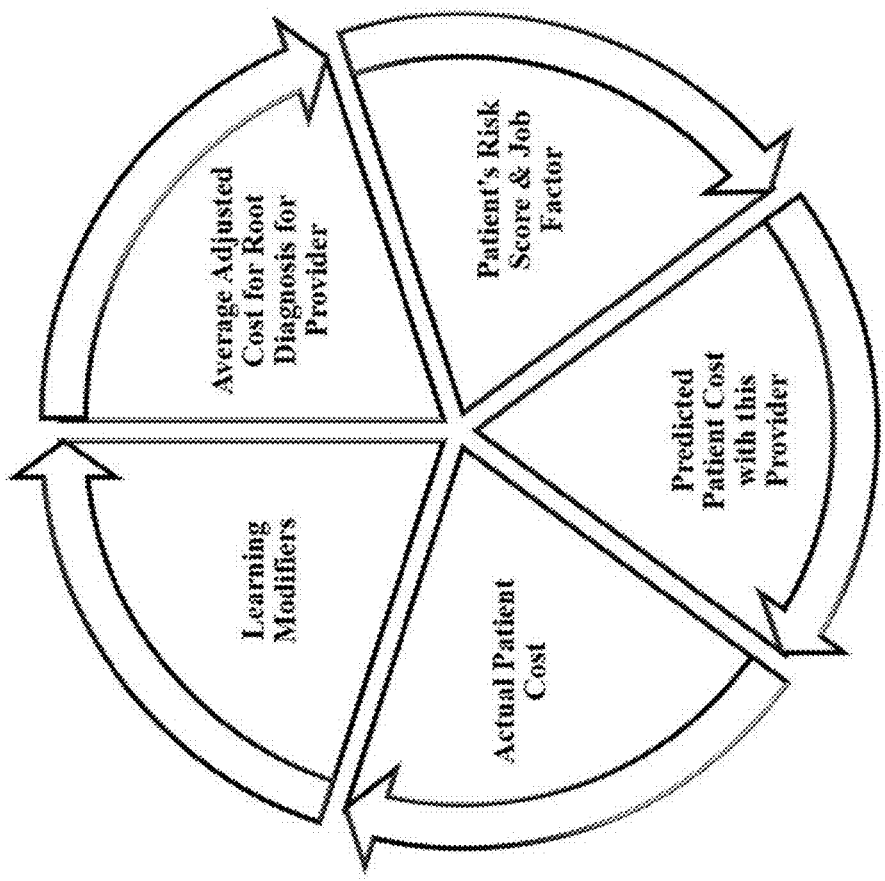
FIG. 28 shows the navigation engine's flow when predicting a quantified healthcare outcome (as opposed to calculating an historical one), and then the invention's neural network and machine learning feature. This drawing depicts predicting the outcome for a particular employee with a specified diagnosis seeing a particular provider only as an example. The invention can predict the outcomes for any Healthcare Item.

This neural network and machine learning feature of the invention is depicted in FIG. 28.

Finally, a user facing search component of the navigation engine may direct a patient to the providers with the optimal healthcare outcomes for that patient's particular problem root diagnosis). That "optimal" outcome is the lowest overall average adjusted costs over the entire continuum of care—claims plus absence costs. Not only are the absence costs a real cost to the employer, the employee or both, but they double as a measure of quality and indication of the effectiveness of the care. The quicker that a doctor got the employee better and back to work, the more effective the doctor was.

This transforms an open-ended question—"Which provider will attain the best outcome for a particular healthcare problem?"—to a question guaranteed to deliver an answer through drop-down menus that filter the results by root diagnoses, provider categories, geographic proximities, and provider network (in-network for the patient versus out-of-network). After selecting the root diagnosis, type of provider sought (PCP, Non-Surgeon Specialist, Surgeon, or Institution), desired geographic proximity, and whether the patient wants to see only in-network providers or out-of-network providers too, the search component of the navigation engine displays the top ranked providers in that category for that root diagnosis within the specified geographic proximity who are in the patient's provider network (or alternatively, providers both in and out of that network).

Figure 29:
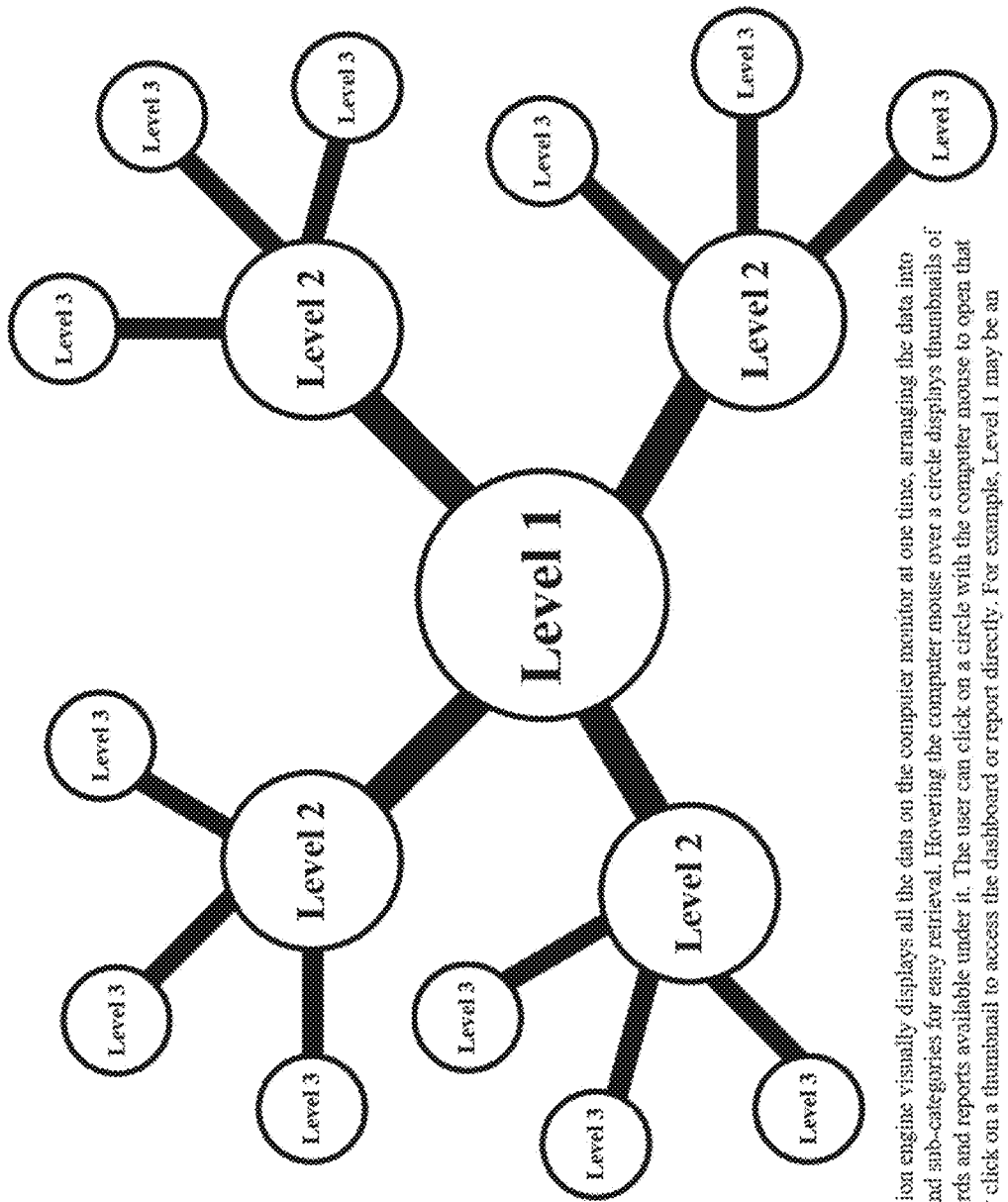
FIG. 29 shows how the navigation engine visually displays all the data on the computer monitor at one time, arranging the data into categories and sub-categories for easy retrieval by hoovering the computer mouse's curser over the desired data and clicking on it.

The navigation engine is deployed on a computer connected to a computer monitor and computer mouse. As shown in FIG. 29, the engine employs the novel approach of representing categories and sub-categories of material with functionally labeled circles connected in a hierarchical organization on a single computer screen. Descending circles in the hierarchy represent more detailed subsets of the material. Hovering the computer mouse over a circle displays thumbnails of the dashboards and reports available under it. For example, one category may be physicians, with sub-categories for primary care physicians (PCPs), specialists and surgeons. Another category may be diagnoses, with sub-categories for chronic versus episodic conditions, and then individual diagnoses under each.

The user can click on a circle with the computer mouse to open that category, or click on a thumbnail to access a dashboard or report directly.

This navigation technology improves the computer's functionality by transforming the literal display of data into a visual one on a single computer screen; thereby improving computer and network performance by decreasing the resources used to open and close screens while searching for the right one, while increasing the effectiveness and speed of the user's search process.

The search or navigation engine displays different results based on the type of user. For an employer's administrative personnel, the navigation engine displays all the data summarized on a single computer screen using the engine's novel circle hierarchy with thumbnails for the configurations in various dashboards and reports. For PCPs using a simplified search component of the navigation engine to make patient referrals, the navigation engine displays a list of the optimal surgeons, specialists and institutions. For an employer's employees and their dependents, the simplified user facing search component of the navigation engine displays all the optimal providers, including PCPs.

Rankings can be based on either average risk and job adjusted costs (claims plus absence costs), or predicted costs for the patient by taking a particular provider's average risk and job adjusted costs and applying the patient's risk score and job factor (before or after the risk score and job factor are modified through the regression analysis neural network and machine learning loop).

The section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein. The detailed description is not intended to be limiting or represent an exhaustive enumeration of the principles disclosed herein. It will be apparent to those of skill in the art that numerous changes may be made in such details without departing from the spirit of the principles disclosed herein.

Moreover, the Abstract is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus, the following claims are hereby incorporated into the Detailed Description, with each claim standing on its own as a separate embodiment.

The invention claimed is:

1. A method in a computing environment for ranking healthcare providers based on their outcomes, specialties, and treatment protocols for particular healthcare needs of an employer's employees, the method comprising:
   organizing medical and pharmacy claims made under an employer's health plan or other related programs in tables;
   organizing said employer's human resource records or other related records relating to employee absences, job categories and payroll in tables;
   identifying one or more distinct root diagnosis for each employee's organized medical and pharmacy claims;
   grouping together all said employees' claims related to a root diagnosis over an entire continuum of care for each identified root diagnosis;
   identifying absences related to each identified root diagnosis of each employee by juxtaposing the dates for all employee claims grouped under each corresponding root diagnosis against employee absence records;
   determining a value for the identified absences of each employee at each employee's corresponding pay rate or a normalized rate;
   combining for each root diagnosis of each employee a monetary cost attributed to all medical and pharmacy claims and said determined values of absence costs for each said root diagnosis;
   determining a risk score for each employee using age, gender, health and disease data, and pharmaceutical data contained in the organized claims and/or human resource records
   organizing the healthcare providers in tables;
   allocating to each provider in said tables that filed a claim grouped with an employee's root diagnosis both: (1) monetary cost attributed to each provider's claims grouped with a particular root diagnosis and related absence costs for each corresponding treated employee having said particular root diagnosis, and (2) monetary cost attributed to all downstream claims and related absence costs determined from direct and indirect referrals of an employee for a particular root diagnosis made by a corresponding provider to other providers;
   determining, for each provider, an average risk adjusted cost to treat an employee with a particular root diagnosis by: (1) combining monetary costs attributed to all employee claims and absence costs attributed to each provider when treating a particular root diagnosis along an entire continuum of care, (2) dividing said total attributed costs to each provider by determined average risk adjusted score of employees treated for said particular root diagnosis by each provider, (3) dividing each quotient from step (2) by a total number of employees treated for said particular root diagnosis by each provider;
   ranking said providers for each root diagnosis based on each provider's average risk adjusted costs, thereby determining medical and pharmacy claims plus absence costs to return an employee with a particular root diagnosis to work at an employer, from best, having lowest average cost, to worst, having highest average cost;
   presenting, via a system of visual searching on a computer screen, to a user searching for a healthcare provider for treating a particular root diagnosis, said ranked providers with healthcare outcomes for a particular root diagnosis, wherein said system of visual searching comprises:
      presenting on a single computer display screen groups of Healthcare Items related to treating particular root diagnoses within functionally labeled circles connected in a hierarchical order;
      organizing that order with a central circle branching off into a plurality of smaller circles, and from each of said plurality of smaller circles, branching off into a plurality of even smaller circles, with more detailed subsets of information related to a respective item presented in each circle as each of said circles hierarchically descend;
      linking two or more of the circles with stems, wherein lengths and widths of the stems indicating the connectedness of the underlying data representing the Healthcare Items in respective circles;
      displaying thumbnails of dashboards and/or reports available under a circle when the user hovers a cursor over it;
      in response to the user selecting a circle or a respective thumbnail of a dashboard and/or report, opening a new computer display screen from which the user can access said selected dashboards and/or reports.

2. The method of claim 1, further comprising:
analyzing treatment patterns and/or practices employed by each of said providers for each root diagnosis; and
ranking the treatment patterns and/or practices based on cost-based outcomes for each such root diagnosis based on average risk adjusted costs to treat employees with each such root diagnosis, wherein lower cost-based outcomes are designated better or best practices for each such root diagnosis.

3. The method of claim 2, wherein said analyzing of said treatment patterns and/or practices comprises using heterogeneous machine learning, decision-tree methodologies, and/or multiple regression analysis.

4. The method of claim 1, further comprising:
sorting the providers into four categories: (1) Primary Care Physicians (PCPs), (2) Non-Surgeon Specialists, (3) Surgeons, and (4) Institutions; and
ranking said sorted providers in each provider category for each root diagnosis based on each provider's average risk adjusted costs, thereby determining medical and pharmacy claims plus absence costs to return an employee with a particular root diagnosis to work at an employer, from best, having lowest average cost, to worst, having highest average cost.

5. The method of claim 1, further comprising:
creating a numerical job factor for each employee based on each corresponding employee's physical and mental exertions and stresses required for their job and/or other job demographics;
wherein said determining, for each provider, an average risk cost to treat an employee with a particular root diagnosis further comprises determining, for each provider, an average risk adjusted cost and job adjusted cost to treat an employee with a particular root diagnosis by: (1) combining monetary costs attributed to all employee claims and absence costs attributed to each provider when treating a particular root diagnosis along an entire continuum of care, (2) dividing said total attributed costs to each provider by determined average risk score of employees treated for said particular root diagnosis by each provider, (3) dividing each quotient from step (2) by created average job factor of employees treated for said particular root diagnosis by each provider, and (4) dividing such quotient from step (3) by a total number of employees treated for said particular root diagnosis by each provider.

6. The method of claim 5, further comprising:
determining a specific risk score of a particular person from the organized medical and pharmacy claims and/or human resource data;
determining a specific job factor of said particular person from the human resource records if said particular person is an employee of an employer having said organized human resource records; and
predicting costs of each provider when treating said particular person for a particular root diagnosis by applying said particular person's risk score and job factor to each provider's average risk and job adjusted cost to treat an employee with said particular root diagnosis.

7. The method of claim 6, further comprising:
comparing said predicted costs for each person to each said person's actual total costs;
employing regression analysis to modify risk score and job factor (and/or components thereof) as each effects root diagnosis, with modifying factors deployed as additional elements in said predicting for determining revised predicting costs of each provider; and
comparing said revised prediction costs to actual costs for each provider, and then adjusting the modifying factors in a loop of neural network and machine learning until the predicted costs equal the actual costs for each provider.

8. The method of claim 5, further comprising:
sorting the providers into four categories: (1) Primary Care Physicians (PCPs), (2) Non-Surgeon Specialists, (3) Surgeons, and (4) Institutions; and
ranking said sorted providers in each provider category for each root diagnosis based on each provider's average risk adjusted and job adjusted costs, thereby determining medical and pharmacy claims plus absence costs to return an employee with a particular root diagnosis to work at an employer, from best, having lowest average cost, to worst, having highest average cost.

9. The method of claim 1, wherein each determined risk score is supplemented with social determinants of health, health plan and/or clinical data.

10. The method of claim 1, further comprising filtering said presented providers via drop-down menus, accessible via said opened computer display screen and in response to selection by the user, by: (1) root diagnosis, (2) provider category, (3) geographic proximity to said user, and (4) in-network versus out-of-network for said user.

11. The method of claim 1, further comprising filtering said presented providers and/or Healthcare Items based on type of user by:
(1) in response to the user's selection of being an employer's administrative personnel, the system of visual searching displays all data configured in corresponding dashboards and reports,
(2) in response to the user's selection of being a Primary Care Physicians (PCP), the system of visual searching displays the optimal surgeons, specialists, and institutions for a particular root diagnosis, and
(3) in response to the user's selection of being an employer's employee or their dependent, the system of visual searching displays all optimal providers for a particular root diagnosis, including PCPs.

12. The method of claim 1, further comprising pooling data of employers located in a same geographical area.

13. The method of claim 1, wherein said presented ranked providers are sortable by the user using the system of visual searching based on overall average adjusted costs to treat said particular root diagnosis over an entire continuum of care for said particular root diagnosis.

14. A non-transitory computer-readable medium having computer executable code for ranking healthcare providers based on their outcomes, specialties, and treatment protocols for particular healthcare needs of an employer's employees, said code when executed by one or more processors performs the process of:
organizing medical and pharmacy claims made under an employer's health plan or other related programs in tables;
organizing said employer's human resource records or other related records relating to employee absences, job categories and payroll in tables;
identifying one or more distinct root diagnosis for each employee's organized medical and pharmacy claims;

grouping together all said employees' claims related to a root diagnosis over an entire continuum of care for each identified root diagnosis;

identifying absences related to each identified root diagnosis of each employee by juxtaposing the dates for all employee claims grouped under each corresponding root diagnosis against employee absence records;

determining a value for the identified absences of each employee at each employee's corresponding pay rate or a normalized rate;

combining for each root diagnosis of each employee a monetary cost attributed to all medical and pharmacy claims and said determined values of absence costs for each said root diagnosis;

determining a risk score for each employee using age, gender, health and disease data, and pharmaceutical data contained in the organized claims and/or human resource records;

organizing the healthcare providers in tables;

allocating to each provider in said tables that filed a claim grouped with an employee's root diagnosis both: (1) monetary cost attributed to each provider's claims grouped with a particular root diagnosis and related absence costs for each corresponding treated employee having said particular root diagnosis, and (2) monetary cost attributed to all downstream claims and related absence costs determined from direct and indirect referrals of an employee for a particular root diagnosis made by a corresponding provider to other providers;

determining, for each provider, an average risk adjust cost to treat an employee with a particular root diagnosis by: (1) combining monetary costs attributed to all employee claims and absence costs attributed to each provider when treating a particular root diagnosis along an entire continuum of care, (2) dividing said total attributed costs to each provider by determined average risk score of employees treated for said particular root diagnosis by each provider, and (3) dividing each quotient from step (2) by a total number of employees treated for said particular root diagnosis by each provider;

ranking sorted providers for each root diagnosis based on each provider's average risk adjusted costs, thereby determining medical and pharmacy claims plus absence costs to return an employee with a particular root diagnosis to work at an employer, from best, having lowest average cost, to worst, having highest average cost;

presenting, via a system of visual searching on a computer screen, to a user searching for a healthcare provider for treating a particular root diagnosis, said ranked providers with healthcare outcomes for a particular root diagnosis, wherein said system of visual searching comprises:

presenting on a single computer display screen groups of Healthcare Items related to treating particular root diagnoses within functionally labeled circles connected in a hierarchical order;

organizing that order with a central circle branching off into a plurality of smaller circles, and from each of said plurality of smaller circles, branching off into a plurality of even smaller circles, with more detailed subsets of information related to a respective item presented in each circle as each of said circles hierarchically descend;

linking two or more of the circles with stems, wherein lengths and widths of the stems indicating the connectedness of the underlying data representing the Healthcare Items in respective circles;

displaying thumbnails of dashboards and/or reports available under a circle when the user hovers a cursor over it;

in response to the user selecting a circle or a respective thumbnail of a dashboard and/or report, opening a new computer display screen from which the user can access said selected dashboards and/or reports.

15. The non-transitory computer readable medium of claim 14, wherein the performed process further comprises:

analyzing treatment patterns and/or practices employed by each of said sorted providers for each root diagnosis; and ranking the treatment patterns and/or practices based on cost-based outcomes for each such root diagnosis based on average risk adjusted costs to treat employees with each such root diagnosis, wherein lower cost-based outcomes are designated better or best practices for each such root diagnosis.

16. The non-transitory computer readable medium of claim 15, wherein said analyzing of said treatment patterns and/or practices comprises using heterogeneous machine learning, decision-tree methodologies, and/or multiple regression analysis.

17. The non-transitory computer readable medium of claim 14, further comprising:

sorting the providers into four categories: (1) Primary Care Physicians (PCPs), (2) Non-Surgeon Specialists, (3) Surgeons, and (4) Institutions; and ranking said sorted providers in each provider category for each root diagnosis based on each provider's average risk adjusted costs, thereby determining medical and pharmacy claims plus absence costs to return an employee with a particular root diagnosis to work at an employer, from best, having lowest average cost, to worst, having highest average cost.

18. The non-transitory computer readable medium of claim 14, further comprising:

creating a numerical job factor for each employee based on each corresponding employee's physical and mental exertions and stresses required for their job and/or other job demographics;

wherein said determining, for each provider, an average risk cost to treat an employee with a particular root diagnosis further comprises determining, for each provider, an average risk adjusted cost and job adjusted cost to treat an employee with a particular root diagnosis by: (1) combining monetary costs attributed to all employee claims and absence costs attributed to each provider when treating a particular root diagnosis along an entire continuum of care, (2) dividing said total attributed costs to each provider by determined average risk score of employees treated for said particular root diagnosis by each provider, (3) dividing each quotient from step (2) by created average job factor of employees treated for said particular root diagnosis by each provider, and (4) dividing such quotient from step (3) by a total number of employees treated for said particular root diagnosis by such provider.

19. The non-transitory computer readable medium of claim 18, wherein the performed process further comprises:

determining a specific risk score of a particular person from the organized medical and pharmacy claims and/or human resource data;

determining a specific job factor of said particular person from the human resource records if said particular person is an employee of an employer having said organized human resource records; and predicting costs of each provider when treating said particular person for a particular root diagnosis by applying said particular person's risk score and job factor to each provider's average risk and job adjusted cost to treat an employee with said particular root diagnosis.

20. The non-transitory computer readable medium of claim 19, wherein the performed process further comprises:

comparing said predicted costs for each person to each said person's actual total costs;

employing regression analysis to modify risk score and job factor (and/or components thereof) as each effects root diagnosis, with modifying factors deployed as additional elements in said predicting for determining revised predicting costs of each provider; and comparing said revised prediction costs to actual costs for each provider, and then adjusting the modifying factors in a loop of neural network and machine learning until the predicted costs equal the actual costs for each provider.

21. The non-transitory computer readable medium of claim 18, further comprising:

sorting the providers into four categories: (1) Primary Care Physicians (PCPs), (2) Non-Surgeon Specialists, (3) Surgeons, and (4) Institutions; and ranking said sorted providers in each provider category for each root diagnosis based on each provider's average risk adjusted and job adjusted costs, thereby determining medical and pharmacy claims plus absence costs to return an employee with a particular root diagnosis to work at an employer, from best, having lowest average cost, to worst, having highest average cost.

22. The method of claim 14, wherein each determined risk score is supplemented with social determinants of health, health plan and/or clinical data.

23. The non-transitory computer readable medium of claim 14, further comprising filtering said presented providers via drop-down menus, accessible via said opened computer display screen and in response to selection by the user, by: (1) root diagnosis, (2) provider category, (3) geographic proximity to said user, and (4) in-network versus out-of-network for said user.

24. The non-transitory computer readable medium of claim 14, further comprising filtering said presented providers and/or Healthcare Items based on type of user by:

(1) in response to the user's selection of being an employer's administrative personnel, the system of visual searching displays all data configured in corresponding dashboards and reports, (2) in response to the user's selection of being a Primary Care Physicians (PCP), the system of visual searching displays the optimal surgeons, specialists, and institutions for a particular root diagnosis, and (3) in response to the user's selection of being an employer's employee or their dependent, the system of visual searching displays all optimal providers for a particular root diagnosis, including PCPs.

25. The non-transitory computer readable medium of claim 14, further comprising pooling data of employers located in a same geographical area.

26. The non-transitory computer readable medium of claim 14, wherein said presented ranked providers are sortable by the user using the system of visual searching based on overall average adjusted costs to treat said particular root diagnosis over an entire continuum of care for said particular root diagnosis.

* * * * *